(12) United States Patent
Rozners et al.

(10) Patent No.: US 10,260,089 B2
(45) Date of Patent: Apr. 16, 2019

(54) COMPOSITIONS AND METHODS FOR RECOGNITION OF RNA USING TRIPLE HELICAL PEPTIDE NUCLEIC ACIDS

(71) Applicant: The Research Foundation for the State University of New York, Binghamton, NY (US)

(72) Inventors: Eriks Rozners, Binghamton, NY (US); Thomas Zengeya, Frederick, MD (US)

(73) Assignee: The Research Foundation of The State University of New York, Binghamton, NY (US)

( * ) Notice: Subject to any disclaimer, the term of this patent is extended or adjusted under 35 U.S.C. 154(b) by 498 days.

(21) Appl. No.: 14/066,006

(22) Filed: Oct. 29, 2013

(65) Prior Publication Data
US 2014/0206838 A1  Jul. 24, 2014

Related U.S. Application Data

(60) Provisional application No. 61/719,691, filed on Oct. 29, 2012.

(51) Int. Cl.
| | | |
|---|---|---|
| C12Q 1/68 | (2018.01) | |
| C12Q 1/6839 | (2018.01) | |
| C07K 7/08 | (2006.01) | |
| C07K 9/00 | (2006.01) | |

(52) U.S. Cl.
CPC .............. C12Q 1/6839 (2013.01); C07K 7/08 (2013.01); C07K 9/00 (2013.01)

(58) Field of Classification Search
None
See application file for complete search history.

(56) References Cited

U.S. PATENT DOCUMENTS

| | | |
|---|---|---|
| 5,539,082 A | 7/1996 | Nielsen et al. |
| 5,547,835 A | 8/1996 | Koster |
| 5,641,625 A * | 6/1997 | Ecker et al. .............. 435/6.18 |
| 5,645,985 A | 7/1997 | Froehler et al. |
| 5,691,141 A | 11/1997 | Koster |
| 5,714,331 A | 2/1998 | Buchardt et al. |
| 5,719,262 A | 2/1998 | Buchardt et al. |
| 5,736,336 A | 4/1998 | Buchardt et al. |
| 5,766,855 A | 6/1998 | Buchardt et al. |
| 5,786,461 A | 7/1998 | Buchardt et al. |
| 5,830,653 A | 11/1998 | Froehler et al. |
| 5,871,918 A | 2/1999 | Thorp et al. |
| 6,132,971 A | 10/2000 | Thorp et al. |
| 6,190,866 B1 | 2/2001 | Nielsen et al. |
| 6,194,144 B1 | 2/2001 | Koster |
| 6,225,450 B1 | 5/2001 | Koster |
| 6,238,871 B1 | 5/2001 | Koster |
| 6,248,878 B1 | 6/2001 | Matulic-Adamic et al. |
| 6,265,380 B1 | 7/2001 | Tung et al. |
| 6,300,318 B1 | 10/2001 | Nielsen et al. |
| 6,357,163 B1 | 3/2002 | Buchardt et al. |
| 6,361,951 B1 | 3/2002 | Thorp et al. |
| 6,369,227 B1 | 4/2002 | Lam et al. |
| 6,380,368 B1 | 4/2002 | Froehler et al. |
| 6,395,474 B1 | 5/2002 | Buchardt et al. |
| 6,403,583 B1 | 6/2002 | Lam et al. |
| 6,414,112 B1 | 7/2002 | Buchardt et al. |
| 6,441,130 B1 | 8/2002 | Egholm et al. |
| 6,451,968 B1 | 9/2002 | Egholm et al. |
| 6,500,855 B1 | 12/2002 | Lam et al. |
| 6,613,873 B1 | 9/2003 | Buchardt et al. |
| 6,617,309 B2 | 9/2003 | Tung et al. |
| 6,653,295 B2 | 11/2003 | Glunz et al. |
| 6,664,373 B1 | 12/2003 | Curtis et al. |
| 6,686,442 B2 | 2/2004 | Neilsen et al. |
| 6,710,058 B2 | 3/2004 | Jacobson et al. |
| 6,710,163 B1 | 3/2004 | Buchardt et al. |
| 6,710,164 B1 | 3/2004 | Nielsen et al. |
| 6,713,602 B1 | 3/2004 | Buchardt et al. |
| 6,734,161 B1 | 5/2004 | Nielsen et al. |
| 6,875,593 B2 | 4/2005 | Froehler et al. |
| 6,878,805 B2 | 4/2005 | Manoharan et al. |
| 6,936,418 B2 | 8/2005 | Dutreix et al. |
| 6,946,292 B2 | 9/2005 | Kanda et al. |
| 6,951,872 B2 | 10/2005 | Jacobson et al. |
| 6,962,783 B2 | 11/2005 | Froehler et al. |
| 7,038,037 B2 | 5/2006 | Maier et al. |
| 7,049,068 B2 | 5/2006 | Thorp et al. |
| 7,057,027 B2 | 6/2006 | Froehler et al. |

(Continued)

FOREIGN PATENT DOCUMENTS

WO  WO2010130708  11/2010

OTHER PUBLICATIONS

Cassidy et. al, Nucleic Acids Research, vol. 25(24):4891-4898 (1997).*
Muse et al. (ACS chemical biology (2013) vol. 8, No. 8, p. 1683-1686, published May 30, 2013).*
Li et al. (J. Am. Chem. Soc. 2010, 132, 8676-8681).*
Rusling (Nucleic Acids Research, 2005, 33:3025-3032).*
Cassidy et al. (Nucleic Acids Research, 1997, vol. 25, No. 24, pp. 4891-4898).*
Hildbrad et al. (J. Am. Chem. Soc. 1997, 119, 5499-5511).*
Hansen et al. (Nucleic acids Research, 2009, vol. 37, No. 13, pp. 4498-4507).*
Sazani et al. (Nature Biotechnology, 2002, vol. 20, pp. 1228-1233).*
Zengeya et al. (Angew. Chem. Int. Ed. 2012, 51, 12593-12596, published Nov. 4, 2012).*

(Continued)

*Primary Examiner* — Juliet C Switzer
(74) *Attorney, Agent, or Firm* — Tully Rinckey PLLC; Steven M. Hoffberg

(57) ABSTRACT

Peptide nucleic acids containing thymidine and 2-aminopyridine (M) nucleobases formed stable and sequence selective triple helices with double stranded RNA at physiologically relevant conditions. The M-modified PNA displayed unique RNA selectivity by having two orders of magnitude higher affinity for the double stranded RNAs than for the same DNA sequences. Preliminary results suggested that nucleobase-modified PNA could bind and recognize double helical precursors of microRNAs.

13 Claims, 19 Drawing Sheets

Specification includes a Sequence Listing.

(56) References Cited

U.S. PATENT DOCUMENTS

| | | |
|---|---|---|
| 7,098,192 B2 | 8/2006 | Karras |
| 7,157,470 B2 | 1/2007 | Smallheer et al. |
| 7,199,107 B2 | 4/2007 | Dobie et al. |
| 7,223,833 B1 | 5/2007 | Nielsen et al. |
| 7,235,653 B2 | 6/2007 | Bennett et al. |
| 7,253,180 B2 | 8/2007 | Chen et al. |
| 7,276,599 B2 | 10/2007 | Moore et al. |
| 7,297,494 B2 | 11/2007 | Bao et al. |
| 7,307,069 B2 | 12/2007 | Karras |
| 7,312,214 B2 | 12/2007 | Qiao et al. |
| 7,339,051 B2 | 3/2008 | Crooke et al. |
| 7,348,418 B2 | 3/2008 | Singh et al. |
| 7,368,560 B2 | 5/2008 | Hud |
| 7,378,485 B2 | 5/2008 | Buchardt et al. |
| 7,381,732 B2 | 6/2008 | Lam et al. |
| 7,388,017 B2 | 6/2008 | Tung et al. |
| 7,390,882 B2 | 6/2008 | Cairns et al. |
| 7,393,683 B2 | 7/2008 | Kanda et al. |
| 7,410,772 B2 | 8/2008 | Ashkenazi et al. |
| 7,425,446 B2 | 9/2008 | Kanda et al. |
| 7,429,604 B2 | 9/2008 | Corte et al. |
| 7,432,044 B2 | 10/2008 | Kirchhofer et al. |
| 7,507,859 B2 | 3/2009 | Grinstaff et al. |
| 7,517,659 B2 | 4/2009 | Curtis et al. |
| 7,524,863 B2 | 4/2009 | Smallheer et al. |
| 7,541,344 B2 | 6/2009 | Bhat et al. |
| 7,547,768 B2 | 6/2009 | Dowd et al. |
| 7,585,953 B2 | 9/2009 | Chen et al. |
| 7,615,529 B2 | 11/2009 | Kong-Beltran et al. |
| 7,618,632 B2 | 11/2009 | Collins et al. |
| 7,622,265 B2 | 11/2009 | Fan et al. |
| 7,662,929 B2 | 2/2010 | Brown et al. |
| 7,678,895 B2 | 3/2010 | Bennett et al. |
| 7,683,036 B2 | 3/2010 | Esau et al. |
| 7,691,568 B2 | 4/2010 | Niwa et al. |
| 7,691,810 B2 | 4/2010 | Yamada et al. |
| 7,696,345 B2 | 4/2010 | Allerson et al. |
| 7,704,503 B2 | 4/2010 | Kolls et al. |
| 7,713,944 B2 | 5/2010 | Kinberger et al. |
| 7,718,628 B2 | 5/2010 | Dobie et al. |
| 7,737,325 B2 | 6/2010 | Kanda et al. |
| 7,741,442 B2 | 6/2010 | Kanda et al. |
| 7,749,504 B2 | 7/2010 | Cairns et al. |
| 7,754,441 B2 | 7/2010 | de Sauvage et al. |
| 7,754,450 B2 | 7/2010 | Grasso et al. |
| 7,759,318 B1 | 7/2010 | Perera et al. |
| 7,759,319 B2 | 7/2010 | Lollo et al. |
| 7,767,403 B2 | 8/2010 | Frantz et al. |
| 7,786,292 B2 | 8/2010 | Karelson et al. |
| 7,790,691 B2 | 9/2010 | Kraynack et al. |
| 7,803,915 B2 | 9/2010 | Cairns et al. |
| 7,807,372 B2 | 10/2010 | Mirkin et al. |
| 7,812,149 B2 | 10/2010 | Prakash et al. |
| 7,829,584 B2 | 11/2010 | Player et al. |
| 7,846,725 B2 | 12/2010 | Kanda et al. |
| 7,858,330 B2 | 12/2010 | Hongo et al. |
| 7,884,086 B2 | 2/2011 | Bennett et al. |
| 7,888,478 B2 | 2/2011 | Chang et al. |
| 7,897,582 B2 | 3/2011 | Bennett et al. |
| 7,902,163 B2 | 3/2011 | Bennett et al. |
| 7,919,612 B2 | 4/2011 | Baker et al. |
| 7,923,538 B2 | 4/2011 | Shitara et al. |
| 7,939,268 B2 | 5/2011 | Frantz et al. |
| 7,951,546 B2 | 5/2011 | Frantz et al. |
| 7,960,355 B2 | 6/2011 | Bennett et al. |
| 7,981,868 B2 | 7/2011 | Monia et al. |
| 7,985,844 B2 | 7/2011 | Brown et al. |
| 7,989,595 B2 | 8/2011 | Dennis et al. |
| 7,994,290 B2 | 8/2011 | Shitara et al. |
| 8,008,004 B2 | 8/2011 | Phillips |
| 8,012,947 B2 | 9/2011 | Tomic et al. |
| 8,039,595 B2 | 10/2011 | Kanda et al. |
| 8,067,175 B2 | 11/2011 | Varmus et al. |
| 8,067,232 B2 | 11/2011 | Kanda et al. |
| 8,084,200 B2 | 12/2011 | Ashkenazi et al. |
| 8,084,459 B2 | 12/2011 | Kok et al. |
| 8,101,185 B2 | 1/2012 | Kanda et al. |
| 8,106,025 B2 | 1/2012 | Bennett et al. |
| 8,110,195 B2 | 2/2012 | Kanda et al. |
| 8,110,558 B2 | 2/2012 | Bennett et al. |
| 8,124,745 B2 | 2/2012 | Allerson et al. |
| 8,129,515 B2 | 3/2012 | Esau et al. |
| 8,133,876 B2 | 3/2012 | Bennett et al. |
| 8,158,760 B2 | 4/2012 | Kanda et al. |
| 8,178,506 B2 | 5/2012 | Lollo et al. |
| 8,183,363 B2 | 5/2012 | Karras |
| 8,193,246 B2 | 6/2012 | Panzner et al. |
| 8,206,901 B2 | 6/2012 | Freskgard et al. |
| 8,252,756 B2 | 8/2012 | Mirkin et al. |
| 8,278,042 B2 | 10/2012 | Cairns et al. |
| 2002/0032175 A1 | 3/2002 | Tung et al. |
| 2002/0106683 A1 | 8/2002 | Thorp et al. |
| 2002/0146718 A1 | 10/2002 | Buchardt et al. |
| 2002/0160383 A1 | 10/2002 | Buchardt et al. |
| 2002/0183324 A1 | 12/2002 | Jacobson et al. |
| 2003/0004344 A1 | 1/2003 | Lam et al. |
| 2003/0064962 A1 | 4/2003 | Glunz et al. |
| 2003/0087268 A1 | 5/2003 | Yue et al. |
| 2003/0105286 A1 | 6/2003 | Egholm et al. |
| 2003/0108544 A1 | 6/2003 | Gurney et al. |
| 2003/0115614 A1 | 6/2003 | Kanda et al. |
| 2003/0148408 A1 | 8/2003 | Frantz et al. |
| 2003/0152953 A1 | 8/2003 | Feder et al. |
| 2003/0180734 A1 | 9/2003 | Buchardt et al. |
| 2003/0228305 A1 | 12/2003 | Frantz et al. |
| 2003/0228319 A1 | 12/2003 | Frantz et al. |
| 2003/0236389 A1 | 12/2003 | Shimkets et al. |
| 2004/0006062 A1 | 1/2004 | Smallheer et al. |
| 2004/0006203 A1 | 1/2004 | Maier et al. |
| 2004/0009541 A1 | 1/2004 | Singh et al. |
| 2004/0009602 A1 | 1/2004 | Seidman et al. |
| 2004/0009938 A1 | 1/2004 | Manoharan et al. |
| 2004/0014051 A1 | 1/2004 | Brown-Driver et al. |
| 2004/0023917 A1 | 2/2004 | Bennett et al. |
| 2004/0033977 A1 | 2/2004 | Bennett et al. |
| 2004/0033978 A1 | 2/2004 | Anderson et al. |
| 2004/0034191 A1 | 2/2004 | Manoharan et al. |
| 2004/0049021 A1 | 3/2004 | Anderson et al. |
| 2004/0059087 A1 | 3/2004 | Buchardt et al. |
| 2004/0063115 A1 | 4/2004 | Tang et al. |
| 2004/0063179 A1 | 4/2004 | Curtis et al. |
| 2004/0093621 A1 | 5/2004 | Shitara et al. |
| 2004/0101853 A1 | 5/2004 | Bennett et al. |
| 2004/0109865 A1 | 6/2004 | Niwa et al. |
| 2004/0110704 A1 | 6/2004 | Yamane et al. |
| 2004/0132718 A1 | 7/2004 | Jacobson et al. |
| 2004/0142346 A1 | 7/2004 | Baker et al. |
| 2004/0146902 A1 | 7/2004 | Ecker et al. |
| 2004/0147022 A1 | 7/2004 | Baker et al. |
| 2004/0147023 A1 | 7/2004 | Baker et al. |
| 2004/0147470 A1 | 7/2004 | Manoharan et al. |
| 2004/0161777 A1 | 8/2004 | Baker et al. |
| 2004/0161844 A1 | 8/2004 | Baker et al. |
| 2004/0171028 A1 | 9/2004 | Baker et al. |
| 2004/0171029 A1 | 9/2004 | Prakash et al. |
| 2004/0171031 A1 | 9/2004 | Baker et al. |
| 2004/0171032 A1 | 9/2004 | Baker et al. |
| 2004/0171033 A1 | 9/2004 | Baker et al. |
| 2004/0171564 A1 | 9/2004 | Honkanen et al. |
| 2004/0171566 A1 | 9/2004 | Monia et al. |
| 2004/0171570 A1 | 9/2004 | Allerson et al. |
| 2004/0180847 A1 | 9/2004 | Dobie et al. |
| 2004/0185479 A1 | 9/2004 | Andrews et al. |
| 2004/0198969 A1 | 10/2004 | Baldwin et al. |
| 2004/0203024 A1 | 10/2004 | Baker et al. |
| 2004/0229277 A1 | 11/2004 | Frantz et al. |
| 2004/0235164 A1 | 11/2004 | Bennett et al. |
| 2004/0241703 A1 | 12/2004 | DeSauvage et al. |
| 2004/0242860 A1 | 12/2004 | Frantz et al. |
| 2004/0254158 A1 | 12/2004 | Qiao et al. |
| 2004/0254358 A1 | 12/2004 | Manoharan et al. |
| 2004/0258696 A1 | 12/2004 | Frantz et al. |
| 2004/0259150 A1 | 12/2004 | Nakamura et al. |
| 2004/0266706 A1 | 12/2004 | Manoharan |

(56) References Cited

U.S. PATENT DOCUMENTS

| | | |
|---|---|---|
| 2004/0266731 A1 | 12/2004 | Tung et al. |
| 2005/0009041 A1 | 1/2005 | Buchardt et al. |
| 2005/0014224 A1 | 1/2005 | Collins et al. |
| 2005/0019915 A1 | 1/2005 | Bennett et al. |
| 2005/0026160 A1 | 2/2005 | Allerson et al. |
| 2005/0026857 A1 | 2/2005 | Brown-Driver et al. |
| 2005/0031613 A1 | 2/2005 | Nakamura et al. |
| 2005/0032067 A1 | 2/2005 | Prakash et al. |
| 2005/0032068 A1 | 2/2005 | Prakash et al. |
| 2005/0032069 A1 | 2/2005 | Manoharan et al. |
| 2005/0037370 A1 | 2/2005 | Baker et al. |
| 2005/0042216 A1 | 2/2005 | Frantz et al. |
| 2005/0042647 A1 | 2/2005 | Baker et al. |
| 2005/0053965 A1 | 3/2005 | Baker et al. |
| 2005/0053976 A1 | 3/2005 | Baker et al. |
| 2005/0053981 A1 | 3/2005 | Swayze et al. |
| 2005/0059016 A1 | 3/2005 | Ecker et al. |
| 2005/0059066 A1 | 3/2005 | Swayze et al. |
| 2005/0064492 A1 | 3/2005 | DeSauvage et al. |
| 2005/0074801 A1 | 4/2005 | Monia et al. |
| 2005/0074879 A1 | 4/2005 | Karras |
| 2005/0075307 A1 | 4/2005 | Bennett et al. |
| 2005/0080032 A1 | 4/2005 | Gross et al. |
| 2005/0080246 A1 | 4/2005 | Allerson et al. |
| 2005/0100885 A1 | 5/2005 | Crooke et al. |
| 2005/0106598 A1 | 5/2005 | Manoharan et al. |
| 2005/0106644 A1 | 5/2005 | Cairns et al. |
| 2005/0107324 A1 | 5/2005 | Bennett et al. |
| 2005/0107595 A1 | 5/2005 | Cairns et al. |
| 2005/0112129 A1 | 5/2005 | Phillips |
| 2005/0112770 A1 | 5/2005 | Nakamura et al. |
| 2005/0118605 A9 | 6/2005 | Baker et al. |
| 2005/0119470 A1 | 6/2005 | Manoharan et al. |
| 2005/0123925 A1 | 6/2005 | Ashkenazi et al. |
| 2005/0142581 A1 | 6/2005 | Griffey et al. |
| 2005/0153336 A1 | 7/2005 | Bennett et al. |
| 2005/0164250 A1 | 7/2005 | Ashkenazi et al. |
| 2005/0170368 A1 | 8/2005 | Ashkenazi et al. |
| 2005/0202459 A1 | 9/2005 | Hud |
| 2005/0208523 A1 | 9/2005 | Ashkenazi et al. |
| 2005/0226867 A1 | 10/2005 | Iida et al. |
| 2005/0226868 A1 | 10/2005 | Ashkenazi et al. |
| 2005/0226869 A1 | 10/2005 | Chang et al. |
| 2005/0233358 A1 | 10/2005 | Thorp et al. |
| 2005/0238650 A1 | 10/2005 | Crowley et al. |
| 2005/0245474 A1 | 11/2005 | Baker et al. |
| 2005/0260634 A1 | 11/2005 | Baldwin et al. |
| 2005/0260755 A1 | 11/2005 | Baker et al. |
| 2005/0261218 A1 | 11/2005 | Esau et al. |
| 2005/0262593 A1 | 11/2005 | Kanda et al. |
| 2005/0272120 A1 | 12/2005 | Dowd et al. |
| 2005/0287138 A1 | 12/2005 | Iida et al. |
| 2005/0287548 A1 | 12/2005 | Bao et al. |
| 2006/0002943 A1 | 1/2006 | Smith |
| 2006/0009455 A1 | 1/2006 | Corte et al. |
| 2006/0024793 A1 | 2/2006 | Yamada et al. |
| 2006/0046255 A1 | 3/2006 | Buchardt et al. |
| 2006/0057148 A1 | 3/2006 | Ashkenazi et al. |
| 2006/0063254 A1 | 3/2006 | Kanda et al. |
| 2006/0064781 A1 | 3/2006 | Kanda et al. |
| 2006/0073505 A1 | 4/2006 | Griffey et al. |
| 2006/0078990 A1 | 4/2006 | Kanda et al. |
| 2006/0078991 A1 | 4/2006 | Kanda et al. |
| 2006/0084120 A1 | 4/2006 | Kirchhofer et al. |
| 2006/0089496 A1 | 4/2006 | Lam et al. |
| 2006/0099592 A1 | 5/2006 | Freskgard et al. |
| 2006/0140961 A1 | 6/2006 | Frantz et al. |
| 2006/0142193 A1 | 6/2006 | Wei et al. |
| 2006/0142232 A1 | 6/2006 | Kinberger et al. |
| 2006/0147373 A1 | 7/2006 | Cairns et al. |
| 2006/0147374 A1 | 7/2006 | Frantz et al. |
| 2006/0160731 A1 | 7/2006 | Buchardt et al. |
| 2006/0160997 A1 | 7/2006 | Cairns et al. |
| 2006/0210570 A1 | 9/2006 | Fan et al. |
| 2006/0216232 A1 | 9/2006 | Chang et al. |
| 2006/0217339 A1 | 9/2006 | Karras |
| 2006/0241071 A1 | 10/2006 | Grinstaff et al. |
| 2006/0241072 A1 | 10/2006 | Baker |
| 2006/0247243 A1 | 11/2006 | Smallheer et al. |
| 2006/0251662 A1 | 11/2006 | Chang et al. |
| 2006/0252722 A1 | 11/2006 | Lollo et al. |
| 2006/0257930 A1 | 11/2006 | Kolls et al. |
| 2006/0270594 A1 | 11/2006 | Kong-Beltran et al. |
| 2006/0281680 A1 | 12/2006 | Gerber et al. |
| 2006/0293269 A1 | 12/2006 | Bennett et al. |
| 2007/0010009 A1 | 1/2007 | Kanda et al. |
| 2007/0015722 A1 | 1/2007 | Kraynack et al. |
| 2007/0041983 A1 | 2/2007 | Ashkenazi et al. |
| 2007/0048218 A1 | 3/2007 | Frantz et al. |
| 2007/0048326 A1 | 3/2007 | Cairns et al. |
| 2007/0048825 A1 | 3/2007 | Dowd et al. |
| 2007/0049547 A1 | 3/2007 | Esau et al. |
| 2007/0053835 A1 | 3/2007 | DeSauvage et al. |
| 2007/0054361 A1 | 3/2007 | Ashkenazi et al. |
| 2007/0054869 A1 | 3/2007 | Bennett et al. |
| 2007/0065861 A1 | 3/2007 | Lemischka et al. |
| 2007/0065862 A1 | 3/2007 | Lemischka et al. |
| 2007/0087006 A1 | 4/2007 | Frantz et al. |
| 2007/0098634 A1 | 5/2007 | Gurney et al. |
| 2007/0117124 A1 | 5/2007 | Baldwin et al. |
| 2007/0135364 A1 | 6/2007 | Bennett et al. |
| 2007/0148165 A1 | 6/2007 | Shitara et al. |
| 2007/0161547 A1 | 7/2007 | Bhat et al. |
| 2007/0207142 A1 | 9/2007 | Crowley et al. |
| 2007/0212735 A1 | 9/2007 | Ashkenazi et al. |
| 2007/0219122 A1 | 9/2007 | Glazer et al. |
| 2007/0219350 A1 | 9/2007 | Frantz et al. |
| 2007/0224201 A1 | 9/2007 | Wu et al. |
| 2007/0225282 A1 | 9/2007 | Player et al. |
| 2007/0231323 A1 | 10/2007 | Phillips |
| 2007/0243193 A1 | 10/2007 | Frantz et al. |
| 2007/0259830 A1 | 11/2007 | Karelson et al. |
| 2007/0265436 A1 | 11/2007 | Frantz et al. |
| 2007/0269446 A1 | 11/2007 | de Sauvage et al. |
| 2007/0276139 A1 | 11/2007 | Song et al. |
| 2007/0286856 A1 | 12/2007 | Brown et al. |
| 2008/0009456 A1 | 1/2008 | Dobie et al. |
| 2008/0027019 A1 | 1/2008 | Vickers et al. |
| 2008/0039618 A1 | 2/2008 | Allerson et al. |
| 2008/0051359 A1 | 2/2008 | Karras |
| 2008/0095765 A1 | 4/2008 | Ilda et al. |
| 2008/0096215 A1 | 4/2008 | Ashkenazi et al. |
| 2008/0102468 A1 | 5/2008 | Ashkenazi et al. |
| 2008/0119470 A1 | 5/2008 | Kok et al. |
| 2008/0124331 A1 | 5/2008 | Cairns et al. |
| 2008/0124732 A1 | 5/2008 | Nakamura et al. |
| 2008/0124739 A1 | 5/2008 | Dowd et al. |
| 2008/0131920 A1 | 6/2008 | Levin |
| 2008/0146495 A1 | 6/2008 | Lama |
| 2008/0146788 A1 | 6/2008 | Bhat et al. |
| 2008/0166294 A1 | 7/2008 | de Sauvage et al. |
| 2008/0193446 A1 | 8/2008 | Phillips |
| 2008/0194503 A1 | 8/2008 | Monia et al. |
| 2008/0199960 A1 | 8/2008 | Juliano et al. |
| 2008/0207541 A1 | 8/2008 | Migawa et al. |
| 2008/0213266 A1 | 9/2008 | Iida et al. |
| 2008/0227106 A1 | 9/2008 | Cairns et al. |
| 2008/0227196 A1 | 9/2008 | Kanda et al. |
| 2008/0241130 A1 | 10/2008 | Wright et al. |
| 2008/0241884 A1 | 10/2008 | Shitara et al. |
| 2008/0261301 A1 | 10/2008 | Kanda et al. |
| 2008/0261904 A1 | 10/2008 | Bhat et al. |
| 2008/0274993 A1 | 11/2008 | Gerber et al. |
| 2008/0306016 A1 | 12/2008 | Mirkin et al. |
| 2008/0306153 A1 | 12/2008 | Panzner et al. |
| 2008/0311669 A1 | 12/2008 | Mirkin et al. |
| 2008/0318239 A1 | 12/2008 | Frantz et al. |
| 2009/0004186 A1 | 1/2009 | Shitara et al. |
| 2009/0017473 A1 | 1/2009 | Frantz et al. |
| 2009/0028877 A1 | 1/2009 | Iida et al. |
| 2009/0041749 A1 | 2/2009 | Dennis et al. |
| 2009/0048435 A1 | 2/2009 | Bennett et al. |
| 2009/0053226 A1 | 2/2009 | Crowley et al. |
| 2009/0054631 A1 | 2/2009 | Ashkenazi et al. |

(56) References Cited

U.S. PATENT DOCUMENTS

| | | |
|---|---|---|
| 2009/0068178 A1 | 3/2009 | Crowley et al. |
| 2009/0068251 A1 | 3/2009 | Tomic et al. |
| 2009/0075278 A1 | 3/2009 | Frantz et al. |
| 2009/0075279 A1 | 3/2009 | Frantz et al. |
| 2009/0075302 A1 | 3/2009 | Frantz et al. |
| 2009/0075317 A1 | 3/2009 | Kirchhofer et al. |
| 2009/0081660 A1 | 3/2009 | Cairns et al. |
| 2009/0117566 A1 | 5/2009 | Frantz et al. |
| 2009/0136928 A1 | 5/2009 | Cairns et al. |
| 2009/0142259 A1 | 6/2009 | Gao et al. |
| 2009/0142806 A1 | 6/2009 | Carreno et al. |
| 2009/0143312 A1 | 6/2009 | Tung et al. |
| 2009/0186363 A1 | 7/2009 | Ashkenazi et al. |
| 2009/0186409 A1 | 7/2009 | Frantz et al. |
| 2009/0191199 A1 | 7/2009 | Kanda et al. |
| 2009/0191592 A1 | 7/2009 | Kanda et al. |
| 2009/0203132 A1 | 8/2009 | Swayze et al. |
| 2009/0203896 A1 | 8/2009 | Bhat et al. |
| 2009/0209629 A1 | 8/2009 | Mirkin et al. |
| 2009/0221095 A1 | 9/2009 | Mirkin et al. |
| 2009/0221685 A1 | 9/2009 | Esau et al. |
| 2009/0228994 A1 | 9/2009 | Kanda et al. |
| 2009/0238811 A1 | 9/2009 | McDaniel et al. |
| 2009/0246129 A1 | 10/2009 | Cairns et al. |
| 2009/0258931 A1 | 10/2009 | Monia et al. |
| 2009/0286969 A1 | 11/2009 | Esau et al. |
| 2009/0291906 A1 | 11/2009 | Esau et al. |
| 2009/0291907 A1 | 11/2009 | Esau et al. |
| 2009/0297531 A1 | 12/2009 | Carins et al. |
| 2009/0298174 A1 | 12/2009 | Esau et al. |
| 2009/0298910 A1 | 12/2009 | Griffey et al. |
| 2009/0311259 A1 | 12/2009 | Smith |
| 2009/0317907 A1 | 12/2009 | Esau et al. |
| 2009/0324490 A1 | 12/2009 | Cairns et al. |
| 2009/0324592 A1 | 12/2009 | Cairns et al. |
| 2010/0028337 A1 | 2/2010 | Kong-Beltran et al. |
| 2010/0028559 A1 | 2/2010 | Yan et al. |
| 2010/0061996 A1 | 3/2010 | Kirchhofer et al. |
| 2010/0076183 A1 | 3/2010 | Dellinger et al. |
| 2010/0080809 A1 | 4/2010 | Collins et al. |
| 2010/0092997 A1 | 4/2010 | Nakamura et al. |
| 2010/0113350 A1 | 5/2010 | Fan et al. |
| 2010/0113523 A1 | 5/2010 | Alberte et al. |
| 2010/0113608 A1 | 5/2010 | Alberte et al. |
| 2010/0129808 A1 | 5/2010 | Mirkin et al. |
| 2010/0136682 A1 | 6/2010 | Mirkin et al. |
| 2010/0143388 A1 | 6/2010 | Kanda et al. |
| 2010/0158896 A1 | 6/2010 | Brown et al. |
| 2010/0158914 A1 | 6/2010 | Desnoyers |
| 2010/0162418 A1 | 6/2010 | Kanda et al. |
| 2010/0172882 A1 | 7/2010 | Glazer et al. |
| 2010/0173285 A1 | 7/2010 | Varmus et al. |
| 2010/0184844 A1 | 7/2010 | Mirkin et al. |
| 2010/0209956 A1 | 8/2010 | Kirchhofer et al. |
| 2010/0210745 A1 | 8/2010 | McDaniel et al. |
| 2010/0216982 A1 | 8/2010 | Allerson et al. |
| 2010/0233146 A1 | 9/2010 | McDaniel |
| 2010/0233270 A1 | 9/2010 | Mirkin et al. |
| 2010/0234579 A1 | 9/2010 | Mirkin et al. |
| 2010/0240738 A1 | 9/2010 | Dobie et al. |
| 2010/0247430 A1 | 9/2010 | Chan et al. |
| 2010/0249215 A1 | 9/2010 | Lollo et al. |
| 2010/0256038 A1 | 10/2010 | Curnock |
| 2010/0267813 A1 | 10/2010 | Esau et al. |
| 2010/0303834 A1 | 12/2010 | Cairns et al. |
| 2010/0311050 A1 | 12/2010 | Cairns et al. |
| 2010/0322897 A1 | 12/2010 | Kolls et al. |
| 2011/0009600 A1 | 1/2011 | Shitara et al. |
| 2011/0027271 A1 | 2/2011 | Kanda et al. |
| 2011/0033451 A1 | 2/2011 | Carreno et al. |
| 2011/0038849 A1 | 2/2011 | Xie et al. |
| 2011/0042260 A1 | 2/2011 | Crowley et al. |
| 2011/0045005 A1 | 2/2011 | Crowley et al. |
| 2011/0052610 A1 | 3/2011 | Kanda et al. |
| 2011/0054003 A1 | 3/2011 | Karras |
| 2011/0059115 A1 | 3/2011 | Kanda et al. |
| 2011/0070243 A1 | 3/2011 | Crowley et al. |
| 2011/0124591 A1 | 5/2011 | Bennett |
| 2011/0129457 A1 | 6/2011 | Bosanac et al. |
| 2011/0137016 A1 | 6/2011 | Dennis et al. |
| 2011/0171176 A1 | 7/2011 | Baas et al. |
| 2011/0171287 A1 | 7/2011 | Saarma et al. |
| 2011/0177103 A1 | 7/2011 | Dennis et al. |
| 2011/0178157 A1 | 7/2011 | Jin et al. |
| 2011/0206658 A1 | 8/2011 | Crowley et al. |
| 2011/0206702 A1 | 8/2011 | Polakis et al. |
| 2011/0224277 A1 | 9/2011 | Esau et al. |
| 2011/0236374 A1 | 9/2011 | Shitara et al. |
| 2011/0237522 A1 | 9/2011 | Khvorova et al. |
| 2011/0240064 A1 | 10/2011 | Wales et al. |
| 2011/0250626 A1 | 10/2011 | Williams et al. |
| 2011/0250643 A1 | 10/2011 | Kanda et al. |
| 2011/0251258 A1 | 10/2011 | Samarsky et al. |
| 2011/0262406 A1 | 10/2011 | del Campo et al. |
| 2011/0263514 A1 | 10/2011 | Rana |
| 2011/0268657 A1 | 11/2011 | Chang et al. |
| 2011/0268810 A1 | 11/2011 | Saltzman et al. |
| 2011/0274690 A1 | 11/2011 | Dowd et al. |
| 2011/0293585 A1 | 12/2011 | del Campo et al. |
| 2012/0009193 A1 | 1/2012 | Brown et al. |
| 2012/0010387 A1 | 1/2012 | Niwa et al. |
| 2012/0022238 A1 | 1/2012 | Shitara et al. |
| 2012/0029049 A1 | 2/2012 | Bennett et al. |
| 2012/0035248 A9 | 2/2012 | Bennett et al. |
| 2012/0039893 A1 | 2/2012 | de Sauvage |
| 2012/0052110 A1 | 3/2012 | Tomic et al. |
| 2012/0059046 A1 | 3/2012 | Woolf et al. |
| 2012/0077201 A1 | 3/2012 | Varmus et al. |
| 2012/0097194 A1 | 4/2012 | McDaniel et al. |
| 2012/0114673 A1 | 5/2012 | Dennis et al. |
| 2012/0115136 A1 | 5/2012 | Buchardt et al. |
| 2012/0115228 A1 | 5/2012 | Esau et al. |
| 2012/0122216 A1 | 5/2012 | Esau et al. |
| 2012/0142754 A1 | 6/2012 | Niitsu et al. |
| 2012/0156138 A1 | 6/2012 | Smith |
| 2012/0157514 A1 | 6/2012 | Esau et al. |
| 2012/0171279 A1 | 7/2012 | Karelson et al. |
| 2012/0184724 A1 | 7/2012 | Sierzchala et al. |
| 2012/0202874 A1 | 8/2012 | Karras |
| 2012/0244230 A1 | 9/2012 | Mirkin et al. |
| 2012/0269730 A1 | 10/2012 | Mirkin et al. |

OTHER PUBLICATIONS

P. Gupta, O. Muse, E. Rozners, "Recognition of double-stranded RNA by guanidine-modified peptide nucleic acids", *Biochemistry* 2012, 51, 63-73.

Zengeya T, Gupta P, Rozners E., "Triple-helical recognition of RNA using 2-aminopyridine-modified PNA at physiologically relevant conditions", Angew Chem Int Ed Engl. Dec. 7, 2012;51(50):12593-6. doi: 10.1002/anie.201207925. Epub Nov. 4, 2012.(1).

Shields, George C., Charles A. Laughton, and Modesto Orozco. "Molecular Dynamics Simulations of the d (T⊙ A⊙ T) Triple Helix." *Journal of the American Chemical Society* 119.32 (1997): 7463-7469.

Gowers, Darren M., and Keith R. Fox. "Towards mixed sequence recognition by triple helix formation." *Nucleic acids research* 27.7 (1999): 1569-1577.

Uhlmann, Eugen, et al. "PNA: synthetic polyamide nucleic acids with unusual binding properties." *Angewandte Chemie International Edition* 37.20 (1998): 2796-2823.

\* cited by examiner

US 10,260,089 B2

COMPOSITIONS AND METHODS FOR RECOGNITION OF RNA USING TRIPLE HELICAL PEPTIDE NUCLEIC ACIDS

CROSS REFERENCE TO RELATED APPLICATION

The present application is a non-provisional of, and claims benefit of priority under 35 U.S.C. § 119(e) from U.S. Provisional Patent Application Ser. No. 61/719,691, filed Oct. 29, 2012, the entirety of which is expressly incorporated herein by reference in its entirety.

GOVERNMENT SUPPORT

This invention was made with Government support under GM071461 and R01 NS049335 awarded by the National Institutes of Health. The Government has certain rights in this invention.

BACKGROUND OF THE INVENTION

Compared to DNA, molecular recognition of double stranded RNA has received relatively little attention. Until the early 90's, RNA was viewed as a passive messenger in the transfer of genetic information from DNA to proteins. However, since the discovery that RNA can catalyze chemical reactions, the number and variety of non-coding RNAs and the important roles they play in biology have been growing steadily.[1] Currently, the functional importance of most RNA transcripts is still unknown and likely that many more regulatory RNAs will be discovered in the near future. The ability to selectively recognize and control the function of such RNAs will be highly useful for both fundamental research and practical applications. However, recognition of double helical RNA by sequence selective ligand binding is a formidable challenge.[2, 3]

Double-helical RNA has become an attractive target for molecular recognition because many noncoding RNAs play important roles in the control of gene expression. Recently, short peptide nucleic acids (PNA) were found to bind strongly and sequence selectively to a homopurine tract of double-helical RNA via formation of a triple helix. Molecular recognition of RNA can be enhanced by α-guanidine modification of PNA. Ly and coworkers noted that guanidine modification greatly enhances the cellular delivery of PNA. Isothermal titration calorimetry showed that the guanidine-modified PNA (GPNA) had reduced affinity and sequence selectivity for triple-helical recognition of RNA. The data suggested that in contrast to unmodified PNA, which formed a 1:1 PNA-RNA triple helix, GPNA preferred a 2:1 GPNA-RNA triplex invasion complex. Nevertheless, promising results were obtained for recognition of biologically relevant double-helical RNA. Consistent with enhanced strand invasion ability, GPNA derived from D-arginine recognized the transactivation response element of HIV-1 with high affinity and sequence selectivity, presumably via Watson-Crick duplex formation. On the other hand, strong and sequence selective triple helices were formed by unmodified and nucelobase-modified PNA and the purine-rich strand of the bacterial A-site. These results suggest that appropriate chemical modifications of PNA may enhance molecular recognition of complex noncoding RNAs.

Biologically relevant double helical RNAs may be recognized by major groove triple helix formation using peptide nucleic acid (PNA).[4-6] PNAs as short as hexamers form stable and sequence selective Hoogsteen triple helices with RNA duplexes ($K_a > 10^7$ $M^{-1}$) at pH 5.5.[4] A limitation of triple helical recognition was the requirement for long homopurine tracts, as only the Hoogsteen T(U)*A-T(U) and C+*GC triplets could be used (FIG. 1). Modification of PNA with 2-pyrimidinone[7] and 3-oxo-2,3-dihydropyridazine (E)[8] nucleobases allowed efficient and selective recognition of isolated C-G and U-A inversions, respectively, in polypurine tracts of double helical RNA at pH 6.25.[5, 6] However, the high affinity of PNA at pH 5.5 was greatly reduced at pH 6.25 and no binding could be observed at physiologically relevant salt and pH 7.4.[5] The remaining problem was the unfavorable protonation of cytosine, which was required for formation of the Hoogsteen C+*G-C triplets (FIG. 1). Because its $pK_a$=4.5, cytosine is hardly protonated under physiological pH, which greatly decreases the stability of the triple helix.

Povsic and Dervan pioneered the chemical modulation of the cytosine pKa by showing that triple helices containing 5-methylcytosine were more stable at higher pH than those of unmodified DNA.[10] More recently, derivatives of 2-aminopyridine have been used to increase the stability of DNA triple helices at high pH. [11-14]

An alternative approach has used neutral nucleobases that mimic the hydrogen-bonding scheme of protonated cytosine. The most notable examples are pseudoisocytosine (abbreviated as J in FIG. 1) by Kan and co-workers,[15] methyloxocytosine by McLaughlin and co-workers,[16, 17] and a pyrazine derivative by von Krosigk and Benner.[18] The J base is widely used in PNA to alleviate the pH dependency of PNA-DNA triplexes.[19, 20]

Practical applications of triple-helical recognition of nucleic acids are limited by (1) the low stability and slow formation of the triplex caused, at least in part, by electrostatic repulsion between the negatively charged phosphate backbones of the double helix and the incoming third-strand oligonucleotide and (2) the requirement for long homopurine tracts, as only U*A-U and C*G-C triplets are used in the common triple-helical recognition. However, it was recently shown that short peptide nucleic acids (PNA) recognize double-helical RNA via highly stable and sequence selective triple-helix formation.[4-5] PNA, as short as hexamers, formed triple helices with a RNA duplex faster and with higher affinity than with RNA as the third strand. Furthermore, nucleobase modifications allowed recognition of isolated pyrimidine inversions in short polypurine tracts, thus expanding the potential of recognition to biologically relevant double-helical RNA, such as rRNA and microRNAs. [5]

SUMMARY OF THE INVENTION

These findings inspired a hypothesis that, because of the absence of a negatively charged backbone, PNA will be a superior candidate for triple-helical recognition of RNA and may overcome the limitations of natural oligonucleotides in triple-helical recognition. Interestingly, despite extensive studies of DNA-PNA triplexes, binding of PNA to double-helical RNA had not been previously studied. The potential of chemically modified PNA in molecular recognition of double-helical RNA was therefore explored. The use of modified heterocycles to recognize double stranded RNA at physiologically relevant conditions also had not been studied.

The present invention provides an efficient solution to the binding problem and demonstrates that sequence selective recognition of the RNA duplex can be achieved at physiologically relevant conditions by replacing cytosine with a more basic ($pK_a$=6.7 [9]) heterocycle, 2-aminopyridine (abbreviated as M in FIG. 1).

Despite the excellent chemical and biophysical properties, in vivo applications of unmodified PNA have been limited because of poor uptake by mammalian cells. Recent work on chemically modified PNA showed that the cellular delivery may be enhanced by attaching cationic cell-penetrating peptides. Ly and co-workers developed guanidine-modified PNA (GPNA, the backbone derived from arginine instead of glycine) that maintained strong and sequence selective binding to complementary single-stranded DNA and RNA and were efficiently taken up by several cell lines. The enhanced cellular uptake was attributed to the positively charged guanidine groups. The present inventors sought to probe the potential of GPNA in molecular recognition of double-helical RNA. Combining the observed high affinity and sequence selectivity of the PNA-RNA triplex, with the cellular penetration of GPNA permits in vivo applications of sequence selective recognition of double-helical RNA.

M modification was found to be a more efficient approach than using the neutral J base, which is unexpected based on the published literature. The highly charged cationic M-modified PNAs unexpectedly have excellent sequence selectivity, in spite of its positive charges, which would be expected to enhance binding affinity but at the expense of decreased selectivity. Highly charged compounds are expected to be strong and promiscuous (not selective) binders. For example, attachment of the cationic guanidine group decreases the sequence selectivity of GPNA, as reported in Example 3, below.[6] M-modified PNAs exhibit unique RNA selectivity and had two orders of magnitude higher affinity for the double stranded RNAs than for the same DNA sequences. Further, M-modification enhances cellular uptake (see Example 2 [98]), even though M is only partially protonated on the cell surface.

It is an object to provide a peptide nucleic acid (PNA), comprising 2-aminopyridine nucleobases replacing cytosines in a PNA sequence, configured to form stable and sequence selective triple helices with double stranded RNA at physiological conditions, e.g., pH 7.4 and/or 37° C.

It is also an object to provide a method of forming a PNA-dsRNA triple helix which is stable at physiological conditions, e.g., pH 7.4 and/or 37° C., comprising replacing at least one cytosine of the PNA with a 2-aminopyidine nucleobase.

Other objects will become apparent from a review of the description herein.

BRIEF DESCRIPTION OF THE DRAWINGS

FIG. 12A shows parallel triple helix (amino end of PNA aligned with the 5' end of RNA), FIG. 12B shows antiparallel triple helix, and FIG. 12C shows strand invasion triplex that combines antiparallel PNA binding via Watson-Crick hydrogen bonds and parallel PNA binding via Hoogsteen hydrogen bonds;

FIG. 13A shows CD spectra of D-GPNA1, L-GPNA1, and HRP1; FIG. 13B shows binding of D-GPNA1 to HRP1; and FIG. 13C shows binding of L-GPNA1 to HRP1; the •-labeled lines in FIGS. 13B and 13C are the arithmetic difference between the complex spectra (GPNA+HRP1, ♦ and ▲ in FIGS. 13B and 13C, respectively) minus the sum of GPNA (♦ and • in FIG. 13A) and HRP1 (★) spectra; the RNA concentration was 5.25 μM, and the GPNA concentration was 24 μM;

DESCRIPTION OF THE PREFERRED EMBODIMENTS

Example 1

Figure 1:
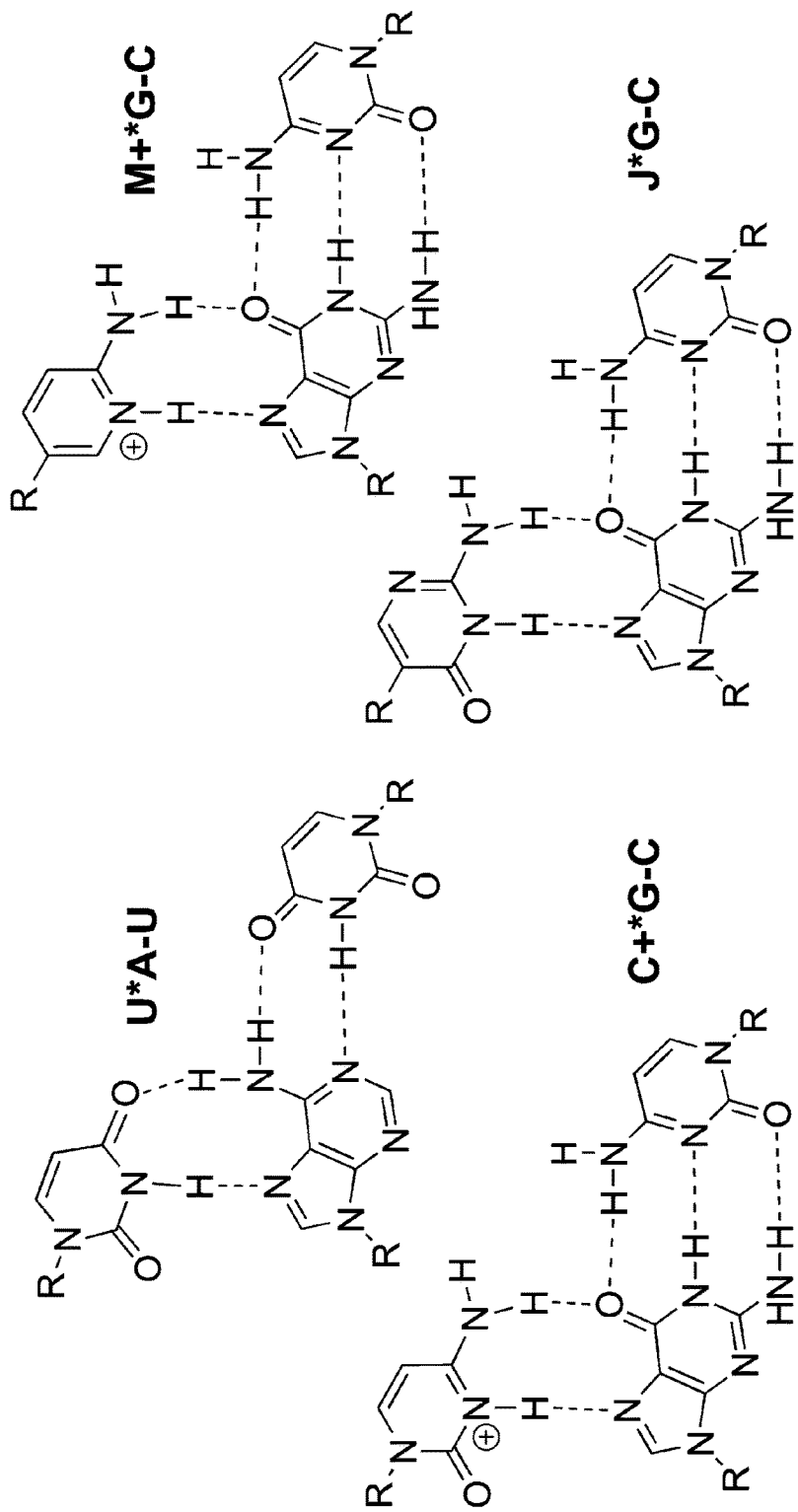
FIG. 1 shows standard and modified Hoogsteen triplets.

The binding of unmodified PNA1, J modified PNA2 and M-modified PNA3 were compared to HRPA (FIG. 2), an A-rich RNA hairpin similar to the model systems used previously.[4, 5] See [29]. Fmoc-protected J monomer 1 was synthesized according to the literature procedure.[21] The M monomer 2 was synthesized from Fmoc-protected PNA backbone 3 and the known carboxylic acid 4 using DCC mediated coupling followed by deprotection of the allyl group as previously described (Scheme 1).[5] All PNAs were synthesized using a standard PNA protocol on an Expedite 8909 DNA synthesizer, purified by HPLC and characterized by mass spectroscopy as previously reported. [4-6, 29]

Scheme 1

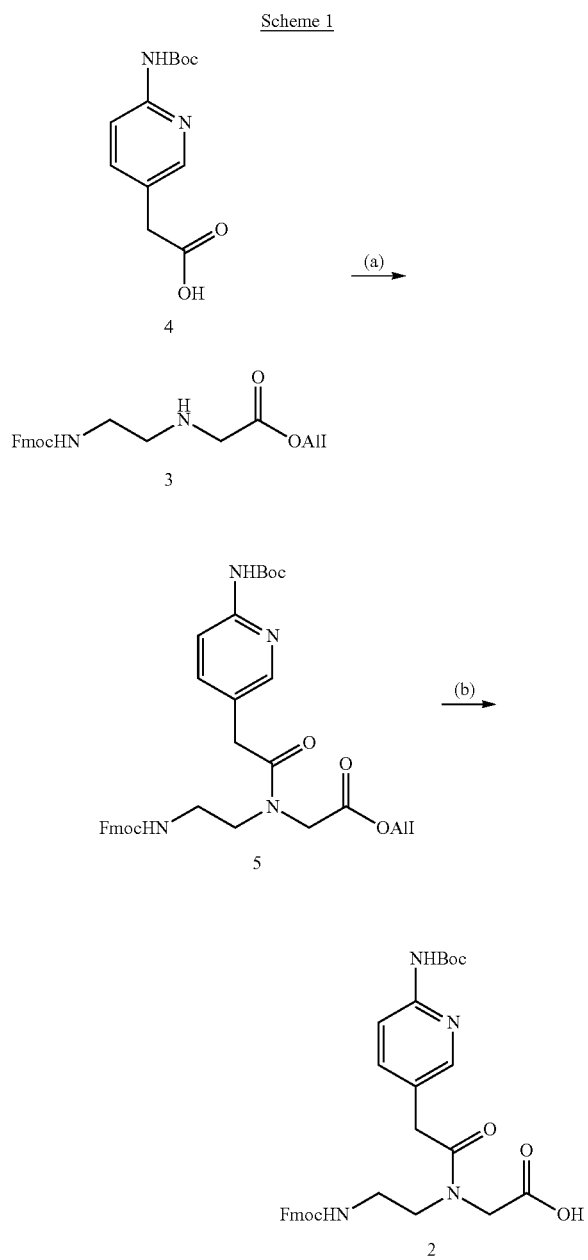

Synthesis of M PNA Monomer:

a) DCC, 3-hydroxy-1,2,3-benzotriazin-4(3H)-one, DMF, RT, overnight, 57%;

b) [Pd(PPh3) 4], N ethylaniline, THF, RT, 2 h, 79%.

Following the same approach as in our previous studies, [4-6] isothermal titration calorimetry (ITC) and UV thermal melting were used to characterize the binding of PNA to RNA hairpins. ITC directly measures the enthalpy of binding and, through fitting of the binding data, provides binding affinity (association constant $K_a$ in $M^{-1}$) and stoichiometry (the ratio of PNA to RNA in the final complex).[22] Due to operational simplicity, reliability and rich thermodynamic data, ITC is one of the best methods to study ligand binding to RNA. The unmodified PNA1 formed a stable triplex with HRPA at pH 5.5 (Table 1) in sodium acetate buffer at 25° C.

TABLE 1

Binding of C, J and M containing PNA to RNA HRPA.[a]

| PNA | Acetate pH 5.5 [b] | Acetate pH 7.0 [b] | Phosphate pH 7.4 [c] |
|---|---|---|---|
| PNA1 (C) | 0.76 | 0.06 | NB |
| PNA2 (J) | — | 0.41 | 0.17 |
| PNA3 (M) | — | 36.5 | 1.8 |

[a] Association constants $K_a \times 10^7$ $M^{-1}$, NB—no binding, $K_a < 10^3$
[b] 100 mM sodium acetate buffer, pH 5.5 at 25° C.
[c] 2 mM $MgCl_2$, 90-mM KCl, 10 mM NaCl, 50 mM potassium phosphate at 37° C.

As expected, because of the unfavorable protonation of cytosine at higher pH, the affinity decreased significantly when the pH of the buffer was increased to 7 and no binding in phosphate buffer mimicking the physiological conditions at 37° C. was observed.

The affinity of PNA1 at pH 5.5 was used as a benchmark to gauge the effect of J and M modifications on PNA affinity at higher pH. The affinity of J-modified PNA2 for HRPA in acetate buffer at pH 7 was lower than the affinity of PNA1 at pH 5.5 and decreased even more under the more demanding physiological conditions (Table 1). Nielsen and co-workers [20] reported that the affinity of an unmodified PNA 15mer (having 5 isolated cytosines) for a DNA duplex dropped by three orders of magnitude ($K_d$ changed from 2 nM to 2.2 mM) when changing the pH from 5.5 to 7.2. Substitution of all five cytosines by J base increased the affinity only about tenfold ($K_d$=0.15 mM).[20] Thus, this result was qualitatively consistent with that reported by Nielsen, only smaller in magnitude, and suggested that the positive charge on cytosine contributed significantly to stability of the Hoogsteen triplet, presumably via electrostatic attraction to the negatively charged nucleic acid. Consequently, an ideal design for recognition of G-C pairs would include both a correct hydrogen bonding scheme and a positive charge on the heterocycle. Because unmodified PNA containing cytosine (pKa=4.5) forms a stable triple helix at pH 5.5, PNA modified with 2-aminopyridine M (pKa=6.7) was hypothesized to form at least equally strong triple helices at physiological pH 7.4 (due to a similar pH/pKa difference).

Figure 2:
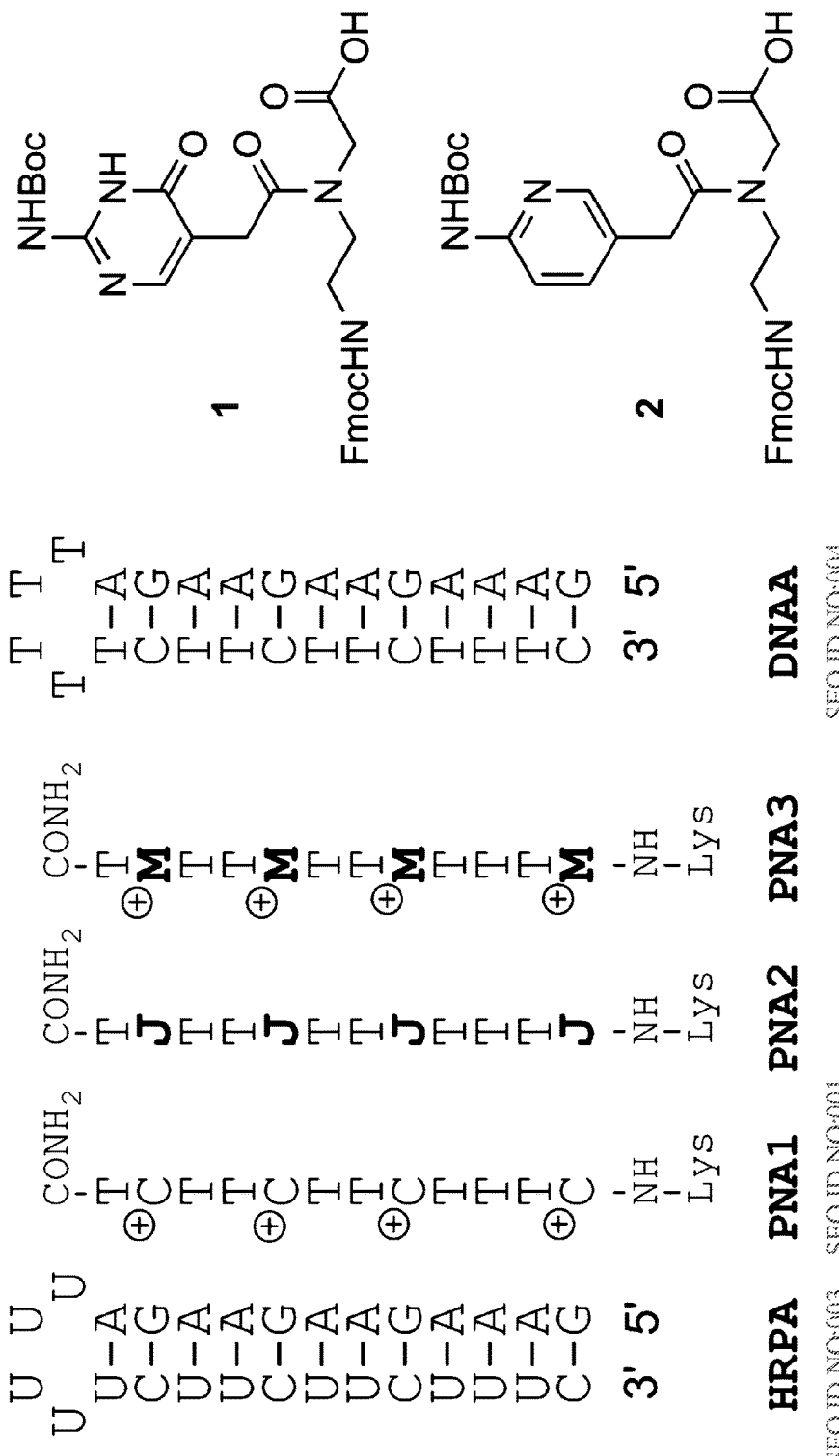
FIG. 2 shows RNA, PNA, and DNA sequences used to compare C, J, and M nucleobases.

Confirming this hypothesis isothermal titration calorimetry (ITC) showed that M modification strongly enhanced the binding affinity of PNA3. In acetate buffer at pH 7 M-modified PNA3 had about two orders of magnitude higher affinity ($K_a$=3.7×10$^8$) for HRPA than the J-modified PNA2 (FIG. 2 and Table 1). Under physiologically relevant conditions PNA3 bound to HRPA with $K_a$=1.8×10$^7$, which was an order of magnitude higher than the affinity of PNA2 at the same conditions and twice that of unmodified PNA1 at pH 5.5. The larger drop in affinity for PNA3 compared to PNA2 going from acetate to phosphate buffer is most likely due to screening of the electrostatic interactions (that are more important for the charged M) by higher salt concentration and the presence of $MgCl_2$ in the physiologically relevant buffer. Most remarkably, binding of PNA3 to the matched DNA hairpin (DNAA) in physiological phosphate buffer was about two orders of magnitude weaker ($K_a$=3×10$^5$) than binding to RNA HRPA. This result suggested that the M-modified PNA might have unique selectivity for triple helical recognition of RNA over DNA. For all experiments at physiologically relevant conditions, fitting of ITC titration curves gave a 1:1 PNA:RNA stoichiometry (see Table 2) consistent with the triple helix formation.

TABLE 2

Experimental ITC data.

| | Sequence | Ka | ΔH | ΔS | ΔG | Stoichiom. |
|---|---|---|---|---|---|---|
| HRPA | PNA1 (5.5) | 7.58E+06 | −55.7 | −155 | −9.4 | 1.2 |
| | PNA1 (7.0) | 5.65E+05 | −105.1 | −326 | −7.8 | 0.5 |
| | PNA2 (7.0) | 4.10E+06 | −27.9 | −63 | −9.0 | 1.3 |
| | PNA2 (7.4) | 2.20E+06 | −17.9 | −31 | −8.6 | 1.1 |
| | | 1.10E+06 | −14.8 | −22 | −8.2 | 1.1 |
| | average | 1.65E+06 | −16.4 | −27 | −8.4 | 1.1 |
| | standard dev | 7.78E+05 | 2.2 | 6 | 0.3 | 0.0 |
| | PNA3 (7.0) | 4.20E+08 | −64.5 | −177 | −11.8 | 0.9 |
| | | 3.10E+08 | −67.4 | −187 | −11.6 | 0.8 |
| | average | 3.65E+08 | −65.9 | −182 | −11.7 | 0.9 |
| | standard dev | 7.78E+07 | 2.0 | 7 | 0.1 | 0.1 |
| | PNA3 (7.4) | 1.40E+07 | −76.4 | −224 | −9.7 | 0.8 |
| | | 2.10E+07 | −80.3 | −236 | −10.0 | 0.7 |
| | average | 1.75E+07 | −78.3 | −230 | −9.9 | 0.8 |
| | standard dev | 4.95E+06 | 2.7 | 8 | 0.2 | 0.1 |
| DNAA | PNA3 (7.4) | 2.00E+05 | −5.3 | 7 | −7.2 | 1.0 |
| | | 3.70E+05 | −46.8 | −132 | −7.6 | 0.9 |
| | average | 2.85E+05 | −26.0 | −62 | −7.4 | 1.0 |
| | standard dev | 1.20E+05 | 29.4 | 98 | 0.3 | 0.1 |
| HRP1 | PNA5 (7.4) | 1.10E+07 | −46.1 | −122 | −9.6 | 1.0 |
| | | 2.80E+07 | −38.0 | −93 | −10.2 | 1.2 |
| | average | 1.95E+07 | −42.0 | −108 | −9.9 | 1.1 |
| | standard dev | 1.20E+07 | 5.7 | 21 | 0.4 | 0.1 |
| HRP2 | PNA6 (7.4) | 4.18E+06 | −37.7 | −96 | −9.0 | 1.1 |
| | PNA6A (7.4) | 5.00E+05 | −19.6 | −40 | −7.8 | 1.0 |
| HRP7 | PNA7 (7.4) | 1.38E+07 | −103.9 | −316 | −9.7 | 0.7 |
| | | 1.05E+07 | −85.5 | −255 | −9.6 | 1.0 |
| | average | 1.22E+07 | −94.7 | −285 | −9.7 | 0.9 |
| | standard dev | 2.33E+06 | 13.0 | 43 | 0.1 | 0.2 |

UV thermal melting experiments confirmed the ITC results. Consistent with previous observations,[4] the complexes of HRPA and high affinity PNAs melted in one transition of triple helix to single strands without an intermediate duplex. In phosphate buffer at pH 7.4 adding PNA2 had little effect on the stability of HRPA: tm=75° C. for HPRA alone and 74° C. for a 1:1 complex of HRPA-PNA2. Consistent with the higher Ka observed in the ITC experiments, the thermal stability of a 1:1 complex of HRPA-PNA3 was significantly higher at 80° C. Taken together, the results confirmed the hypothesis that the charged M would have an advantage over the neutral J for triple helical recognition of RNA.

Figure 3:
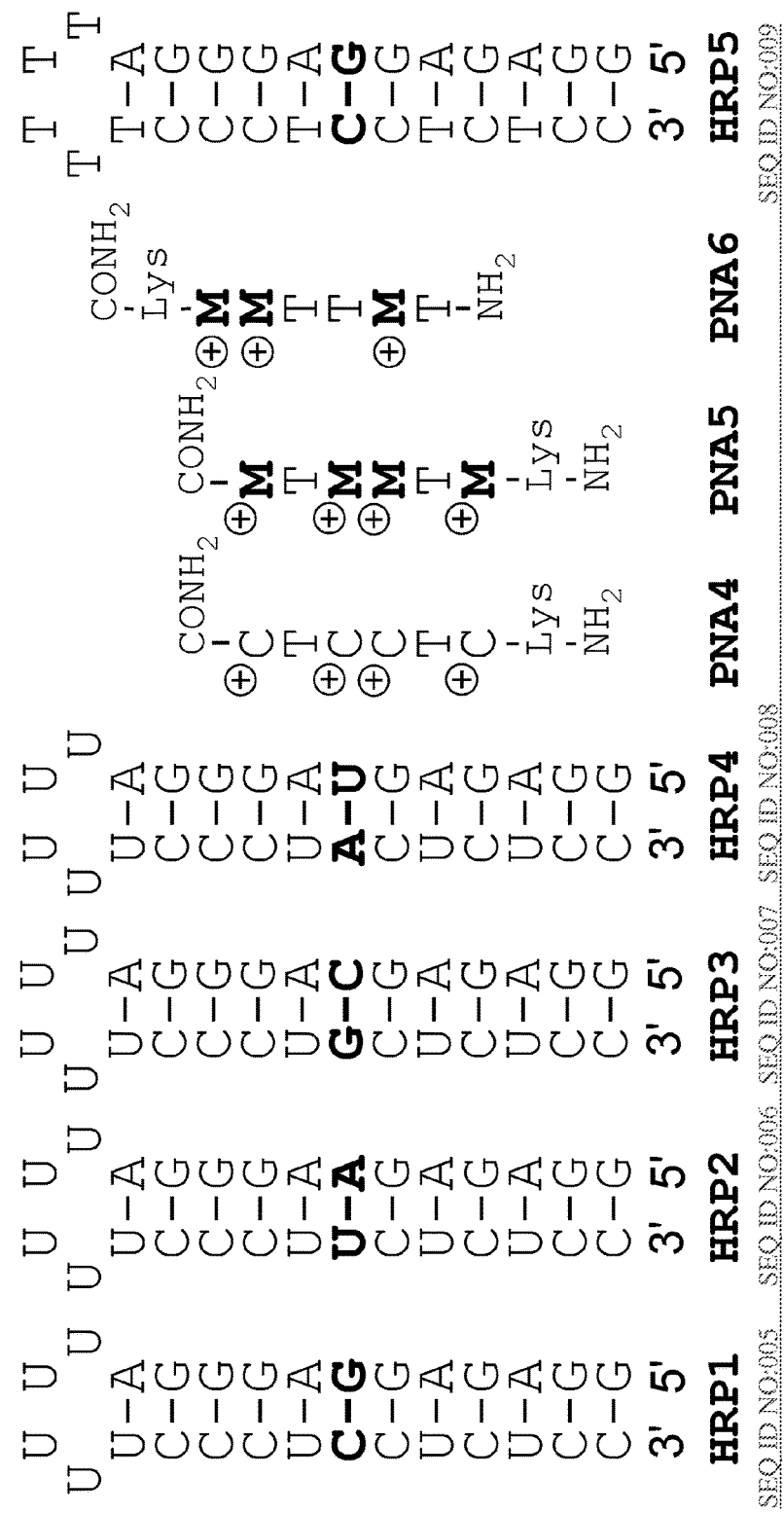
FIG. 3 shows PNA, RNA, and DNA used in the sequence specificity study.

Next the sequence specificity of M-modified PNA was probed using a model system from previous studies (FIG. 3).[4, 5] Table 3 shows that PNA5 (four M modifications) had high affinity for the matched HRP1 at physiologically relevant conditions while maintaining excellent sequence specificity. The binding affinity of M-modified PNA5 at pH 7.4 was somewhat lower than that of unmodified PNA4 at pH 5.5.[4] This was in contrast to a similar comparison of M-modified PNA3 and unmodified PNA1 in Table 1. The discrepancy might be related to electrostatic repulsion of adjacent charged nucleobases, which has been reported to have a negative effect on affinity,[23] and may affect PNA5 more than PNA4. Nevertheless, the strong and highly selective RNA binding by PNA5 at physiologically relevant conditions was extremely encouraging. UV thermal melting of the matched PNA5-HRP1 complex showed a broad and relatively weak transition at ~55° C. that might be assigned to triplex melting preceding the melting of the HRP1 hairpin at ~100° C. Similar transitions unique to the matched PNA5-HRP1 complex were also observed in CD melting plots. Consistent with the high sequence selectivity, no transitions above 30° C. were observed that could be assigned to triplex melting of the mismatched complexes. Confirming the unique RNA selectivity observed for PNA3, PNA5 showed little, if any binding to its matched DNA hairpin HRP5.

TABLE 3

Binding of M-modified PNA to RNA Harpins[a]

| PNA | HRP1 (G-C) | HRP2 (A-U) | HRP3 (C-G) | HRP4 (U-A) |
|---|---|---|---|---|
| PNA4[b] | 8.4 | 0.04 | 0.05 | 0.02 |
| PNA5[c] | 2.0 | <0.001[d] | NB[e] | NB[e] |
| PNA6[c] | NB[e] | 0.4 | NB[e] | NB[e] |

[a]Association constants $K_a \times 10^7$ $M^{-1}$
[b]From ref. 4, in 100 mM sodium acetate buffer, pH 5.5 at 25° C.
[c]In Phosphate buffer, pH 7.4 at 37° C.
[d]Highest estimate, the low binding prevented more accurate curve fit
[e]NB—no binding, $K_a < 10^3$.

PNA6 (three M modifications) had five times lower affinity for the matched HRP2 than PNA5 for HRP1, which was consistent with a higher stability of triplets involving G-C base pairs and the notion that the positive charges are important for high binding affinity. As expected, PNA6 showed excellent sequence specificity. The PNA-RNA stoichiometry was 1:1 in all experiments shown in Table 3 (see Table 2).

Figure 4:
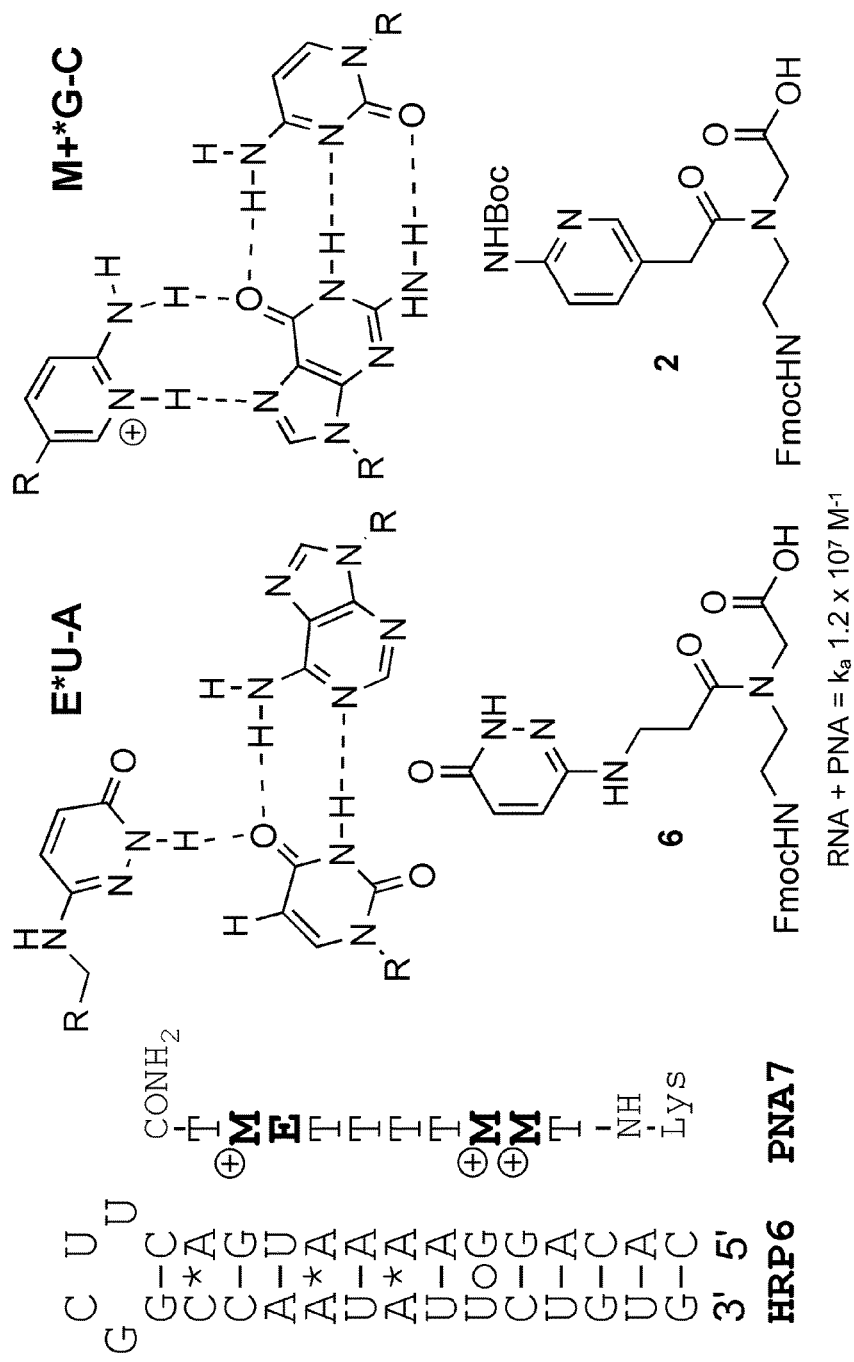
FIG. 4 shows binding of E- and M-modified PNA7 to HRP6 to model the pri-miRNA-215 hairpin structure.

Finally, microRNA-215, which is implicated in cancer development and drug resistance, [24, 25] was selected as an initial target to check if M-modified PNA could bind to biologically relevant double helical RNA. MicroRNAs (miRNAs) are transcribed as long hairpin structures, pri-miRNAs, which are processed into mature miRNA duplexes (~22 nt) by Drosha and Dicer endonucleases. It is common to find stretches of eight and more contiguous purines interrupted by one or two pyrimidines in pri-miRNA hairpins.[26] Triple helical binding to such sites could be used to detect miRNAs and interfere with their function, which would find broad applications in fundamental science, medicine and biotechnology. HRP6 was chosen as a model that contains the purine rich recognition site present in pri-miRNA-215.[26] HRP6 has a stretch of nine purines interrupted by a uridine and features several non-canonical base pairs, which are hallmarks of pri-miRNA hairpins. For recognition of the uridine interruption nucleobase E (FIG. 4) that was originally designed for thymidine recognition in DNA[8] and later adopted for uridine recognition in RNA was used.[5] PNA7 having three M and one E modification was prepared using monomers 2 and the previously reported [5] 6 (FIG. 4).

Consistent with results obtained with other M-modified PNAs, PNA7 recognized HRP6 with high affinity (Ka=1.2× $10^7$) and 1:1 stoichiometry (Table 2) under physiologically relevant conditions. Remarkably, the non-canonical C*A and A*A and the wobble UoG base pairs did not prevent formation of the PNA-RNA complex.

In summary, modification of PNA with 2-aminopyridine (M) nucleobases has been demonstrated to allow formation of stable and sequence selective triple helices with double stranded RNA at physiologically relevant conditions. For triple helical RNA recognition, modulation of nucleobase basicity (c.f., pKa=6.7 for M with 4.5 for C) was a more efficient approach than using the neutral J base. The M-modified PNAs exhibited unique RNA selectivity and had two orders of magnitude higher affinity for the double stranded RNAs than for the same DNA sequences. It is conceivable that the deep and narrow major groove of RNA presented a better steric fit for the PNA ligands than the wider major groove of DNA. In preliminary experiments nucleobase-modified PNA recognized a purine rich model sequence of a double helical miRNA precursor with high affinity at physiologically relevant conditions. While this is a relatively new area of research, Beal and co-workers[27] have already demonstrated the potential of targeting pri-miRNAs using helix-threading peptides. Taken together the present results suggest that PNA may have unique and previously underappreciated potential for triple helical recognition of biologically relevant RNA. Low stability at pH 7.4 has been a long-standing problem for practical applications of triple helices. The excellent performance of M modified PNAs at pH 7.4 observed herein provide efficient solution to this problem that should open the door for new approaches to detection and interference with the function of double stranded RNA molecules.

Synthesis of (6-tert-butoxycarbonylaminopyridin-3-yl) acetic acid (4).

Ethyl (6-tert-butoxycarbonylaminopyridin-3-yl)acetate [100] (4.4 g, 15.7 mmol) and NaOH (1.3 g, 32.5 mmol) were dissolved in of methanol/water (1:1, 30 mL) and refluxed for 1.5 hours. The solution was cooled and the product was precipitated by adding 20% aqueous citric acid. The precipitate was filtered, washed with dichloromethane/hexanes (1:1, 20 mL) and dried to give 1.4 g of 4 (49%) as pale yellow solid.). $^1$H NMR (DMSO-d6, 600 MHz) δ: 12.54 (s, 1H), 9.72 (s, 1H), 8.12 (s, 1H), 7.75-7.73 (d, 1H), 7.63-7.62 (d, 1H), 3.55 (s, 2H), 1.48 (s, 9H). $^{13}$C NMR (DMSO-d6, 90.5 MHz) δ: 172.4, 152.7, 151.1, 148.1, 138.8, 125.1, 111.9, 79.5, 337.0, 28.1.

Synthesis of allyl 2-(N-(2-(Fmoc)ethyl)-2-(6-(tert-butoxycarbonylamino)pyridin-3-yl)acetamido)acetate (5).

(6-tert-butoxycarbonylaminopyridin-3-yl) acetic acid 4 (0.20 g 0.79 mmol), PNA backbone 3 [78] (0.27 g, 0.72 mmol) and 3-hydroxy-1,2,3-benzotriazin-4(3H)-one (0.13 g, 0.80 mmol) were dissolved in anhydrous dimethylformamide (5 mL). The solution was cooled on ice and N,N'-dicyclohexylcarbodiimide (0.18 g, 0.88 mmol) was added. After 1 hour, the ice bath was removed and the solution was left to stir overnight at room temperature. The reaction mixture was evaporated, dissolved in dichloromethane (16 mL) and washed with 5% aqueous NaHCO$_3$ (2×20 mL). The organic layer was dried over Na$_2$SO$_4$ and evaporated under reduced pressure. The product was purified by silica gel column chromatography using 20-80% of ethyl acetate in hexane to give 0.25 g of 6 (57%). Rf=0.35 (5% v/v of methanol in dichloromethane). $^1$H NMR (DMSO-d6, 600 MHz) δ: 8.02-8.00 (d, 1H), 7.83-7.800 (t, 1H), 7.69-7.67 (d, 2H), 7.56 (s, 1H), 7.51-7.50 (d, 2H), 7.48 (s, 1H), 7.33-31 (d, 2H), 7.24-7.23 (t, 2H), 5.87-5.80 (m, 1H), 5.65-6.34 (t, 1H), 5.29-5.26 (d, 1H), 5.23-5.21 (d, 1H), 5.20-5.18 (d, 1H), 4.59-58 (d, 1H), 4.56-4.55 (d, 1H), 4.36-4.35 (d, 1H), 4.29-4.28 (d, 2H), 4.14-4.12 (t, 1H), 4.04 (s, 1H), 3.96 (s, 2H), 3.55 (s, 2H), 3.51-3.49 (t, 2H), 3.45 (s, 2H), 3.31-3.30 (d, 2H), 3.28-3.28 (d, 2H), 1.43 (s, 9H). $^{13}$C NMR (DMSO-d6, 90.5 MHz) δ: 171.7 (171.3), 169.9, 169.0, 156.6, 152.3, 151.0, 147.8, 143.8, 143.8, 141.3, 139.0, 131.4, 131.1, 127.8, 127.1, 125.1, 125.0, 124.7, 120.0, 120.0, 119.8, 119.1, 112.1, 81.0, 66.9 (66.6), 66.2, 49.6, (49.2), 47.2, 39.5, 37.0, 36.3, 28.3.

Synthesis of 2-(N-(2-(Fmoc)ethyl)-2-(6-(tert-butoxycarbonylamino)pyridin-3-yl)acetamido) acetic acid (2)

2-(N-(2-(Fmoc)ethyl)-2-(6-(tert-butoxycarbonylamino) pyridin-3-yl)acetamido) acetate 5 (0.32 g, 0.52 mmol) was dissolved in anhydrous THF (12 mL). Pd(PPh3)4 (0.025 g, 0.022 mmol) and N-ethylaniline (120 µl, 0.96 mmol) were added and the reaction was stirred for 2 hours. The solvent was evaporated and the yellow residue was dissolved in ethyl acetate (25 ml, gentle warming may be required) and washed with saturated aqueous KHSO$_4$ (3×20 mL), water (3×20 mL) and brine (3×20 mL). The organic layer was dried over Na$_2$SO$_4$ and evaporated under reduced pressure. The product was purified by silica gel column chromatography using ethyl acetate to give 0.24 g of 2 (79%). For best results, compound 2 should be used in PNA synthesis immediately after preparation. $^1$H NMR (DMSO-d6, 360 MHz) δ: 9.95 (s, 1H), 8.02 (d, 1H), 7.72 (s, 1H), 7.65-7.63 (t, 2H), 7.52-7.50 (d, 2H), 7.47-7.45 (d, 1H), 7.23-7.19 (t, 2H), 5.60 (s, 1H), 4.45 (d, 2H), 4.37-4.36 (d, 1H), 4.29-4.27 (d, 1H), 4.12-4.10 (t, 2H), 3.94 (s, 2H), 3.59 (s, 2H), 3.56 (s, 1H), 3.48 (s, 1H) 3.39 (s, 1H), 3.32-3.31 (d, 2H), 3.24 (s, 1H), 1.40 (s, 9H). $^{13}$CNMR (DMSO-d6, 90.5 MHz) δ: 171.0, 156.2, 152.7, 150.6, 148.2, 140.7, 139.5, 138.9, 128.9, 127.5, 127.3, 127.1, 126.5, 125.3, 125.1, 120.1 (120.0), 111.8 (111.8), 79.4 (79.4), 65.6, 46.8, 38.3, 35.8, 28.2 (28.1). HRMS ESI-TOF found m/z 575.2507 [M+H]+, calculated for C$_{31}$H$_{34}$N$_4$O$_7$: 574.2427.

Synthesis of PNA was done on Expedite 8909 synthesizer following the standard manufacturers protocol (2 µmol scale) and using NovaSyn TG Sieber resin (Novabiochem) as a support, HATU as an activator and Fmoc-PNA-A (Bhoc)-OH, Fmoc-PNA-C(Bhoc)-OH, Fmoc-PNA-G (Bhoc)-OH and Fmoc-PNA-T-OH as monomers (purchased from Link Technologies Ltd, UK). L-lysine was coupled to N-terminus of PNA on Expedite 8909 (using standard PNA coupling protocol) using Fmoc-L-lys(Boc)-OH and HATU. Chain extension followed a three-step cycle: (i) removal of the Fmoc-protecting group from the terminal amine with 20% piperidine in DMF, (ii) coupling of the next monomer onto the N-terminus of the growing chain with HATU, and (iii) capping of the unreacted amines with acetic anhydride. Treating the solid resin with m-cresol/TFA (2:8) mixture for 2 h resulted in simultaneous removal of the protecting groups and cleavage of the oligomers from the resin. The crude PNA samples were precipitated from anhydrous ether. The solid was collected, dried, dissolved in HPLC grade water and purified by RP-HPLC on Xbridge Prep C-18 column (5 µm, 10 mm×150 mm) at 60° C. eluting with a linear gradient of acetonitrile in water containing 0.1% of TFA over 40 min. Absorbency was monitored at 254 nm and 280 nm, and the fraction containing the major peak was collected, lyophilized to dryness to afford pure PNA samples. The PNA was quantified following procedure described for DNA and RNA.3 The molecular weight of the synthesized PNAs was confirmed by ESI mass spectrometry:

PNA1. ESI found m/z 3278.7 [M+H]+, calculated for C$_{134}$H$_{180}$N$_{55}$O$_{45}$: 3279.3.

PNA2. ESI found m/z 3279.7 [M+H]+, m/z 1094.5 [M+3H]$^{3+}$, m/z 821.1 [M+4H]$^{4+}$, calculated for C$_{134}$H$_{180}$N$_{55}$O$_{45}$: 3279.3.

PNA3. ESI found m/z 1607.2 [M+2H]$^{2+}$, m/z 1071.4 [M+3H]$^{3+}$, m/z 803.8 [M+4H]$^{4+}$, calculated for C$_{138}$H$_{183}$N$_{51}$O$_{41}$ 3212.3.

PNA5. ESI found m/z 1616.4 [M+H]+, calculated for C$_{72}$H$_{100}$N$_{27}$O$_{17}$: 1615.7.

PNA6. ESI found m/z 1646.6 [M+H]+, calculated for C$_{72}$H$_{100}$N$_{27}$O$_{19}$: 1647.7.

PNA7. ESI found m/z 2710.6 [M+H]+, calculated for C$_{116}$H$_{156}$N$_{44}$O$_{34}$: 2711.8.

RNA was purchased from Dharmacon Inc. and deprotected according to manufacturers recommendations. After deprotection RNA samples were purified using RP-HPLC on Xbridge Prep C-18 column (5 µm, 10 mm×150 mm) at 60° C. eluting with a linear gradient (5%-20%) of mobile phase B in mobile phase A over 40 min, flow rate 5 ml/min. Mobile phase A was 0.1 M of triethylammonium acetate (pH=7.0) in HPLC water and mobile phase B was a mixture of 0.1 M of triethylammonium acetate (pH=7.0) in HPLC water and HPLC grade acetonitrile (60/40, v/v). Absorbency was monitored at a wavelength of 254 nm and 280 nm, and the fraction containing the major peak was collected, lyophilized to dryness to afford pure RNA samples. RNA was quantified using the extinction coefficient provided by Dharmacon.

ITC Experiments were done on a Nano ITC G2 (TA Instruments). RNA stock solution (17.5 µL, 0.24 mM) was evaporated to dryness and the solid was dissolved in 1.6 mL of phosphate buffer (2 mM MgCl2, 90 mM KCl, 10 mM NaCl, 50 mM potassium phosphate at pH 7.4). After degassing, the RNA solution (0.95 mL, 0.002625 mM) was loaded into ITC reaction cell and the reference cell was loaded with degassed HPLC water. PNA stock solution (70 µL, 0.24 mM) was evaporated to dryness and the solid was dissolved in 350 µL of acetate buffer. After degassing the PNA solution (250 µL, 0.048 mM) was loaded in titration syringe. The syringe was inserted into reaction cell and the instrument was equilibrated at 37° C. until the baseline was flat and stable. The following parameters were used:

Experiment type: Incremental titration
Stirring rate=250 rpm
Temperature set point=37° C.
Syringe size=250 µl
Equilibration time=300 sec
Interval of individual injection=260-800 sec
Number of injections=50
Volume of individual injection=5 µl The titration data were analyzed using NanoAnalyze software (TA Instruments) and independent model to obtain the fitting graph and thermodynamic data of the experiments.

UV melting of each RNA (5.25 µM) and PNA (5.25 µM) complexes was done in phosphate buffer (2 mM MgCl$_2$, 90 mM KCl, 10 mM NaCl, 50 mM potassium phosphate at pH 7.4). Absorbance vs. temperature profiles were measured at 260 nm on Shimadzu 800 UV-visible spectrometers equipped with a six or eight position Peltier temperature controllers, respectively. The temperature was increased at a rate of 0.5° C. per minute. The melting temperatures were obtained using Shimadzu LabSolutions Tm Analysis (Version 1.2.1.0) software. The experimental absorbance vs. temperature curves were converted into a fraction of strands remaining hybridized ($\alpha$) vs. temperature curves by fitting the melting profile to a two-state transition model, with linearly sloping lower and upper base lines. The melting temperatures ($t_m$) were obtained directly from the temperature at $\alpha$=0.5.

Example 2

Figure 5:
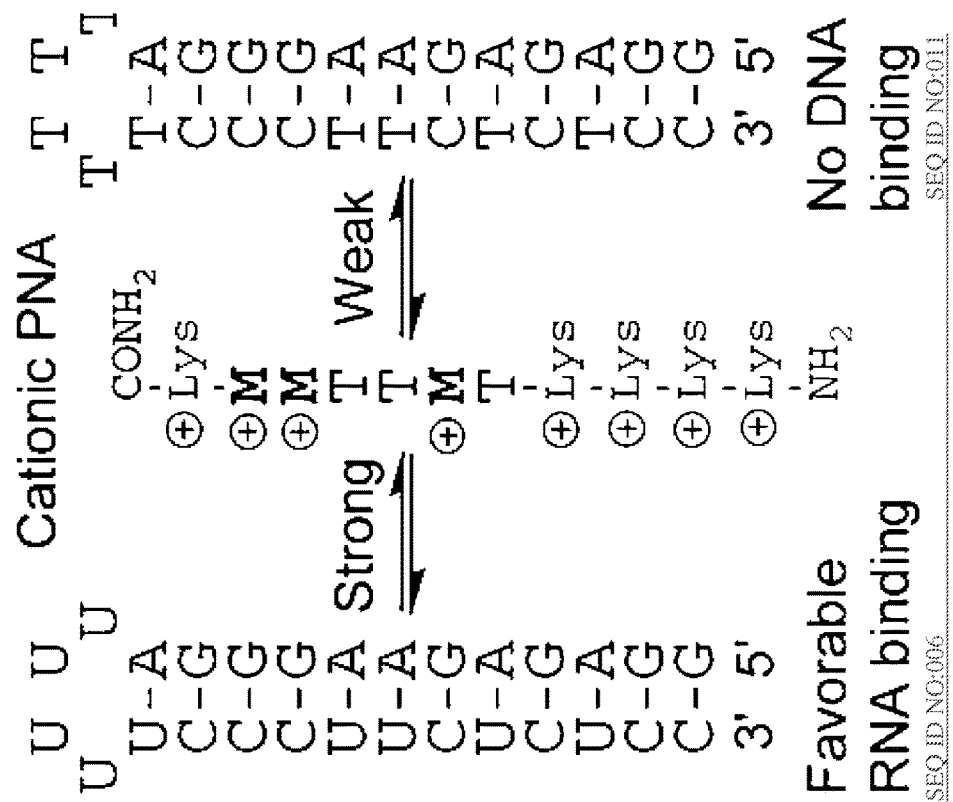
FIG. 5 shows favorable binding of PNA2 to an RNA loop HRP2 but not a DNA loop HRP5.

Conjugation of short peptide nucleic acids (PNA) with tetralysine peptides strongly enhanced triple helical binding to RNA at physiologically relevant conditions.[98] The PNA hexamers and heptamers carrying cationic nucleobase and tetralysine modifications displayed high binding affinity for complementary double-stranded RNA without compromising sequence selectivity. The PNA-peptide conjugates had unique preference for binding double-stranded RNA, while having little, if any, affinity for double-stranded DNA, as represented in FIG. 5. The cationic PNAs were efficiently taken up by HEK293 cells, whereas little uptake was observed for unmodified PNA.

Peptide nucleic acids (PNA) have become important research tools for molecular recognition of double helical DNA.[30] Although PNA-DNA triple helices have been studied in detail,[31] analogous PNA-RNA triplexes were virtually unknown prior to [4-5, 29]. PNA was discovered to form stable and sequence-selective Hoogsteen triple helices with RNA at mildly acidic (pH 5.5) conditions.[4] Isolated pyrimidine interruptions in the purine-rich strand of an RNA duplex could be recognized using nucleobase-modified PNA at pH 6.25.[5] 2-aminopyridine (M, FIG. 1) nucleobase modification enables stable triple helix formation at physiologically relevant pH, salt concentration, and temperature. [29]

Conjugation of a short cationic peptide (Lys4) to M-modified PNA significantly improved RNA binding affinity without compromising sequence selectivity. The doubly modified PNAs had unique selectivity for double-stranded RNA (dsRNA) compared to double-stranded DNA (dsDNA). Furthermore, PNAs carrying M- and Lys-modifications were efficiently taken up by HEK-293 cells, whereas the unmodified PNA showed little uptake.

The groups of Corey [32-34] and Gait [35-36] demonstrated that short oligolysine peptides greatly enhanced the delivery of conjugated PNA in cultured cells. Nielsen and co-workers [31] showed that pseudoisocytidine (J) nucleobase modification and conjugation of PNA with four lysines were both required for full stability of a PNA-DNA triple helix at physiologically relevant conditions.

Interest in testing short oligolysine peptides was further stimulated by a study of Strömberg and co-workers,[37] who showed that addition of cationic peptides to UV melting buffer enhanced the thermal stability of 2'-O-MeRNA/RNA duplexes but had no effect on the stability of DNA/DNA duplexes. It was hypothesized that the stability enhancement was due to the cationic peptides binding selectively in the deep and narrow major groove of RNA but not in the wider major groove of DNA. Since the triple helical binding of PNA also occurs in the major groove of RNA, it was further hypothesized that conjugation of short oligolysine to PNA may significantly increase stability of PNA-RNA triple helices. If these hypotheses were true, the resulting conjugates should be selective ligands for dsRNA, while binding less strongly to dsDNA. This would be an important benefit for potential in vivo applications in addition to the cell permeability In previous studies, it was found that unmodified PNA dodecamers did not bind to double-stranded RNA at physiologically relevant pH. [4-5, 29] Attachment of four additional D-lysines to a PNA hexamer led to detectable binding of PNA1 to dsRNA (FIG. 6 and Table 4) at pH 7.4 and 37° C. in 10 mM sodium phosphate buffer containing 1 mM MgCl2, 50 mM NaCl, and 0.1 mM EDTA. However, PNA1 had no sequence selectivity binding to all four hairpins featuring the variable base pair with approximately equal affinity (Table 4). At a higher salt concentration of the physiologically relevant buffer (2 mM MgCl2, 90 mM KCl, 10 mM NaCl, 50 mM potassium phosphate), pH 7.4, and 37° C., no binding of PNA1 to the matched hairpin HRP2 was observed. These results were consistent with binding being driven by the cationic peptide with relatively little PNA contribution due to unfavorable cytosine protonation. See, Muse, O., Zengeya, T., Mwaura, J., Hnedzko, D., McGee, D., Grewer, C., and Rozners, E. (2013), "Sequence Selective Recognition of Double-Stranded RNA at Physiologically Relevant Conditions Using PNA-Peptide Conjugates: ACS Chemical Biology, 8(8), 1683-1686 & Supplemental Information[98], expressly incorporated herein by reference in its entirety.

Substitution of cytosine with 2-aminopyridine (M) led to sharp increase in binding affinity at physiologically relevant conditions (Table 4); PNA2 bound to the matched HRP2 with an association constant ($K_a$) of $1.7 \times 10^8$ M$^{-1}$. Despite the highly charged nature, PNA2 had very good sequence selectivity. The high affinity was an additive effect of both M and Lys-modifications, as PNA3 lacking the four additional lysines at the amino end had only modest binding affinity for HRP2. This result was confirmed using another PNA sequence, PNA4, which had four lysine modifications at the carboxyl end and targeted a different region in HRP2 (Table 4).

TABLE 4

Binding of M- and Lys-Modified PNA to RNA Targets[a]

| PNA | HRP1 (C-G) | HRP2 (U-A) | HRP3 (G-C) | HRP4 (A-U) |
|---|---|---|---|---|
| PNA1 [b] | 0.34 | 0.19 | 0.31 | 0.03 |
| PNA2 | 0.52 | 16.5 | 0.01 | NB [c] |
| PNA3 [d] | NB [c] | 0.4 | NB [c] | NB [c] |
| PNA4 | 0.23 | 1.8 | 0.06 | |

[a] Association constants $K_a \times 10^7$ M$^{-1}$ in 2 mM MgCl$_2$, 90 mM KCl, 10 mM NaCl, 50 mM potassium phosphate at pH 7.4 and 37° C.
[b] In 10 mM sodium phosphate buffer containing 1 mM MgCl$_2$, 50 mM NaCl and 0.1 mM EDTA at pH 7.4 and 37° C.
[c] NB = no binding, $K_a < 10^3$.
[d] From ref [29].

The RNA targets HRP1-HRP4 were chosen from previous studies, and the lysine-modified PNA could thus be compared with other modified PNAs tested in earlier. [4-5, 29] The sequences of PNA2 and PNA4 were chosen so as to leave sufficient space in the major groove of the relatively short HRP2 for binding of the tetralysine residue. PNA4 has a lower affinity PNA4 compared to that of PNA2, demonstrating sequence dependency and importance of the amino versus carboxyl end lysine modification.

UV and CD thermal melting results were consistent with ITC data. UV melting traces showed relatively weak transitions for triplex dissociation. For the matched triplexes PNA2-HRP2 and PNA4-HRP2, the triplex dissociation overlapped with hairpin melting, giving one transition at around 90° C. (the tm for HRP2 only is 91° C.). Consistent with a relatively higher affinity of PNAs for the mismatched HRP1, the UV melting curves showed weak transitions at 46 (PNA2-HRP1) and 36 (PNA4-HRP1)° C., while other mismatched triplexes had $t_m < 35°$ C. The triplex melting was also observed in temperature-dependent CD spectra that showed characteristic transitions at 230-240 nm and 300-320 nm and melting temperatures similar to those observed in UV experiments. In contrast to UV melting curves, in CD melting plots transitions were observed that could be assigned to triplex dissociation of the matched PNA2-HRP2 and PNA4-HRP2 at around 70° C. The CD melting data were consistent with previous results on PNAs having only M-modifications.[29] Taken together, the results of ITC, UV, and CD experiments confirmed the hypothesis that the cationic M- and Lys modifications would provide mutual and additive stabilization of PNA-RNA triple helices.

Figure 6:
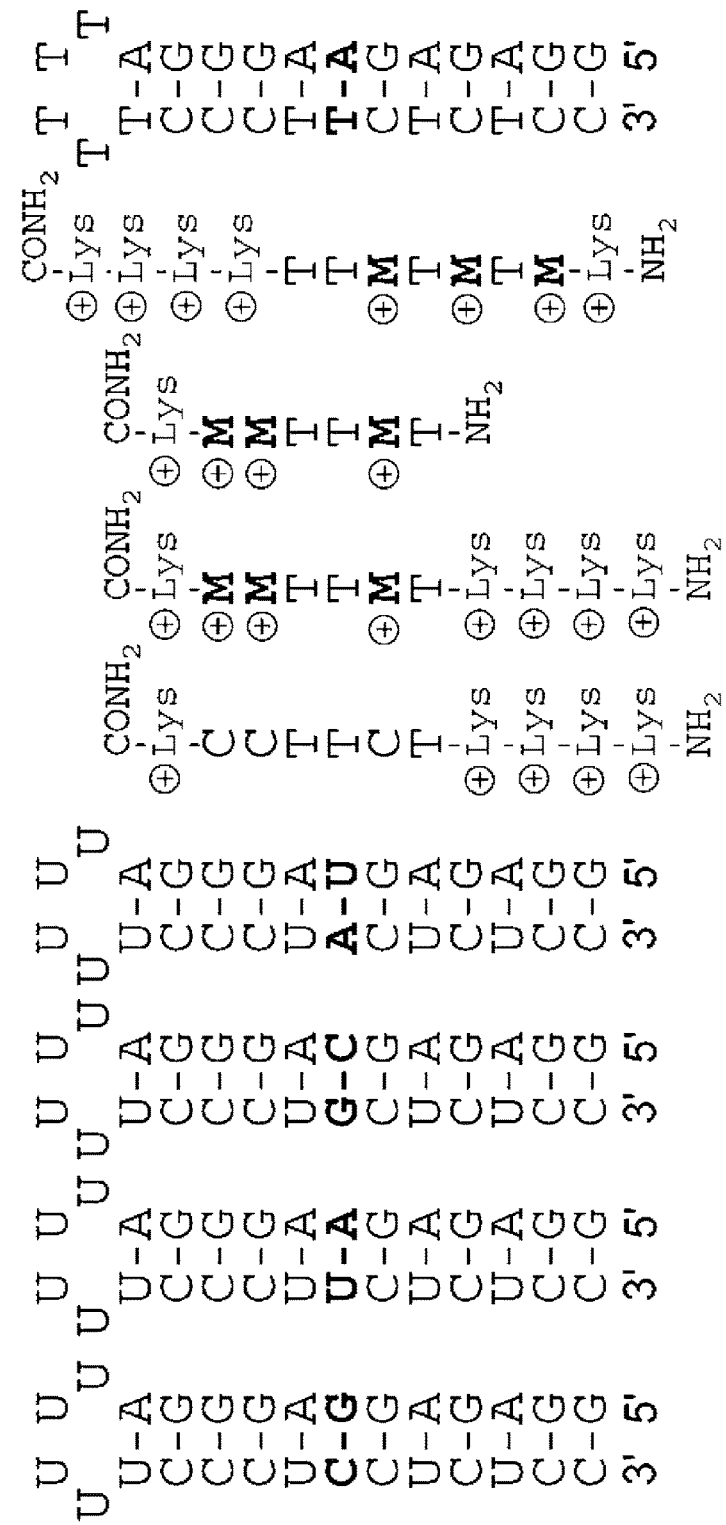
FIG. 6 shows sequences of PNA and RNA and DNA hairpins.

Most remarkably, no binding of either PNA2 or PNA4 to their matched DNA hairpin HRP5 could be detected (FIG. 6). Low affinity of short PNA for dsDNA was consistent with Nielsen's report that strong PNA-DNA triple helices were formed by PNA 15-mers, while no binding could be detected for a PNA 10-mer.[31] Nielsen and co-workers used pseudoisocytosine-(J) and lysine-modified PNA similar to the PNA compounds discussed herein. Thus, the unusually high affinity of PNA hexamer PNA2 and heptamer PNA4 for the matched RNA target HRP2 was the surprising result that provided strong support for the hypothesis that the cationic peptides would bind selectively in the major groove of dsRNA and confer unique RNA selectivity (as compared to the same DNA sequences) on the present PNAs. The high sequence selectivity (mismatch discrimination) and RNA preference of PNA2 and PNA4 becomes especially remarkable if one considers that these PNAs may carry up to eight positive charges when binding to RNA. Such selectivity is in sharp contrast to other cationic RNA binding ligands, e.g., aminoglycosides, which are notoriously promiscuous RNA binders.

While data are unavailable providing insight into the unique RNA selectivity of the present PNAs, it is conceivable that the deep and narrow major groove of RNA presents a better steric fit for the PNA and peptide ligands than the wider major groove of DNA. In support of this notion, Dervan and co-workers [38] recently reported that the DNA minor groove-binding polyamides do not bind in the shallow minor groove of RNA. Taken together, the present results and Dervan's results emphasize that the distinct conformations of dsRNA and dsDNA make the molecular recognition of each of these biopolymers a unique task. Peptide-based ligands have been previously used for molecular recognition of pri-miRNAs by helix-threading peptides [27,28] and TAR RNA of HIV by Tat-derived [99] and, recently, de novo designed branched peptides. [39] While good binding affinity and selectivity was observed, the structural details of peptide binding to dsRNA have not been elucidated.

Poor cellular uptake of unmodified PNA has been a major bottleneck for practical applications.[30,40] Based on the aforementioned results by Corey [32-34] and Gait [35-36], it was envisioned that the cationic nucleobase and lysine modifications, besides enhancing the triple helix stability, might also improve the cellular uptake of PNAs. To obtain a preliminary insight into cellular uptake of our cationic PNAs, a fluorescein-labeled Fl-Lys-(eg1)2-D-Lys-MTETM-MMM-(D-Lys)3 (PNA5, FIG. 7) was prepared, a variant of this sequence without M-modifications (PNA6) and an unmodified PNA7. In these PNAs, eg1 is 2-(2-aminoethoxy) ethoxy acetic acid spacer and E is 3-oxo-2,3-dihydro-pyridazine nucleobase. The E-modification, designed to recognize T-A and U-A interruptions in polypurine tracts [8], was prepared following previously reported procedures.[5]

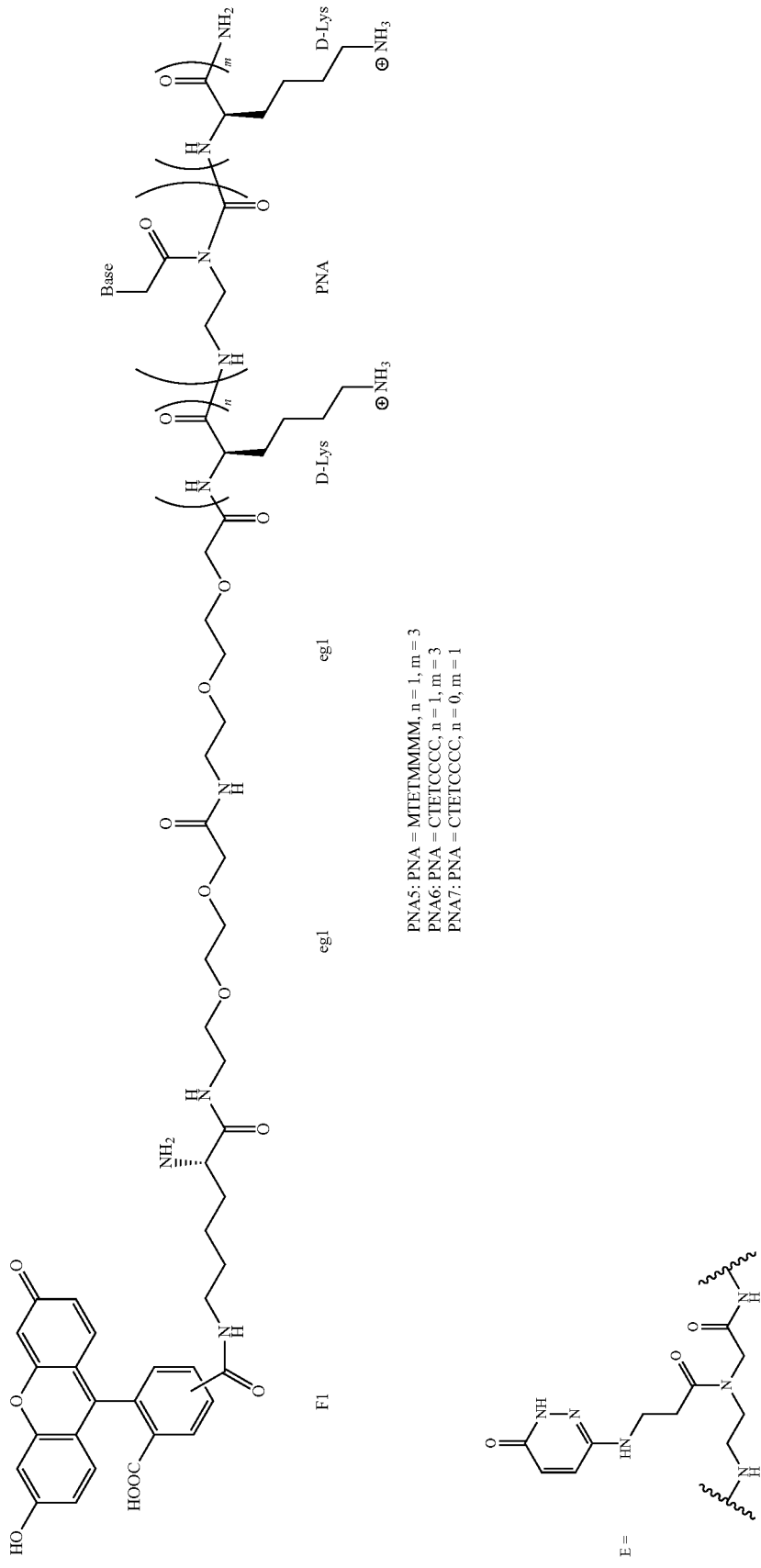

The specific PNA sequence chosen targets a purine-rich tract (modeled in HRP6, FIG. 7) of pri-miRNA-155, an oncogenic microRNA overexpressed in various B-cell cancers.[41] Cellular uptake of PNA5 is a particular step of interest toward exploring potential anticancer effects of pri-miRNA-155 binding by triple helix forming PNA.

Figure 8A:
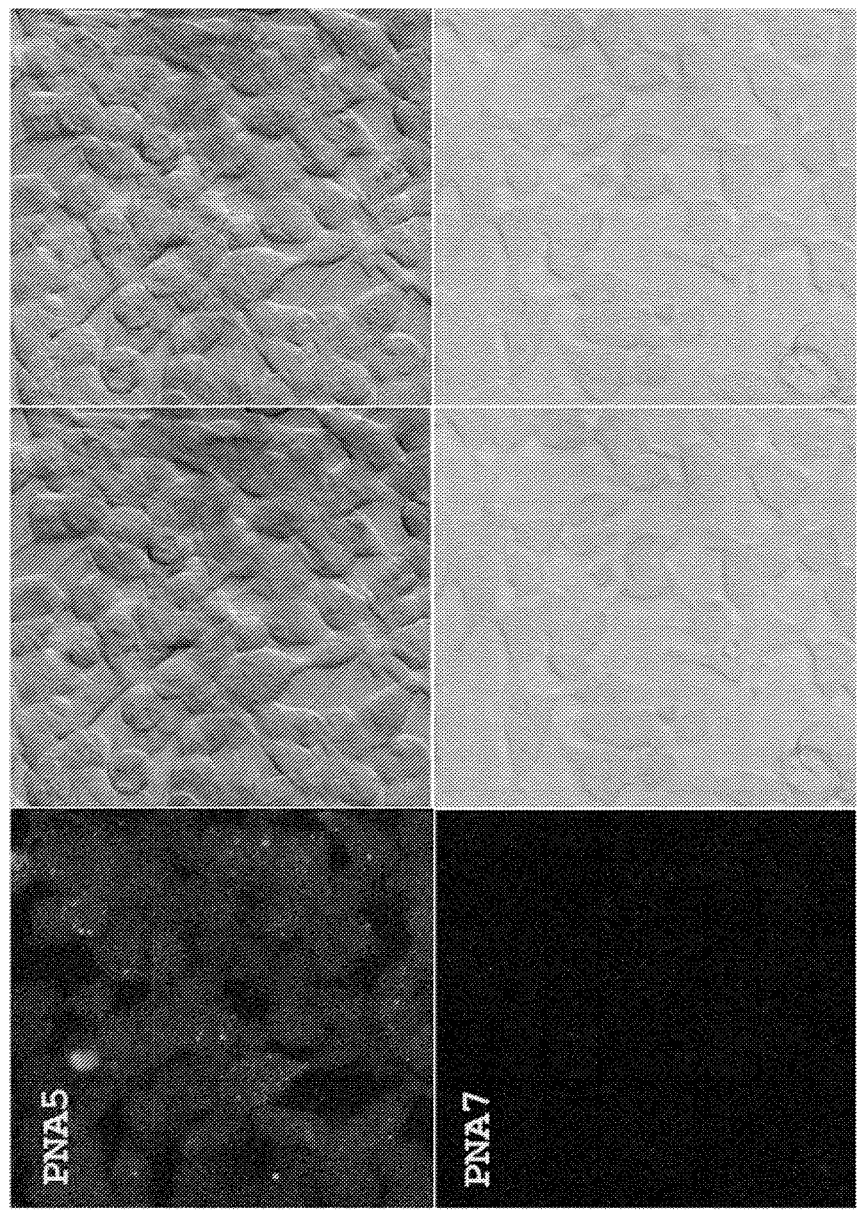
FIG. 8A shows uptake of PNA5 (upper panel) and PNA7 (lower panel) in live HEK293 cells monitored using confocal laser microscopy. The columns (left to right) represent fluorescence, optical, and combined images taken with a 40× objective.
Figure 8B:
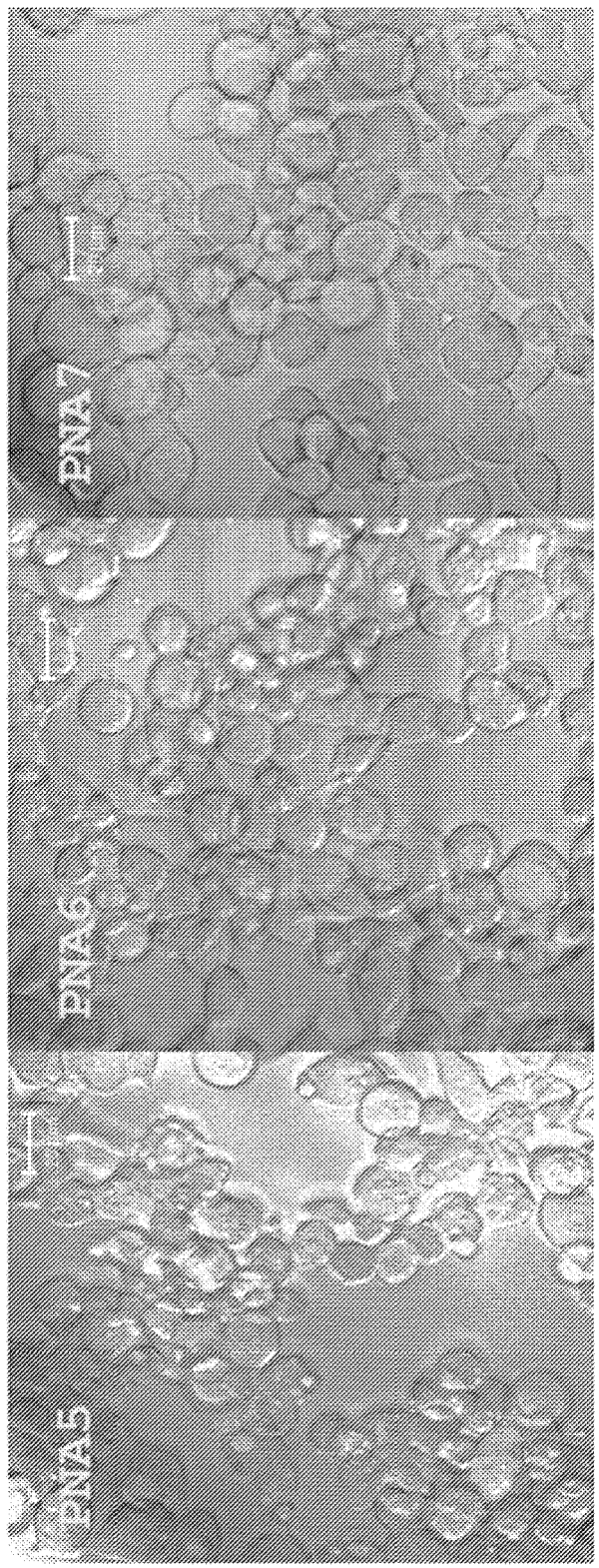
FIG. 8B shows combined fluorescence and optical images comparing uptake of M- and Lys-modified PNA5, Lys-modified PNA6, and unmodified PNA7 in live HEK293 cells.

Live HEK293 cells were incubated with 4 μM PNAs in Dulbecco's Modified Eagle's Medium at 37° C. for 24 h. The cells were washed with PBS buffer and immediately imaged without fixation (FIGS. 8A and 8B). In the first experiment, confocal fluorescence microscopy showed that the M- and Lys modified PNA5 efficiently penetrated HEK293 cells as judged by strong fluorescence in the upper panel of FIG. 8A. In contrast, little, if any, uptake of unmodified PNA7 could be seen as judged by low fluorescence of HEK293 cells in the lower panel of FIG. 8A. In the second experiment, comparison of PNAs carrying different modifications (FIG. 8B) showed that both M- and Lys-modifications contributed significantly to the efficient uptake of PNA5. While PNA6, bearing only additional Lys-modifications, showed some uptake, the fluorescence levels were significantly lower than those for the doubly modified PNA5. As in the first experiment, the unmodified PNA7 was not taken up by the HEK293 cells.

Finally, the binding of PNA5 to HRP6 modeling the purine-rich region

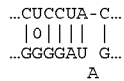

Figure 7:
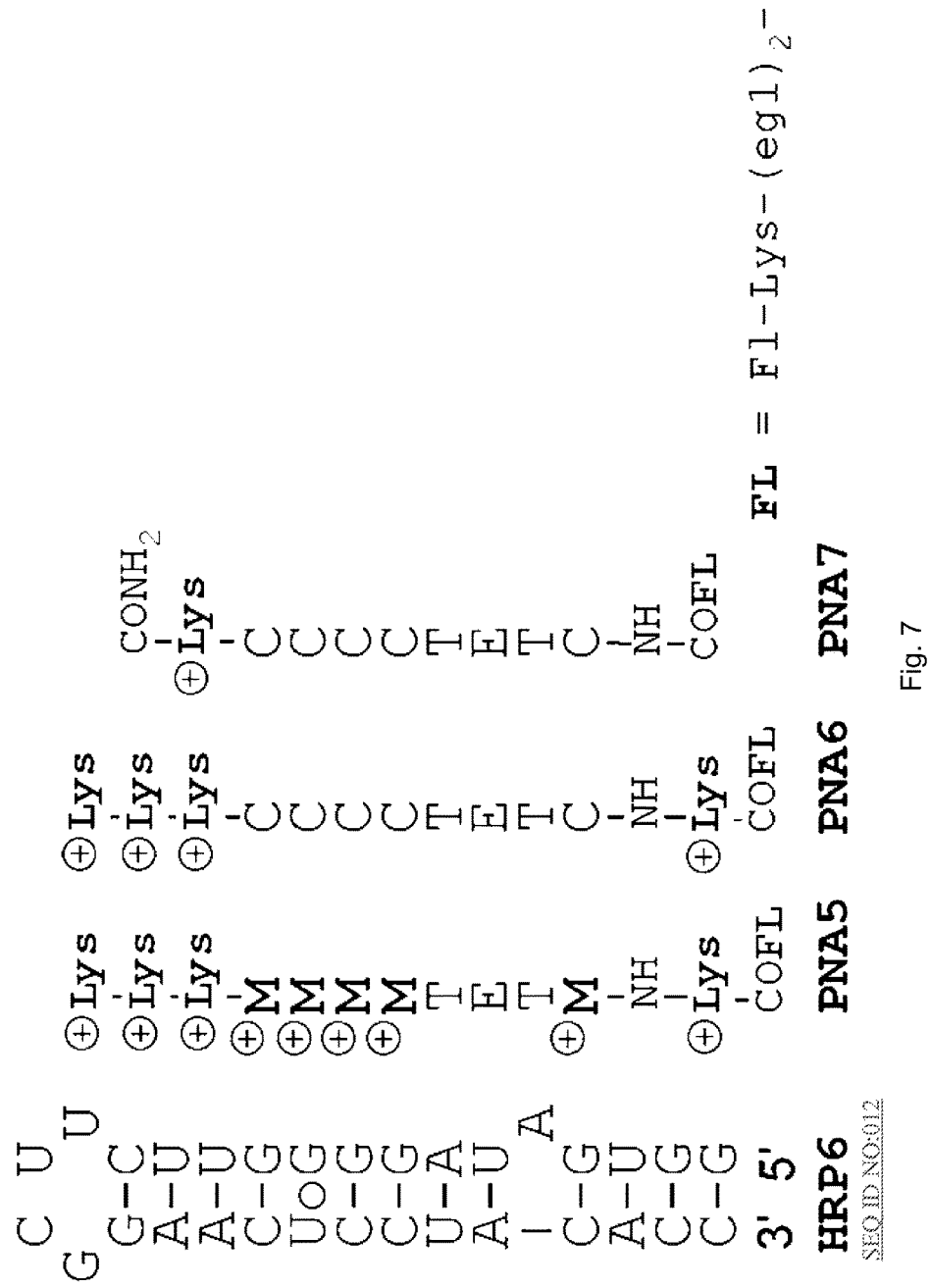
FIG. 7 shows structures of HRP6 modeling the PNA binding site of pri-miRNA-155 and fluorescein labeled PNAs.

(as shown in FIG. 7) of primiRNA-155 was studied. Analysis of the ITC trace showed that, as expected, PNA5 recognized HRP6 with high affinity ($K_a$=3.4×10$^7$ M$^{-1}$) and close to 1:1 stoichiometry under physiologically relevant conditions. Consistent with our previous results on a similar recognition of primiRNA-215 hairpin [29], the noncanonical structures in the primiRNA hairpin, the UoG wobble pair and A-bulge did not prevent formation of a stable PNA-RNA complex.

Biologically relevant double helical RNAs typically do not contain long polypurine stretches. However, it is common to find eight or more contiguous purines interrupted by one or two pyrimidines in rRNAs20 and miRNAs.[26] While such short sequences are not unique in the human genome, the fact that the triple helix forming PNAs require RNA to be in a double-stranded conformation increases the uniqueness of the recognition site. For example, a BLAST search of a comprehensive noncoding RNA database[43] revealed that in human RNA 5'-GAUAGGGG, the pri-miRNA-155 recognition site in HRP6, is also found in several Piwi-interacting RNAs and noncoding RNA regions (total of 11 hits). However, in these RNAs, the eight nucleotides are not part of doublestranded helices and thus are not expected to be viable recognition sites for PNA5. Among human pri-miRNAs, 5'-GAUAGGGG is unique to pri-miRNA-155; however primiRNA-3152 and pri-miRNA-6505 share a seven-nucleotide sequence, 5'-AUAGGGG. [26] If necessary, the specificity of PNA for pri-miRNA-155 can be further enhanced by extending the triplex recognition site to 5'-GUGAUAGGGG SEQ ID NO:002.

In summary, PNAs carrying multiple cationic M- and lysine modifications displayed high affinity and favorable sequence selectivity in triple helical binding to dsRNA. Attachment of short lysine peptides to PNA strongly enhanced binding of PNA to dsRNA while no binding could be observed to matched dsDNA. This is important for potential future applications in cells to eliminate nonspecific binding of PNA to nuclear dsDNA, which may cause undesired off-target effects. From this perspective the high RNA selectivity of the cationic PNAs is very encouraging. The results supported the hypotheses that cationic peptides: 1) prefer binding into the deep and narrow major groove of RNA over the major groove of DNA and 2) will provide additional stabilization of PNA-RNA triple helices.

Finally, encouraging cellular uptake of the M- and Lys-modified PNA was observed. Both modifications were important for efficient uptake of our PNAs. The present results suggest that PNAs carrying cationic M- and Lys-modifications are useful compounds for modulating the function of biologically relevant double-stranded RNA species in live cells.

Synthesis of PNA was done on Expedite 8909 synthesizer following the standard manufacturers protocol (2 μmol scale) and using NovaSyn TG Sieber resin (Novabiochem) as a support, HATU as an activator and Fmoc-PNA-A (Bhoc)-OH, Fmoc-PNA-C(Bhoc)-OH, Fmoc-PNA-G (Bhoc)-OH and Fmoc-PNA-T-OH as monomers (purchased from Link Technologies Ltd, UK). Chain extension followed a three-step cycle: (i) removal of the Fmoc-protecting group from the terminal amine with 20% piperidine in DMF, (ii) coupling of the next monomer onto the N-terminus of the growing chain with HATU, and (iii) capping of the unreacted amines with acetic anhydride.

D-Lysine was coupled to either NovaSyn TG Sieber resin (carboxyl end modification) or the PNA made on Sieber resin (amino end modification) using the following manual procedure. In a small vial, dissolve HATU (6.8 mg, 18 μmols) in anhydrous DMF (0.1 mL) and add N,N-diisopropylethylamine (5 μL, 36 μmols) and Fmoc-D-lys(Boc)-OH (10.6 mg, 18 μmols). Keep the mixture for two minutes before adding to Sieber resin by placing a 1 mL syringe on both sides of Expedite column and agitating periodically for 2 h (detailed procedure is described in Expedite manual). The reaction mixture was discarded and the resin was washed with anhydrous DMF (4×1 mL). The Fmoc group was deprotected using piperidine in DMF (0.8 mL, 20% v/v) and the same two-syringe method for 20 min and the resin was washed with DMF (4×1 mL). The same procedure was used to attach fluorescein-ε-N-lysine to the amino end to make PNA5 and PNA6. The resin was washed with anhydrous DMF (3×1 mL) and dichloromethane (3×1 mL) and dried under vacuum before proceeding to cleavage and deprotection steps.

Treating the solid resin with m-cresol/TFA (2:8) mixture for 2 h resulted in simultaneous removal of the protecting groups and cleavage of the oligomers from the resin. The crude PNA samples were precipitated from anhydrous ether. The solid was collected, dried, dissolved in HPLC grade water and purified by RPHPLC on Xbridge Prep C-18 column (5 μm, 10 mm×150 mm) at 65° C. eluting with a linear gradient 15%-35% of acetonitrile in water containing 0.1% of TFA over 40 min, flow rate of 5 mL/min. Absorbency was monitored at 210 nm and 254 nm, and the fraction containing the major peak was collected, lyophilized to dryness to afford pure PNA samples. The PNA was quantified following procedure described for DNA and RNA. [101] The molecular weight of the synthesized PNAs was confirmed by ESI or MALDI TOF mass spectrometry:

PNA1. ESI found m/z 1103.6 [M]2-, calculated for $C_{93}H_{144}N_{38}O_{26}$: 2209.1.

PNA2. MALDI TOF found m/z 2159 [M+H]$^+$, m/z 2181 [M+Na]$^+$, calculated for C96H147N35O23: 2158.

PNA4. ESI found m/z 1149.5 [M+2H]$^{2+}$, calculated for $C_{101}H_{149}N_{37}O_{26}$: 2296.2.

PNA5. MALDI-TOF found m/z 3277.8 [M+H]$^+$, calculated for $C_{151}H_{208}N_{46}O_{38}$: 3273.6.

PNA6. MALDI-TOF found m/z 3361.3 [M+H]$^+$, calculated for $C_{146}H_{203}N_{51}O_{43}$: 3358.5.

PNA7. MALDI-TOF found m/z 2977.1 [M+H]$^+$, calculated for $C_{128}H_{167}N_{45}O_{40}$: 2974.2.

RNA was purchased from Dharmacon Inc. and deprotected according to manufacturers recommendations. After deprotection RNA samples were purified using RP-HPLC on Xbridge Prep C-18 column (5 μm, 10 mm×150 mm) at 60° C. eluting with a linear gradient (5%-20%) of mobile phase B in mobile phase A over 40 min, flow rate 5 ml/min. Mobile phase A was 0.1 M of triethylammonium acetate (pH=7.0) in HPLC water and mobile phase B was a mixture of 0.1 M of triethylammonium acetate (pH=7.0) in HPLC water and HPLC grade acetonitrile (60/40, v/v). Absorbency was monitored at a wavelength of 254 nm and 280 nm, and the fraction containing the major peak was collected, lyophilized to dryness to afford pure RNA samples. RNA was quantified using the extinction coefficient provided by Dharmacon.

ITC Experiments were done on a Nano ITC G2 (TA Instruments) using either 5 or 2.5 nmols of RNA hairpins. The procedure is described for 2.5 nmols, for 5 nmols twice the amount of RNA and PNA was used. RNA stock solution (17.5 μL, 0.24 mM) was evaporated to dryness and the solid was dissolved in 1.6 mL of phosphate buffer (2 mM MgCl2, 90 mM KCl, 10 mM NaCl, 50 mM potassium phosphate at pH 7.4). After degassing, the RNA solution (0.95 mL, 0.002625 mM) was loaded into ITC reaction cell and the reference cell was loaded with degassed HPLC water. PNA stock solution (60 μL, 0.24 mM) was evaporated to dryness and the solid was dissolved in 320 μL of acetate buffer. After degassing the PNA solution (250 μL, 0.045 mM) was loaded in titration syringe. The syringe was inserted into reaction cell and the instrument was equilibrated at 37° C. until the baseline was flat and stable. The following parameters were used:

Experiment type: Incremental titration
Stirring rate=250 rpm
Temperature set point=37° C.
Syringe size=250 μl
Equilibration time=300 sec
Interval of individual injection=260-800 sec
Number of injections=50
Volume of individual injection=5 μl The titration data were analyzed using NanoAnalyze software (TA Instruments) and an independent model used to obtain the fitting graph and thermodynamic data of the experiments.

Cellular Uptake Experiments:

HEK 293 (ATCC® Number: CRL 1573) cells (~1×10$^7$ cells, ~1 mL) were grown in Dulbecco's Modified Eagle Medium (DMEM) containing 2 mM L-glutamine, 1% Penicillin, 10 nM non-essential amino acids and 10% fetal bovine serum (FBS). All cells were grown in 25 cm$^2$ cell culture flasks incubated in 90% humidified air and 5% CO2 at 37° C. At 70-80% confluence (~48 to 72 h), the growth medium was removed and cells were washed with 5 mL of PBS (Phosphate Buffered Saline). The cells were trypsinized with 1 mL 0.05% (w/v) Trypsin-0.53 mM EDTA solution for 3-5 min to dislodge them from the flask surface. Trypsin-EDTA was aspirated off, and a single cell suspension prepared by adding 5 mL of complete growth medium and pipetting gently against the flask surface to break up clusters. In separate vials, fluorescein modified PNA, Fl-Lys-(eg1)2-d-Lys-MTETMMMM-(d-Lys)3 (PNA5) and Fl-Lys-(eg1)2-CTETCCCC-d-Lys (PNA6), stock solutions (21 μL of 240 mM) were diluted with complete growth medium to a final concentration of 4 μM PNA in 500 μL DMEM. PNA solutions (500 μL) were transferred to a 24 well tissue culture plate. An appropriate volume of the cell suspension (100-200 μL) was added to each well containing PNA solution, and the cultures incubated at 37° C., 90% air, 5% CO$_2$ for 24 h. The culture medium was removed and cells washed twice with PBS before imaging.

Fluorescence and optical images were taken using an inverted Axiovert Zeiss Laser Scanning Microscope 510. For fluorescence images, the samples were excited at 488 nm using an argon-ion laser and fluorescence, optical and combined images were taken with a 40× objective.

TABLE 5

Analyzed ITC data.

| Sequence | RNA conc | $K_a$ (M$^{-1}$) | ΔH (kcal/mol) | ΔS (eu) | ΔG (kcal/mol) | Stoichiom. |
|---|---|---|---|---|---|---|
| HRP1 | | | | | | |
| PNA1 | 2.60 μM | 3.40E+06 | −6.9 | 7 | −8.9 | 1.2 |
| PNA2 | 2.60 μM | 5.20E+06 | −16.2 | −24 | −9.2 | 0.6 |
| PNA4 | 5.25 μM | 2.30E+06 | −40.1 | −105 | −8.7 | 1.2 |
| HRP2 | | | | | | |
| PNA1 | 2.60 μM | 1.90E+06 | −13.1 | −15 | −8.6 | 3.0 |
| PNA2 | 2.60 μM | 1.10E+08 | −62.3 | −172 | −11.0 | 1.0 |
| | | 2.20E+08 | −56.6 | −152 | −11.4 | 0.9 |
| | average | 1.65E+08 | −59.5 | −162 | −11.2 | 1.0 |
| | standard dev | 7.78E+07 | 4.1 | 15 | 0.3 | 0.1 |
| PNA4 | 5.25 μM | 2.30E+07 | −48.2 | −128 | −10.0 | 1.0 |
| | | 9.20E+06 | −36.3 | −90 | −9.5 | 1.3 |
| | | 2.10E+07 | −43.0 | −111 | −10.0 | 1.1 |
| | average | 1.77E+07 | −42.5 | −110 | −9.8 | 1.1 |
| | standard dev | 7.46E+06 | 6.0 | 19 | 0.3 | 0.2 |
| HRP3 | | | | | | |
| PNA1 | 2.60 μM | 3.10E+06 | −1.7 | 24 | −8.9 | 7.3 |
| PNA2 | 2.60 μM | 5.10E+04 | −29.4 | −77 | −6.4 | 1.6 |
| HRP4 | | | | | | |
| PNA1 | 2.60 μM | 3.10E+05 | −1.4 | 20 | −7.5 | 4.3 |
| PNA2 | 2.60 μM | <10E+3 | No binding detected | | | |
| PNA4 | 5.25 μM | 5.90E+05 | −22.0 | −47 | −7.9 | 0.7 |
| HRP5 | | | | | | |
| PNA2 | 2.60 μM | <10E+3 | No binding detected | | | |
| PNA4 | 5.25 μM | <10E+3 | No binding detected | | | |

TABLE 6

UV thermal melting data ($t_m$ in ° C.)

| RNA Hairpin | PNA2 | PNA4 |
|---|---|---|
| HRP1 | 46 | 36 |
| HRP2 | — [a] | — [a] |
| HRP3 | 27 | 23 |
| HRP4 | 26 | 23 |

[a] The triplex dissociation overlapped with hairpin melting giving one transition at around 90° C.

Example 3

Experimental Procedures

Isothermal titration calorimetry and fluorescence spectroscopy were used to study binding of GPNA, which is distinct from PNA studied in Examples 1 and 2, to double-helical RNA.[6] The results were further confirmed using circular dichroism (CD) spectroscopy and a gel mobility shift assay. Guanidine modification was found to reduce the affinity and sequence selectivity of PNA with respect to complementary double-helical RNA. The binding stoichiometry increased to a 2:1 PNA-RNA complex, suggesting that the most likely mode of binding was a strand invasion triplex. While GPNA did not favor triple-helix formation, strong and sequence selective recognition of transactivation response element (TAR) RNA of HIV-1 was achieved using the GPNA derived from D-arginine in a strand invasion mode. Unmodified and nucleobase-modified PNA also gave promising results for triple-helical recognition of bacterial A-site RNA.

Isothermal Titration calorimetry. In a typical ITC experiment, an RNA hairpin solution (0.95 mL, 5.25 mM) in acetate buffer [100 mM sodium acetate and 1.0 mM EDTA (pH 5.5)] was titrated with a PNA solution (50×5 μL, 96 mM) using a Nano ITC G2 (TA Instruments) calorimeter. For full experimental details and data, see the Supporting Information. The titration data were analyzed using Nano-Analyze (TA Instruments) using an independent model to obtain the fitting graph and thermodynamic binding data (Table 7).

Fluorescence Spectroscopy. An HRP7 (TAR RNA model) solution (2 mL, 0.1 mM) in phosphate buffer [10 mM phosphate, 0.1 mM EDTA, and 1 mM $MgCl_2$ (pH 6.8)] was heated for 6 min in a 90° C. water bath and then snap-cooled by being immediately placed in an ice bath. The sample was placed in a 1 cm path length cuvette and equilibrated at 20° C. using a circulating water bath. The excitation wavelength was set to 305 nm; the emission wavelength was observed at 365 nm. The excitation and emission bandwidth was 10 nm. Titration of the PNA into TAR RNA was achieved via addition of 1-6 μL aliquots of concentrated PNA stock solutions to reach the required PNA concentration of 0.002-2 μM. After each addition of PNA, the mixture was stirred for 30 min before the fluorescence intensity was measured using a Shimadzu RF-5301pc spectrofluorometer. The data were analyzed by fitting the change in fluorescence intensity to a single-site, two-state binding model as previously described. [77]

Results

Figure 9:
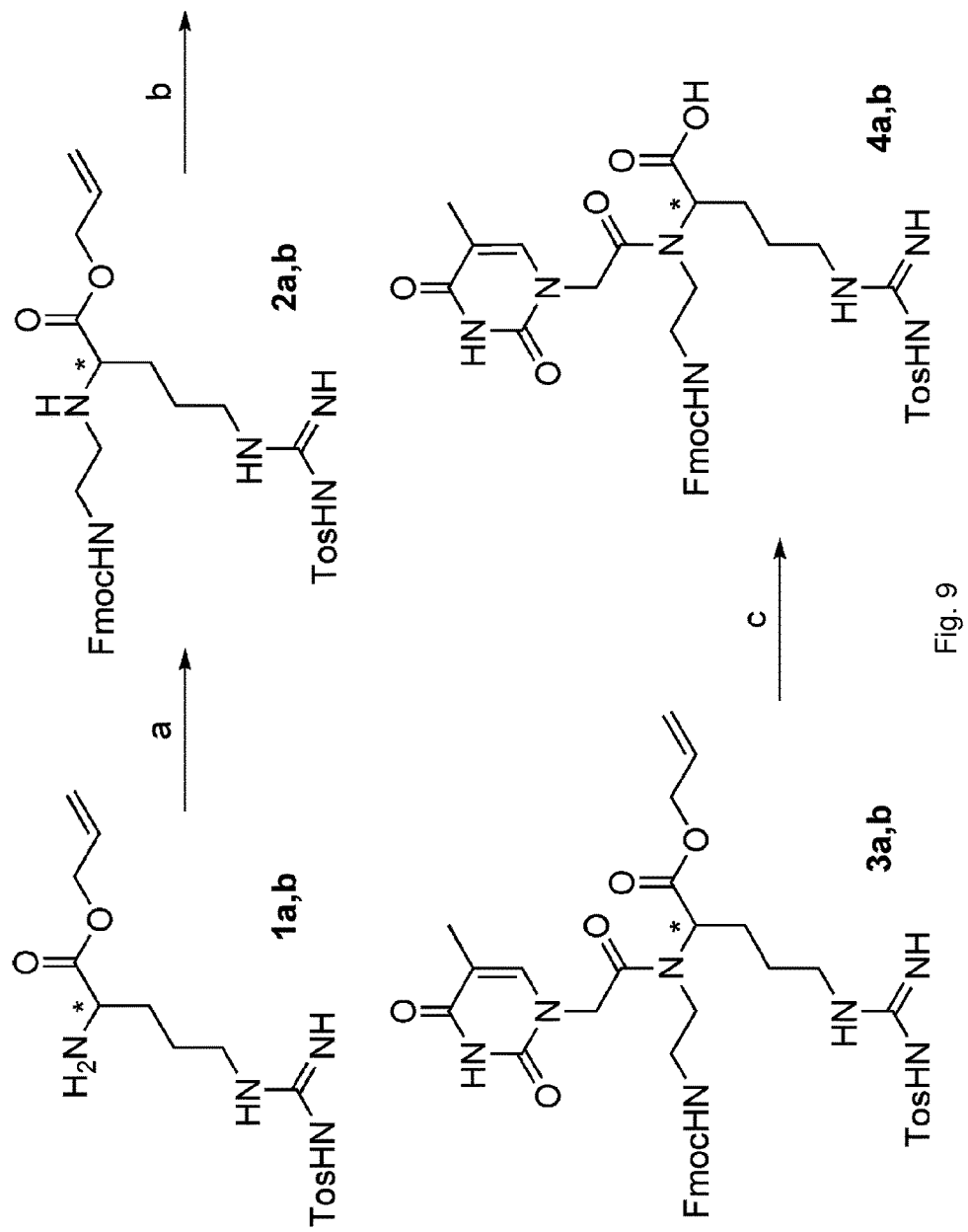
FIG. 9 shows a synthesis pathway for Fmoc-Protected GPNA Monomers.

The synthetic route designed by Ly and co-workers [74, 76] was modified for preparing Fmoc-protected GPNA monomers that would be compatible with standard PNA synthesis protocols for the Expedite 8909 DNA synthesizer. Starting from known intermediates 1a and 1b (Scheme 2),[74,76] reductive amination with Fmoc-glycinaldehyde [78] gave backbone intermediates 2a and 2b. The target thymidine GPNA monomers [4a and 4b (Scheme 2), shown in FIG. 9] were prepared by coupling of 2a and 2b with thymine-1-acetic acid, which was prepared according to established procedures, [76] followed by deprotection using N-ethylaniline and $Pd(PPh_3)_4$. [73,79]. In FIG. 9, The a series has R stereochemistry (derived from D-arginine); and the b series S stereochemistry (derived from L-arginine) at the chiral center (asterisks). Steps (yields for D-series): (a) $Fmoc-NHCH_2CHO$, MeOH, 0° C., 4 h, acetic acid, $NaBH_3CN$, 30 min (57%); (b) thymine-1-acetic acid, 3-hydroxy-1,2,3-benzotriazin-4(3H)-one, N-[3-(dimethylamino) propyl]-N'-ethylcarbodiimide, dimethylformamide, 40° C., 12 h (60%); (c) $Pd(PPh_3)_4$, N-ethylaniline, tetrahydrofuran, room temperature, 1 h (81%).

Figure 10:
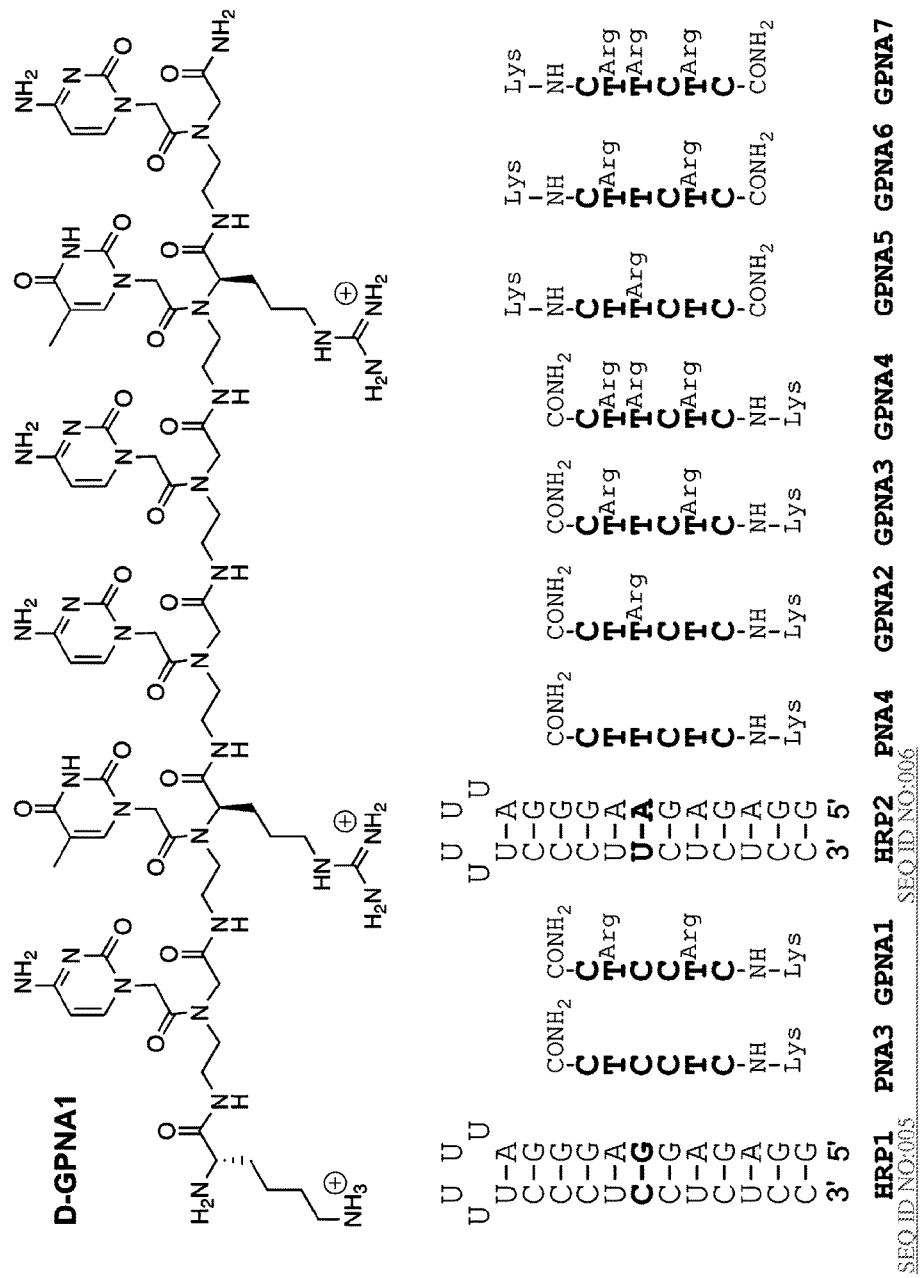
FIG. 10 shows the structure of GPNA and sequences of RNA hairpins, PNA, and GPNA (the numbering of RNA hairpins and PNA is from ref [4]).
Figure 11:
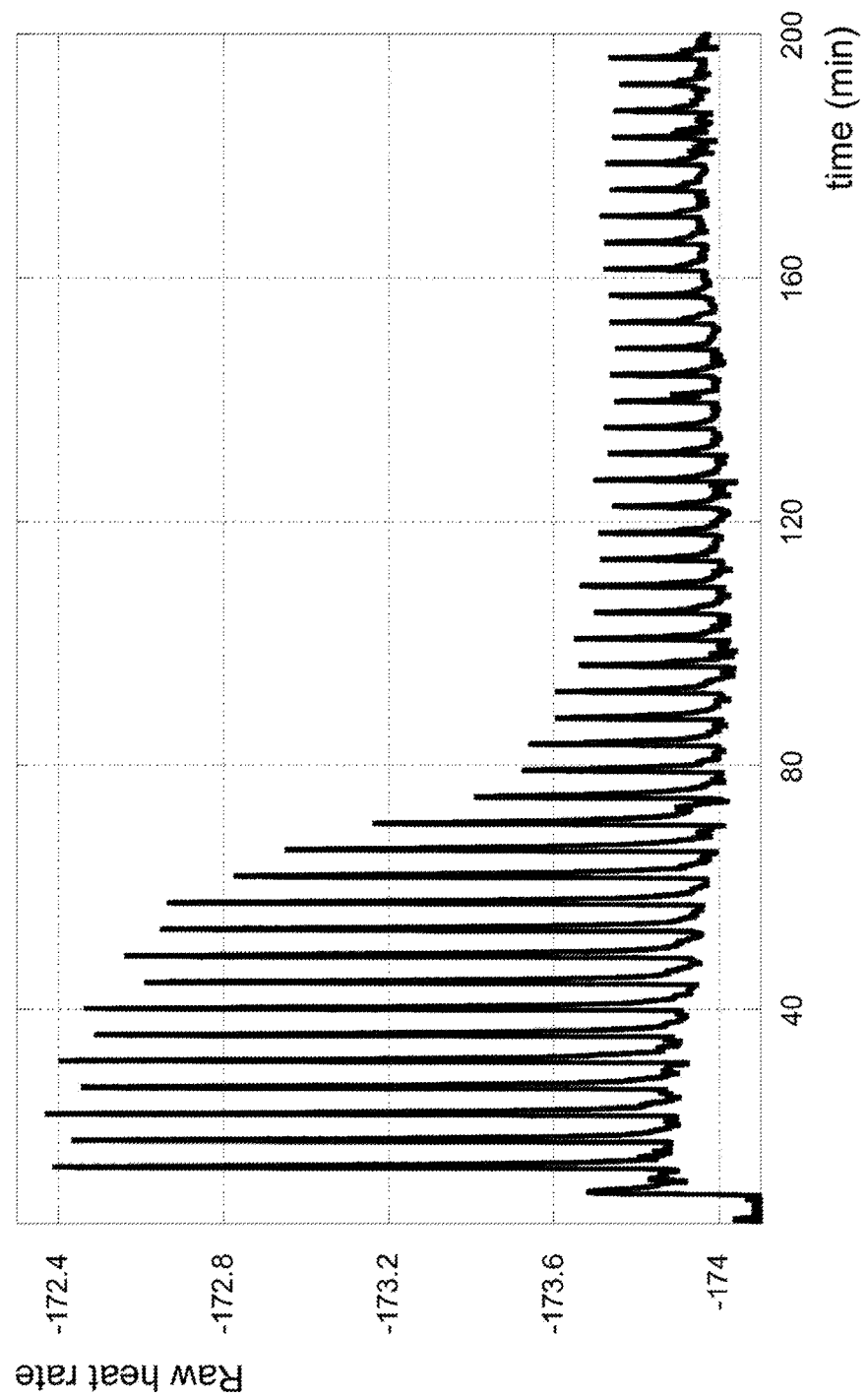
FIG. 11 shows ITC titration curve of D-GPNA1 (5 μL injections of 96 μM) binding to HRP1 (5.25 μM)

The guanidine-modified PNA oligomers [GPNA (FIG. 10)] were made using the standard Fmoc synthesis protocols on the Expedite 8909 synthesizer and purified by reverse-phase high-performance liquid chromatography. Cleavage from the solid support and removal of all protecting groups (including the Ntosyl group) were achieved with a mixture of m-cresol, thioanisole, trifluoromethanesulfonic acid, and trifluoroacetic acid (1:1:2:6) as previously reported.[74] To allow direct comparison, the same GPNA sequences were prepared (FIG. 10), like the PNA used in previous study of triple-helix formation with double-helical RNA. [4] The binding of GPNA to RNA hairpin (HRP1) was studied using isothermal titration calorimetry [ITC (FIG. 11)]. The ITC results, summarized in Table 7, showed that modification of both T monomers in the hexamer CTCCTC (PNA3) with a guanidine residue derived from either D- or L-arginine lowered the affinity for double-stranded RNA (cf., entry 1 with entries 2 and 3). Interestingly, the binding order (PNA: RNA stoichiometry) increased from 1 (observed in previous study) to 2, suggesting that a more complex binding mode, presumably a duplex invasion forming a GPNA-RNA-GPNA triple helix, was taking place (FIGS. 12A-12C). Formation of the complex was further confirmed using circular dichroism (CD) spectroscopy. Wittung et al. have shown that strand invasion of the DNA duplex by PNA resulted in a decrease in the magnitude of the CD signal at 240-250 nm and an increase in the magnitude of the CD signal at ~280 nm.[81,82] In contrast to unmodified PNA, GPNA exhibited a weak but notable CD signal at the concentration used in ITC experiments. Addition of 4.5 equiv (conditions mimicking the end point of ITC titration) of D-GPNA1 and L-GPNA1 to HRP1 induced a decrease in the magnitude of the CD signal at 240-250 nm, which was clearly visible in the difference spectra. However, a significant increase around 280 nm was not observed. In contrast, the binding of D-GPNA1 showed a decrease in the magnitude of the signal at that wavelength. Overall, the CD spectra confirmed the formation of GPNA-RNA complexes.

TABLE 7

Thermodynamic Data for Binding of PNA and GPNA to RNA and DNA Hairpins [a]

| entry | sequence | $K_a$ ($\times 10^6 M^{-1}$) | -ΔH (kcal/mol) | -ΔS (eu) | -ΔG (kcal/mol) | binding order |
|---|---|---|---|---|---|---|
| Symmetric Sequence, optimal for a parallel triple helix and an antiparallel duplex (strand invasion). | | | | | | |
| 1b | PNA3 NH2-CTCCTC | 84 ± 80 | 29.4 ± 5.3 | 63 ± 17 | 10.6 ± 0.5 | 1.1 ± 0.2 |

TABLE 7-continued

Thermodynamic Data for Binding of PNA and GPNA to RNA and DNA Hairpins [a]

| entry | sequence | $K_a$ ($\times 10^6$ M$^{-1}$) | $-\Delta H$ (kcal/mol) | $-\Delta S$ (eu) | $-\Delta G$ (kcal/mol) | binding order |
|---|---|---|---|---|---|---|
| 2 | D-GPNA1<br>NH2-CTD-ArgCCTD-ArgC | 4.6 ± 1.6 | 27.3 ± 2.5 | 61 ± 9 | 9.1 ± 0.2 | 1.8 ± 0.1 |
| 3 | L-GPNA1<br>NH2-CTL-ArgCCTL-ArgC | 2.2 ± 1.6 | 24.2 ± 9.6 | 53 ± 34 | 8.6 ± 0.5 | 2.0 ± 0.1 |
| 4c | D-GPNA1<br>NH2-CTD-ArgCCTD-ArgC | 0.4 | 29.1 | 72 | 7.7 | 2.1 |
| 5c | L-GPNA1<br>NH2-CTL-ArgCCTL-ArgC | 2.5 | 21.0 | 41 | 8.7 | 2.2 |
| | Sequence Optimal for a Parallel Triple Helix | | | | | |
| 6b | PNA4<br>NH2-CTCTTC | 47 ± 22 | 26.4 ± 3.2 | 54 ± 12 | 10.4 ± 0.3 | 1.3 ± 0.1 |
| 7 | D-GPNA2<br>NH2-CTCTD-ArgTC | 0.5 | 70.0 | 209 | 7.8 | 0.5 |
| 8 | D-GPNA3<br>NH2-CTD-ArgCTTD-ArgC | 0.5 | 41.8 | 114 | 7.8 | 0.8 |
| 9 | D-GPNA4<br>NH2-CTD-ArgCTD-ArgTD-ArgC | 0.6 | 22.9 | 50 | 7.9 | 1.2 |
| 10 | L-GPNA2<br>NH2-CTCTL-ArgTC | 1.8 | 39.6 | 104 | 8.5 | 0.7 |
| 11 | L-GPNA3<br>NH2-CTL-ArgCTTL-ArgC | 0.8 | 58.8 | 170 | 8.0 | 0.5 |
| 12 | L-GPNA4<br>NH2-CTL-ArgCTL-ArgTL-ArgC | 0.5 | 61.6 | 181 | 7.8 | 0.4 |
| | Sequence Optimal for an Antiparallel Duplex (strand invasion) | | | | | |
| 13d | D-GPNA5<br>NH2-CTTD-ArgCTC | 10.5 | 19.8 | 34 | 9.6 | 1.4 |
| 14d | D-GPNA6<br>NH2-CTD-ArgTCTD-ArgC | 5.0 | 13.4 | 14 | 9.1 | 2.0 |
| 15d | D-GPNA7<br>NH2-CTD-ArgTD-ArgCTD-ArgC | 0.4 ± 0.01 | 25.8 ± 3.7 | 61 ± 13 | 7.6 ± 0.0 | 2.3 ± 0.0 |
| 16d | L-GPNA7<br>NH2-CTL-ArgTL-ArgCTL-ArgC | 3.8 ± 0.1 | 13.0 ± 7.3 | 14 ± 25 | 8.9 ± 0.3 | 2.1 ± 0.1 |

[a] Average association constants $K_a$ (±standard deviation) in 100 mM sodium acetate and 1.0 mM EDTA (pH 5.5). Entries 1-3 are for binding to HRP1, entries 4 and 5 for binding to a DNA version of HRP1, and entries 6-16 for binding to HRP2.
[b] From previous study. 60
[c] Binding to a DNA version of HRP1. dPNA antiparallel to the purine tract of HRP2 (FIG. 12B).

Binding of D-GPNA1 to the HRP1 hairpin, consistent with [4], made of deoxynucleotides (DNA version of HRP1) was weaker by ~1 order of magnitude (cf., entries 2 and 4). In contrast, the affinity of L-GPNA1 for either the RNA or DNA hairpin was practically the same (cf., entries 3 and 5). Under physiologically relevant conditions [37° C., in 2 mM MgCl2, 90 mM KCl, 10 mM NaCl, and 50 mM potassium phosphate (pH 7.4)], no binding of D-GPNA1 to HRP1 was observed. The sequence of PNA3 was symmetric and thus provided optimal binding for formation of both a parallel triple helix and an antiparallel duplex, as required for triplex invasion (FIGS. 12A-12C).

To gain more insight into different binding modes, guanidine-modified variants of hexamer CTCTTC (PNA4) were prepared and studied their binding to HRP2. All the sequences designed to bind in a parallel mode to the polypurine tract of HRP2 [in GPNA2-GPNA4 (FIG. 10), the amino terminus aligns with the 5' end of RNA (see also FIG. 12A)] had a similar affinity for the RNA target that was ~2 orders of magnitude lower than the affinity of the unmodified PNA4 (in Table 7, cf., entry 6 and entries 7-12). While there was very little dependence on the number of modifications in the D series (entries 7-9), in the L series (entries 10-12) the affinity appeared to decrease somewhat with an increasing number of guanidine modifications. Interestingly, increasing the number of modifications in the D series was followed by a decrease in both binding enthalpy and entropy ($\Delta H$ and $\Delta S$, respectively, in Table 7), while the reverse was true in the L series. This result suggested that the stereoisomeric guanidine modifications had distinct interactions with the RNA target. The PNA:RNA stoichiometry (binding order in Table 7) suggested that the parallel GPNA maintained the original PNA-RNA-RNA triple-helical mode of recognition.

In contrast, the sequences designed to bind in an antiparallel mode (FIG. 12B) to the polypurine tract of HRP2 [in GPNA5-GPNA7 (FIG. 10), the amino terminus aligned with the 3' end of RNA] had significant differences in binding affinity depending on the number and stereochemistry of guanidine modifications. In the D series (entries 13-15), the binding affinity decreased more than 20-fold going from one (entry 13) to three guanidine modifications (entry 15). The binding order increased to 2 with two and three guanidine modifications, suggesting that the antiparallel sequences may favor triplex invasion [GPNA-RNA-GPNA (FIG. 12C)], as observed for GPNA1 (entries 2 and 3). GPNA7 derived from Larginine (entry 16) had a significantly higher affinity than the D isomer (entry 15). Binding of GPNA7 to HRP2 produced similar changes in CD spectra as observed for GPNA1 and HRP1. While DGPNA5 had the highest binding affinity [Ka ~$10^7$ (entry 13)] among all guanidine-modified PNA tested at pH 5.5, no binding was observed when the experiment in entry 13 was repeated in acetate buffer at pH 7.3.

Next the sequence selectivity of binding of GPNA1 to all four RNA hairpins having a variable central base pair [HRP1-HRP4 (FIGS. 6 and 10)] was checked.

The results in Table 9 showed that the affinity of unmodified PNA3 and either the D or the L isomer of GPNA1 for the "mismatched" hairpins (HRP2-HRP4) was approximately the same (D-GPNA1 vs HRP4 was the only notable exception). Thus, the sequence specificity of GPNA was reduced compared to that of unmodified PNA because of the lower affinity for the "matched" target (highlighted in bold in Table 8). The sequence selectivity of antiparallel (FIG. 12B) GPNA8 and GPNA9 in comparison with PNA5 and PNA6, respectively was also studied. These sequences all have a mismatched central Hoogsteen base triplet; however, because two molecules of D-GPNA8 and D-GPNA9 bind to an RNA hairpin [binding order of 2 (see the Supporting Information)], the combination D-GPNA8 and HRP3 and the combination of D-GPNA9 and HRP4 would have a matched Watson-Crick base pair if the binding were following the triplex-invasion mode (FIG. 12C).

TABLE 8

Sequence Selectivity of Binding of GPNA to RNA Hairpins [a]

| PNA (variable base) | HRP1a (G-C) | HRP2a (A-U) | HRP3a (C-G) | HRP4a (U-A) |
|---|---|---|---|---|
| PNA3 (C )[b] | 84 | 0.4 | 0.5 | 0.2 |
| D-GPNA1 | 4.6 | 0.3 | 0.7 | 1.3 |
| L-GPNA1 | 2.2 | 0.8 | 0.6 | 0.4 |
| PNA5 (G)[b] | 1.5 | 0.4 | 0.2 | 0.1 |
| D-GPNA8[c] | 0.8 | 0.6 | 1.2 | 0.7 |
| PNA6 (A)[b] | 6.0 | 1.6 | 0.7 | 0.05 |
| D-GPNA9[c] | ND[d] | 0.6 | ND[d] | 0.97 |

[a]Average association constants [$K_a$ ($\times 10^6$ M$^{-1}$)] in sodium acetate buffer (pH 5.5).
[b]From previous study.[4]
[c]PNA antiparallel to the purine tract of RNA.
[d]Not determined.

TABLE 9

Binding of PNA and GPNA (L series) to Ribosomal A-Site Model RNA Hairpins (FIG. 15)[a]

| entry | PNA sequence | M. tuberculosis (HRP6) | H. Sapiens (HRP5) |
|---|---|---|---|
| 1 PNA10 | NH2-CCCTGCTT | 1.2 (1.7) | 0.4 (2.0) |
| 2 GPNA10 | NH2-CCCTL-ArgGCTL-ArgT | 0.5 (2.9) | 2.8 (5.0) |
| 3 PNA11 | NH2-CCTGCTT | 0.2 (1.1) | 0.04 (0.9) |
| 4 PNA12 | NH2-CTGCTT | 0.2 (1.6) | 0.06 (0.9) |
| 5 GPNA12 | NH2-CTL-ArgGCTT | 0.4 (1.8) | 0.8 (2.1) |
| 6 GPNA13 | NH2CTL-ArgGCTL-ArgT | 2.9 (8.0) | 8.1 (8.8) |
| 7 PNA13 | NH2-CCCTPCTT | 1.5 (1.1) | NB[b] |
| 8 PNA14 | NH2-CCCTPexCTT | 2.0 (1.1) | NB[b] |

[a]Average association constants [$K_a$ ($\times 10^6$ M$^{-1}$)] in sodium acetate buffer (pH 5.5); the binding order is given in parentheses.
[b]No binding; $K_a < 10^3$ M$^{-1}$.

Indeed, D-GPNA8 had a higher binding affinity than PNA5 for HRP3, consistent with formation of the G-C base pair upon invasion, and HRP4, possibly due to a stabilizing G-U wobble base pair (highlighted in bold in Table 8). A similar result, consistent with formation of an A-U base pair, was obtained for the combination of D-GPNA9 and HRP4, supporting the hypothesis that the binding order of 2 indicated triplex invasion and formation of a GPNA-RNA-GPNA complex.

Figure 15:
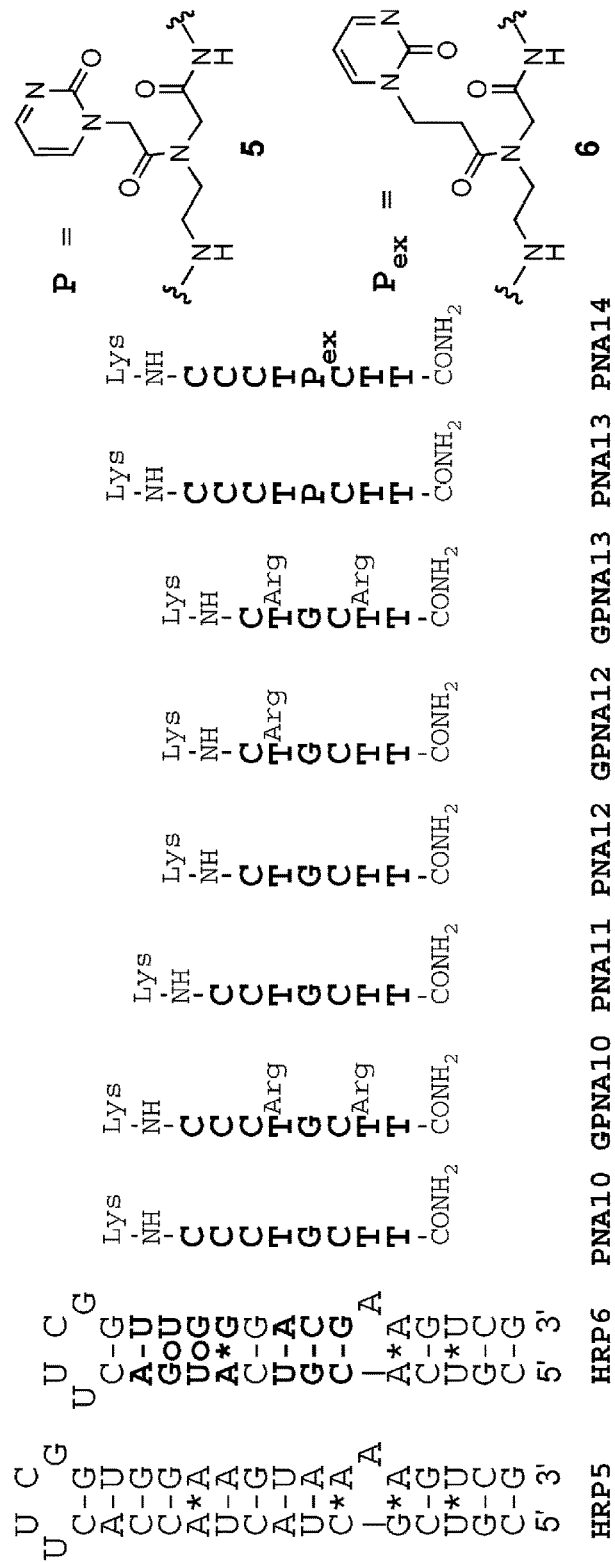
FIG. 15 shows the structure of ribosomal A-site model RNA hairpins and the complementary PNA and GPNA.
Figure 16:
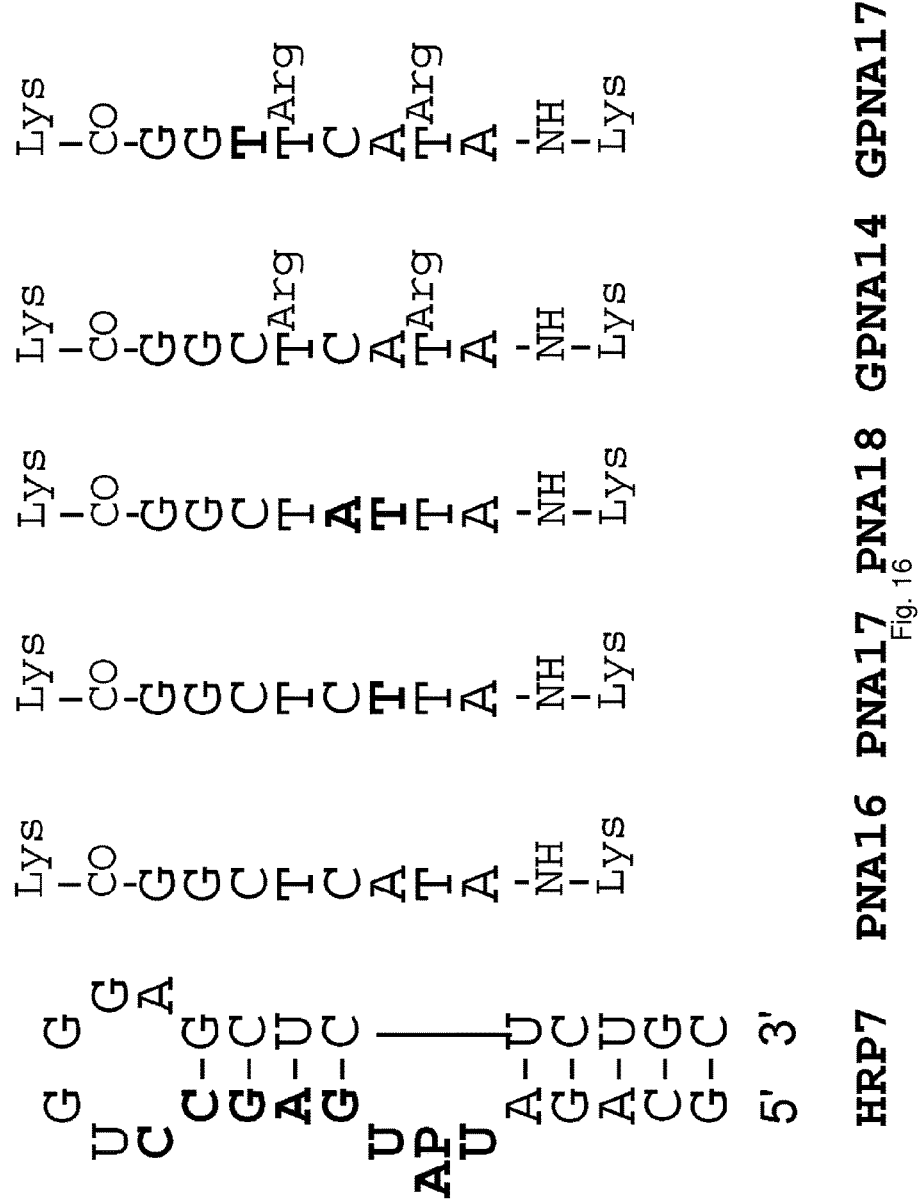
FIG. 16 shows the structure of the TAR RNA hairpin and complementary PNA and GPNA, in which the target site on RNA and the mismatched nucleobases are highlighted in bold; AP is 2-aminopurine.

Next, PNA and GPNA were tested for recognition of more complex biologically relevant RNA, such as the ribosomal A-site. Model hairpins (FIG. 15) were designed to contain the secondary structure of ribosomal A-sites (sequences from www.rna.ccbb.utexas.edu/) of *Homo sapiens* (HRP5) and *Mycobacterium tuberculosis* (HRP6) and to close at one end with a stable RNA tetraloop and on the other end with a couple of C-G base pairs. The structures of the A-rich bulge, which is the target of aminoglycoside antibiotics, of bacterial and human A-sites are remarkably similar. However, significant differences occur in the helical region just above the A-rich bulge (bold in FIG. 15). Interestingly, the A-site helices feature short polypurine tracts interrupted by a single pyrimidine, U in HRP5 and C in HRP6, which prompted us to explore if the A-site RNA may be recognized via triplex or triplex-invasion mode (FIG. 15 and Table 6).

In general, PNA and GPNA (L series) targeting the A-site exhibited modest binding affinity, which was consistent with the impact of a mismatched base triplet observed in previous study. [4] Octamer PNA10 had low sequence selectivity for the bacterial A-site, and the binding order indicated potential triplex invasion (Table 9, entry 1). Surprisingly, guanidine modification resulted in an increased affinity of GPNA10 for the human A-site and a dramatic loss of sequence selectivity, which correlated with large increases in the level of binding order (Table 9, entry 2). Shortening the PNA to a heptamer (PNA11) and a hexamer (PNA12) slightly decreased the affinity and increased the sequence selectivity. Guanidine modifications in GPNA12 and GPNA13 increased the binding affinity, but the sequence selectivity was lost. It is conceivable that the unusually high binding orders for GPNA10 and GPNA13 resulted from nonspecific electrostatic association of these GPNA carrying two guanidine modifications with the relatively more flexible (because of the noncanonical base pairs) A-site RNA. Recently, it was shown that 2-pyrimidone, as in the novel PNA monomers 5 and 6 (FIG. 15) formed a matched triplet with a C-G inversion in the purine-rich strand of double-helical RNA. [5] Replacing the mismatched G in PNA10 with P and Pex (monomers 5 and 6, respectively) increased the affinity of PNA13 and PNA14 for the bacterial A-site. The stoichiometry of the complex was close to 1:1 as expected for the triple helix. Most remarkably, the sequence selectivity was excellent; no binding to the human Asite was observed. The preference of guanidine-modified PNA to form strand invasion complexes prompted us to check if GPNA could bind RNA structures that do not have continuous polypurine tracts.

Figure 12:
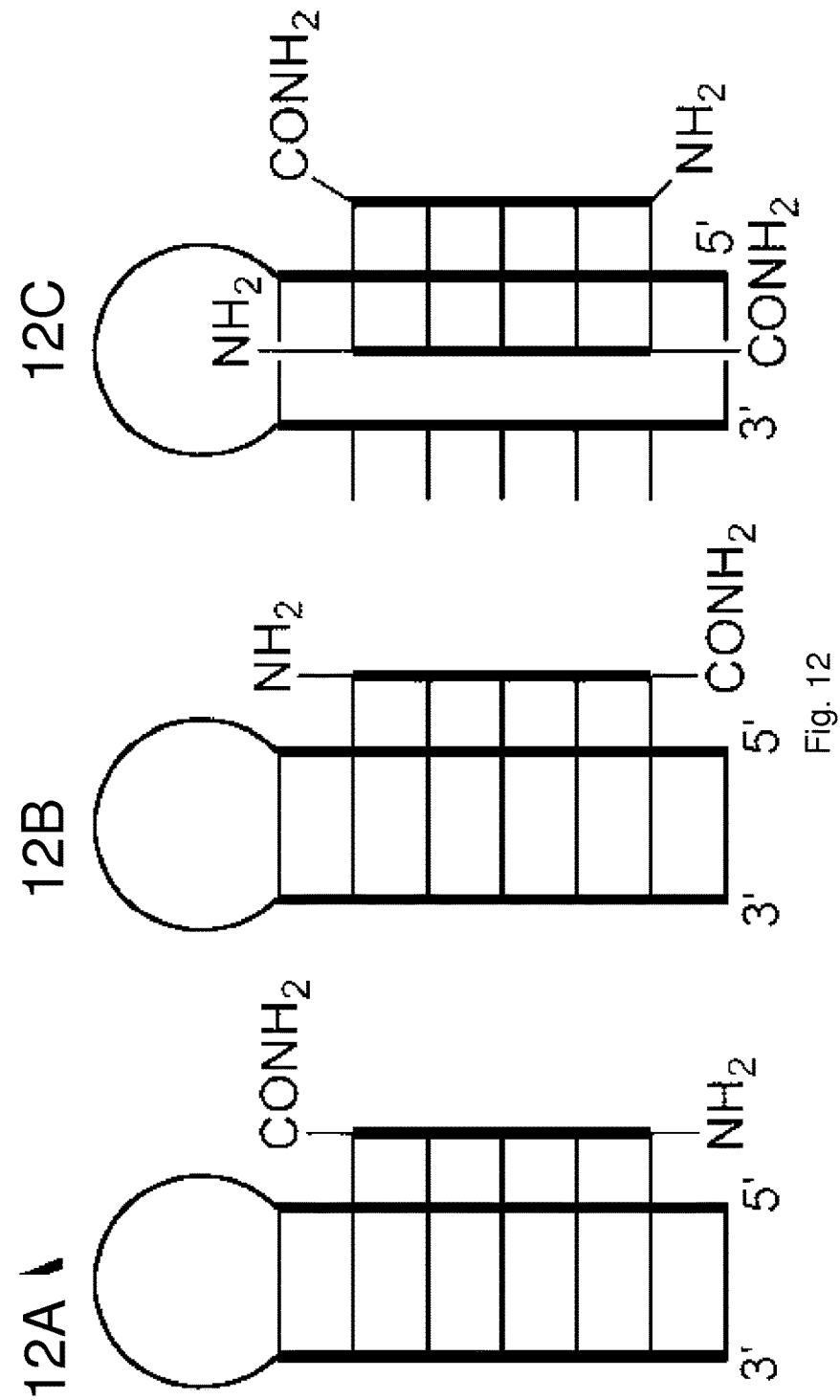
FIGS. 12A-12C show a schematic representation of the binding modes.

To test this hypothesis, the model RNA sequence of the transactivation response element (TAR) of HIV-1 virus (FIG. 12) was selected. The bulged structure was predicted to be thermally less stable than a canonical Watson-Crick helix and may predispose the RNA for strand invasion by PNA. To test this hypothesis, PNA16 was chosen as complementary to the U-rich loop and the stem connecting the U-rich loop and the hairpin loop. This sequence design was similar to that of Pandey [82-84] and others, [85] except that the G-rich hairpin loop was not included in the recognition site because the focus was on testing duplex invasion as opposed to Watson-Crick binding to the flexible loop. Initial experiments were frustrated by an apparent aggregation of PNA at high concentrations (~100 μM) in the injection syringe of ITC. While PNA used in the ITC studies described above had no more than one purine base (<20%), PNA complementary to TAR RNA had 50% purines (FIG. 12), which may cause some aggregation at high concentrations. In a search for an alternative method, fluorescence spectroscopy of RNA labeled with the highly fluorescent 2-aminopurine nucleoside was employed. [77,86-88] 2-Aminopurine fluorescence has been used to characterize binding of small molecules to the rev responsive element RNA of HIV-1[86], aminoglycosides to the ribosomal A-site, [87,88] and, most recently, argininamide, Tat peptide, and neomycin to TAR RNA model construct HRP7[69] (FIG. 12).

Figure 13:
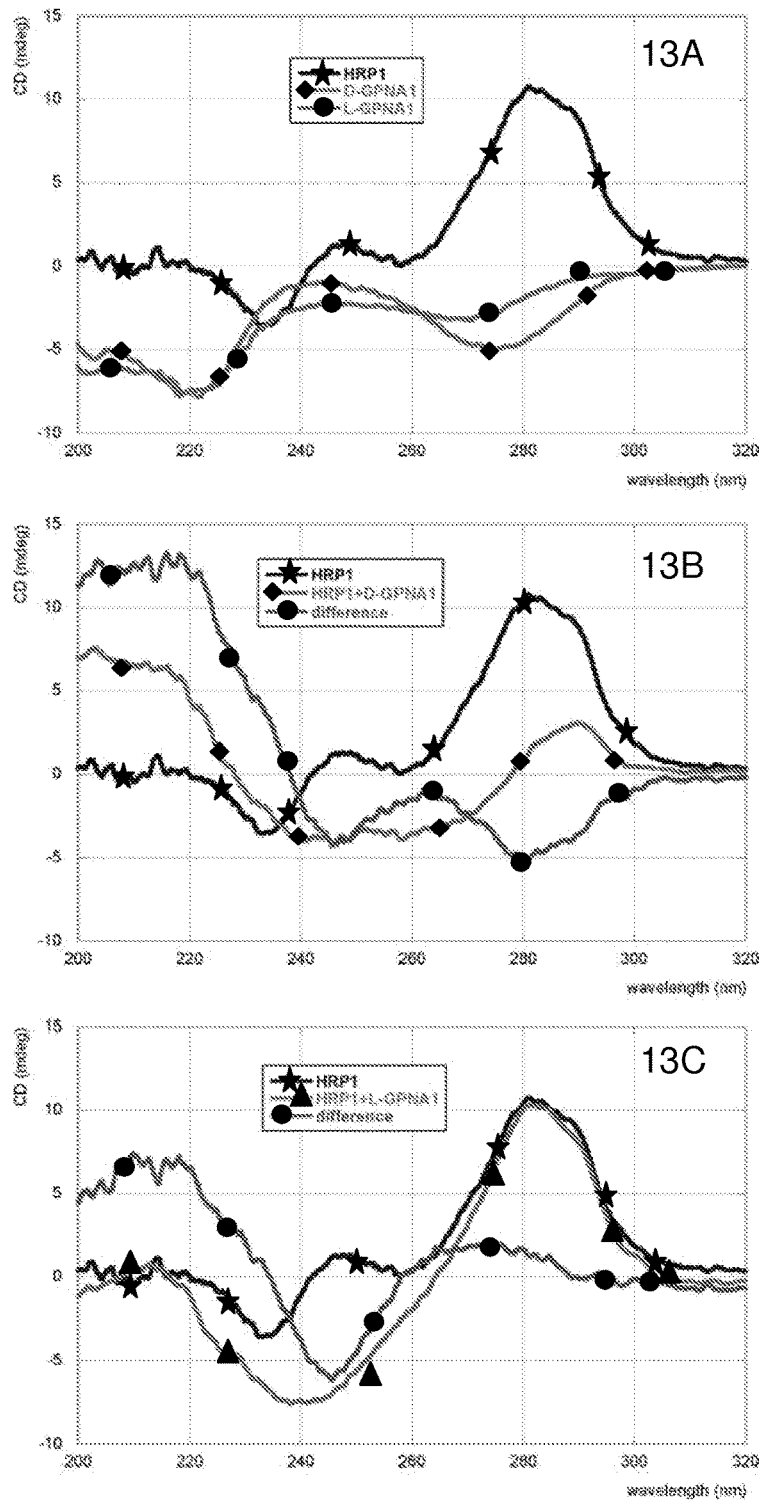
FIGS. 13A-13C show CD spectra.
Figure 14:
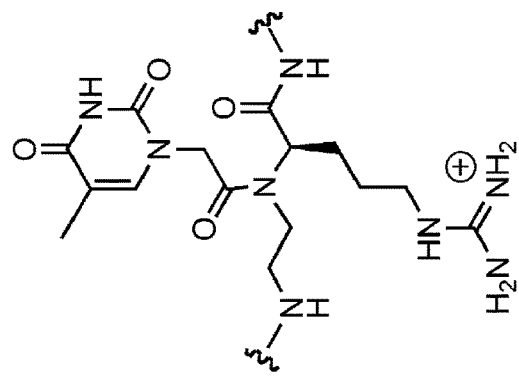
FIG. 14 shows the structure of RNA hairpins, PNA, and GPNA used in the sequence selectivity study.
Figure 14:
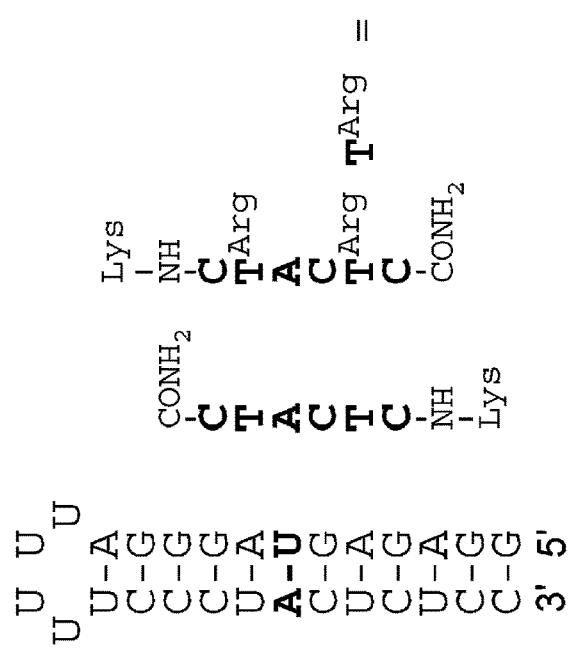
Figure 14:
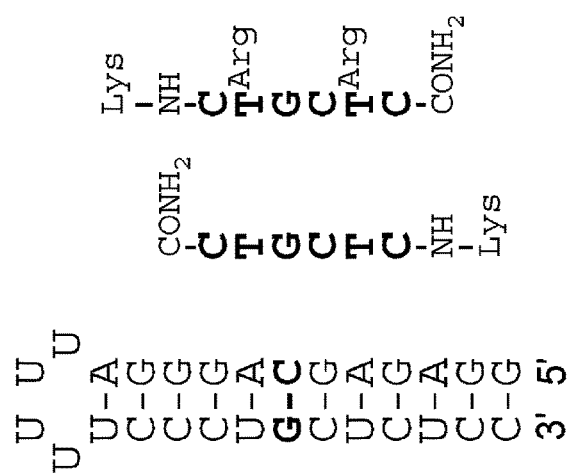
Figure 17:
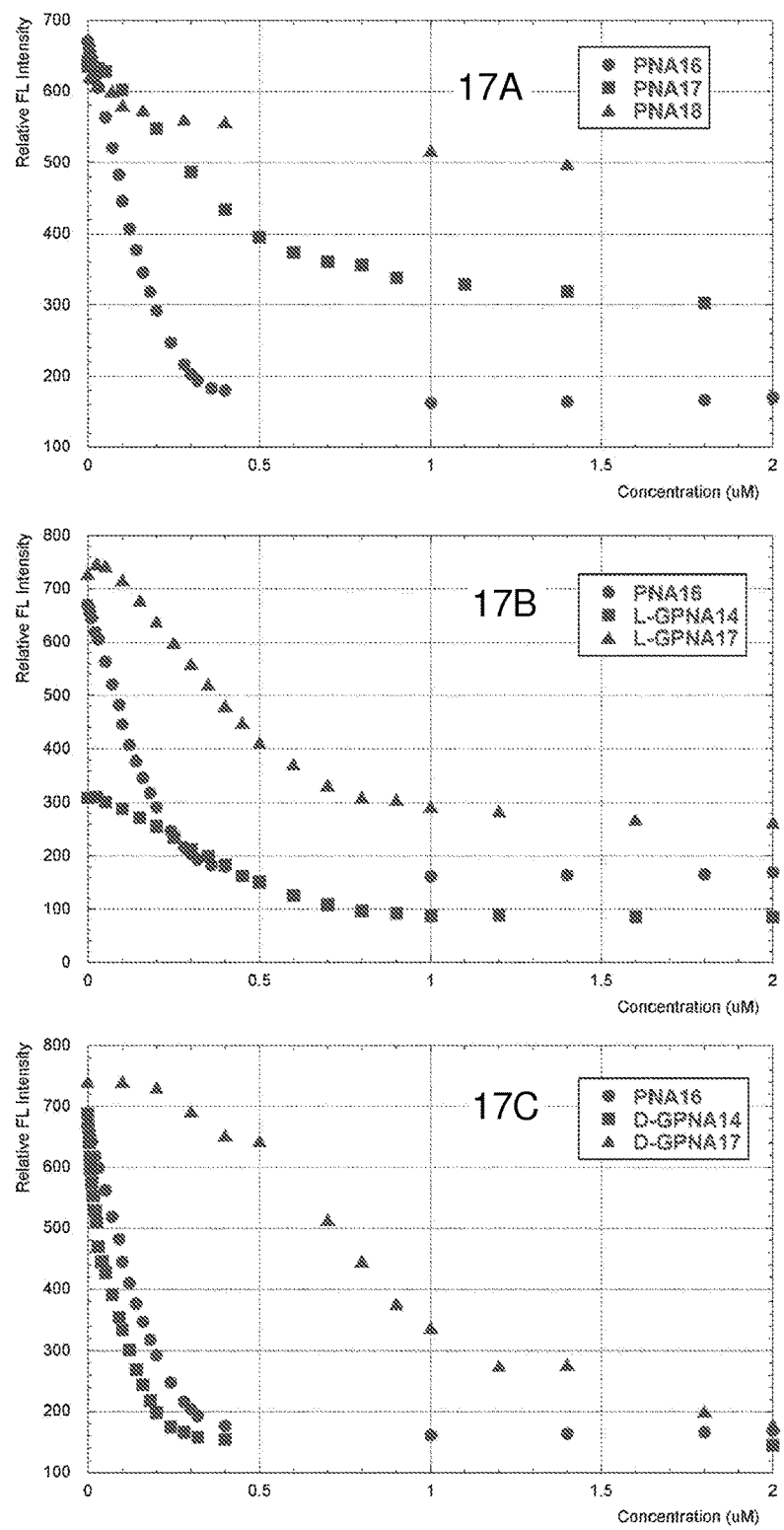
FIGS. 17A-17C show the binding of PNA and GPNA to TAR RNA HRP7; the change in fluorescence was monitored at 365 nm following excitation at 305 nm.

Following the published methodology, [77] incremental titration of HRP7 with PNA16 led to a decrease in fluorescence intensity (red circles in FIG. 13A), as expected for 2-aminopurine moving from a relatively flexible bulge to a more structured PNA-RNA duplex environment. Fitting the data to a single site, two-state binding model gave a Ka of ~2×10$^7$ M$^{-1}$. [77] Introduction of a mismatch (highlighted in bold in FIG. 12) lowered the affinity of PNA17 (squares in FIG. 17A) to ~4×10$^6$ M$^{-1}$. Two adjacent mismatches in PNA18 led to a curve (triangles in FIG. 17A) that fit poorly the single-site, two-state binding model; however, the relatively small slope clearly indicated a significantly decreased affinity. Binding of L-GPNA14 to HRP7 appeared to be weaker than that of unmodified PNA16 (FIG. 17B). The curve did not fit well the single-site, two-state binding model, giving a $K_a$ of approximately 2-5×10$^6$ M$^{-1}$, which was comparable to that of PNA17 having a mismatched base pair. Surprisingly, introduction of a mismatch did not significantly change the affinity of L-GPNA17 (FIG. 17B. This result might indicate that a significant portion of the binding energy came from nonspecific electrostatic attraction. In contrast, D-GPNA14 had an apparently higher affinity for HRP7 than the unmodified PNA16 (squares in FIG. 17C). Fitting the data to a single-site, two-state binding model gave a $K_a$ of ~10$^8$ M-1. [77] Introduction of a mismatch lowered the affinity of D-GPNA17 (triangles in FIG. 17C). The curve did not fit well the single-site, two-state binding model, giving a $K_a$ of approximately 2×10$^6$ M$^{-1}$, which was comparable to that of the mismatched PNA17 and L-GPNA17. One potential explanation for the poor fitting of data for mismatched PNA18, LGPNA, and D-GPNA17 is that more than 1 equivalent of PNA was binding to HRP7, causing significant deviations from the single-site, two-state binding model behavior.

Figure 18:
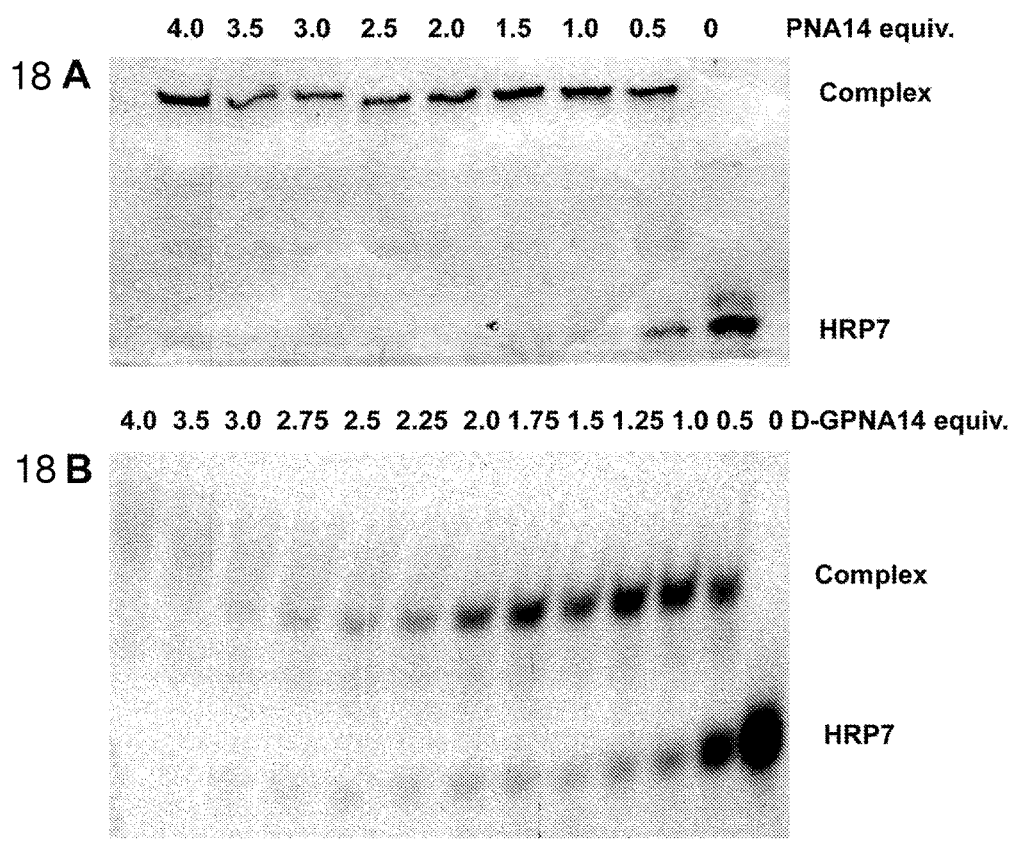
FIG. 18A shows binding of PNA16 and FIG. 18B shows biding of D-GPNA14 to 5'-fluorescein-labeled TAR RNA HRP7 (5 μM) monitored by a gel mobility shift assay; gels were run in 89 mM tris-borate buffer and 2 mM EDTA (pH 8.4).

Formation of the complex between the TAR RNA model hairpin and PNA was further confirmed using a gel mobility shift assay (FIGS. 18A and 18B). Incremental titration of HRP7 (5'-labeled with fluorescein) with PNA16 (FIG. 18A) and DGPNA14 (FIG. 18B) led to the disappearance of the RNA band and formation of a slower-moving band, which could be assigned to a potential strand invasion complex. [85,20] Interestingly and in contrast to PNA16, addition of >2 equiv of DGPNA14 led to the disappearance of the initial complex band and formation of broad and smeared out bands that were diluted below the detection level. This result suggested that >1 equiv of guanidine-modified PNA may be binding to HRP7 with a lower affinity at higher PNA:RNA ratios.

Discussion

PNA bearing cationic α- and γ-substituents bind strongly to cDNA and RNA and exhibit interesting biological properties. [74-76,89-91] Ly and co-workers [74-76] have reported that guanidine modification of PNA greatly facilitates the traversal of the cellular membrane, a highly desirable property for in vivo applications of gene expression control. They found that GPNA induced a potent and sequence specific antisense effect and was less toxic to the cells compared to PNA conjugated with polyarginine. [89] These favorable properties prompted study of binding of GPNA to double-helical RNA, especially because it was recently discovered that unmodified PNA bind surprisingly strongly and sequence selectively to double-helical RNA. [72,5,4]

Ly and co-workers demonstrated that L-GPNA had a lower affinity for complementary single-stranded DNA [74] and RNA [75] than unmodified PNA. In contrast, the affinity of D-GPNA was similar or even higher than that of unmodified PNA. [74,75] Both isomers of GPNA sequences optimized for parallel binding to the polypurine tract of double-helical RNA had binding affinities ~2 orders of magnitude lower than that of the unmodified PNA (cf., Table 7, entry 6 and entries 7-12). This result suggested that a PNA backbone derived from α-substituted amino acids instead of glycine might be a poor fit for the PNA-RNA-RNA triple helix. The problem is most likely steric hindrance because the cationic guanidine modification could be expected to enhance the stability of triple helices at the expense of sequence selectivity. For example, conjugation of cationic peptides at PNA termini has been shown to increase the stability of PNA-DNA-DNA triple helices.[20] Interestingly, Ly and co-workers [76] found that GPNA T10 formed a GPNA-DNA duplex but not a GPNA-DNA-GPNA triplex with the complementary dA$_{10}$, a result consistent with findings that the guanidine modification disfavors triple-helix formation.

GPNA sequences optimized for antiparallel binding to the polypurine tract had somewhat higher affinities for double-helical RNA than the parallel GPNA sequences (Ka=10$^6$-10$^7$, depending on the sequence and number of modifications). However, the affinity was lower than that of unmodified PNA and decreased with an increasing number of guanidine modifications (Table 7, entries 13-15). Multiple modifications derived from L-arginine appeared to be better tolerated, leading to a higher affinity of L-GPNA (Table 7, entry 16) than DGPNA (entry 15). This was somewhat unexpected because DGPNA were shown to form more stable duplexes with DNA and RNA than L-GPNA. [74,75] However, if the antiparallel GPNA bind RNA by triplex invasion, both the favored antiparallel GPNA-RNA duplex and the antiparallel GPNA-RNA-GPNA triple helix (see FIGS. 12A-12C) contribute to the overall stability of the complex. Unmodified PNA was shown to form both parallel and antiparallel triple helices with RNA (FIGS. 12A and 12B), though the latter was 1 order of magnitude less stable.[4] It is conceivable that the antiparallel triple helix is disfavored more by the D modification than by the L modification.

For the symmetric sequence CTCCTC, which was optimal for both the parallel triple helix and the antiparallel duplex (as required for triplex invasion), an overall decrease in binding affinity was observed upon guanidine modification (Table 7, entries 1-3). Consistent with more stable duplexes involving D-GPNA[75] and equally destabilized parallel triple helices (Table 7, entries 6-12), D-GPNA1 had a slightly higher affinity than LGPNA1 (cf., entries 2 and 3). Perhaps the most interesting finding was that guanidine modification shifted the binding mode from 1:1 (as indicated by a binding stoichiometry of ~1), which was assigned to the GPNA-RNA-RNA triplex, to 2:1 (binding stoichiometry of ~2). The best explanation for the 2:1 complex is a GPNA-RNA-GPNA triplex invasion complex (FIG. 12C). The relatively higher stability of GPNA-RNA complexes that can form Watson-Crick base pairs (D-GPNA8 with HRP3 and D-GPNA9 with HRP4) or G-U wobble pair supports the hypothesis of triplex invasion. Thus, guanidine modification of PNA at the α-position appears to enhance the strand invasion of the RNA double helix, which is consistent with observations made by others that cationic modifications and α- and γ-substituents predispose PNA for strand invasion of DNA.[74,75,92-94] Experiments with TAR RNA model HRP7 further confirmed that guanidine modification promotes RNA strand invasion.

The fact that D-GPNA14 had a significantly higher affinity and sequence selectivity than L-GPNA14 was encouraging for future applications and fully consistent with previous findings by Ly and co-workers. [74,75] Overall, the guanidine modification significantly weakened the ability of PNA to form triple helices with complementary double-helical RNA. Meanwhile, the affinity of GPNA and unmodified PNA for mismatched RNA helices was lowered by approximately the same extent (Table 9), which resulted in an overall decrease in sequence selectivity for GPNA.

Binding of PNA to A-site RNA had not been previously studied.[5] The results show that unmodified PNA were able to bind the polypurine tract of bacterial A-site RNA in preference to human A-site RNA. The relatively low affinity and modest sequence selectivity of binding were most likely due to the inability of Hoogsteen triplets to recognize the pyrimidine interruption in the polypurine tract of HRP6. The results with PNA11 and PNA12 are encouraging for triplex recognition of A-site RNA, providing that a modified heterocycle could be designed that would recognize the pyrimidine interruption in the polypurine tract and restore binding affinity and sequence selectivity. [95-97] Consistent with this notion, incorporation of modified heterocyles [P and Pex (FIG. 15)], recently developed by us to recognize cytosine in G-C inversion, [5] significantly increased the sequence selectivity while maintaining excellent affinity in the triple-helical binding mode (Table 9). A brief review of secondary structure databases of noncoding RNAs reveals that it is relatively common to find short homopurine tracts of eight and more contiguous purines, sometimes interrupted by one or two pyrimidines, in bacterial rRNAs (www.rna.ccbb.u-texas.edu) and micro RNAs (www.mirbase.org). Preliminary results with PNA13 and PNA14 suggest the possibility of designing relatively small PNA analogues to recognize such binding sites. It is conceivable that further development of chemical modifications may allow general recognition of isolated pyrimidines in the context of the homopurine triple helix at physiological pH, which may open a novel way to recognize and interfere with function of noncoding RNAs.

Because of the need for cytosine (pKa~4.5) protonation to form the Hoogsteen C*G-C triplets, the experiments on triplehelical recognition of RNA were performed at pH 5.5. Consistent with this requirement, binding of GPNA to RNA hairpins at physiologically relevant pH values was not observed. While the α-guanidine-modified PNA did not improve triple-helix formation with double-helical RNA, related cationic modifications, such as PNA modified with γ-guanidine [91] and γ-lysine, [90] still are interesting alternatives, which may allow effective triple-helical recognition and enhanced cellular uptake to be realized in a modified PNA analogue.

Binding of PNA to TAR RNA has previously been demonstrated by gel mobility shift analysis and by blocking the Tat-mediated transactivation in a cell culture. [84, 85] The data are consistent with formation of a 1:1 PNA-RNA strand invasion duplex. [84, 85] Similarly, PNA14 and especially D-GPNA14 showed excellent affinity and sequence selectivity for TAR RNA. The gel mobility shift assay and a good fit of the fluorescence data to a single-site, two-state binding model suggested formation of a 1:1 PNA-RNA complex, most likely a strand invasion duplex, as previously reported by others. [85] However, gel mobility experiments also indicated that guanidine modifications may cause nonselective binding of additional PNA molecules to the RNA hairpin at higher concentrations. Consistent with the literature data, [84, 85] guanidine modification in L-GPNA14 decreased the binding affinity and sequence selectivity. D-GPNA this may be used to explore for strand invasion recognition of biologically relevant RNAs featuring hairpin structures that are thermally weaker because of noncanonical base pairs, bulges, and internal loops.

While preferred embodiments of the invention have been described, it will be understood that those skilled in the art may combine, subcombine and permute the disclosure herein within the scope of the claims that follow.

REFERENCES

Each of the following is expressly incorporated herein by reference in its entirety:

[1] P. A. Sharp, "The Centrality of RNA (Leading Edge Essay)", *Cell* 2009, 136, 577-580.

[2] Thomas, J. R., and Hergenrother, P. J. (2008) Targeting RNA with Small Molecules. Chem. Rev. 108, 1171-1224.

[3] L. Guan, M. D. Disney, "Recent advances in developing small molecules targeting RNA", *ACS Chem. Biol.* 2012, 7, 73-86.

[4] M. Li, T. Zengeya, E. Rozners, "Short Peptide Nucleic Acids Bind Strongly to Homopurine Tract of Double Helical RNA at pH 5.5", *J. Am. Chem. Soc.* 2010, 132, 8676-8681.

[5] P. Gupta, T. Zengeya, E. Rozners, "Triple helical recognition of pyrimidine inversions in polypurine tracts of RNA by nucleobase-modified PNA", *Chem. Commun.* 2011, 47, 11125-11127.

[6] P. Gupta, O. Muse, E. Rozners, "Recognition of double-stranded RNA by guanidine-modified peptide nucleic acids", *Biochemistry* 2012, 51, 63-73

[7] S. Buchini, C. J. Leumann, "Stable and selective recognition of three base pairs in the parallel triple-helical DNA binding motif", *Angew. Chem.* 2004, 116, 4015-4018; S. Buchini, C. J. Leumann, *Angew. Chem., Int. Ed.* 2004, 43, 3925-1224.

[8] A. B. Eldrup, O. Dahl, P. E. Nielsen, "A novel PNA monomer for recognition of thymine in triple helix structures", *J. Am. Chem. Soc.* 1997, 119, 11116-11117.

[9] L R. Stewart, M. G. Harris, "Comparison of the acidities and basicities of amino-substituted nitrogen heterocycles", *J. Org. Chem.* 1978, 43, 3123-3126.

[10] T. J. Povsic, P. B. Dervan, J, "Triple helix formation by oligonucleotides on DNA extended to the physiological pH range", *Am. Chem. Soc.* 1989, 111, 3059-3061.

[11] S. Hildbrand, A. Blaser, S. P. Parel, C. J. Leumann, "5-Substituted 2-aminopyridine C-nucleosides as protonated cytidine equivalents: increasing efficiency and selectivity in DNA triple-helix formation", *J. Am. Chem. Soc.* 1997, 119, 5499-5511.

[12] S. A. Cassidy, P. Slickers, J. O. Trent, D. C. Capaldi, P. D. Roselt, C. B. Reese, S. Neidle, K. R. Fox, "Recognition of GC base pairs by triplex forming oligonucleotides containing nucleosides derived from 2-aminopyridine", *Nucleic Acids Res.* 1997, 25, 4891-4898.

[13] D. A. Rusling, V. E. C. Powers, R. T. Ranasinghe, Y. Wang, S. D. Osborne, T. Brown, K. R. Fox, "Four base recognition by triplex-forming oligonucleotides at physiological pH", *Nucleic Acids Res.* 2005, 33, 3025-3032.

[14] D. L. Chen, L. W. McLaughlin, "Use of pKa differences to enhance the formation of base triplets involving C-G and G-C base pairs", *J. Org. Chem.* 2000, 65, 7468-7474.

[15] A. Ono, P. O. P. Ts'o, L. S. Kan, "Triplex formation of oligonucleotides containing 2'-O-methylpseudoisocytidine in substitution for 2'-deoxycytidine", *J. Am. Chem. Soc.* 1991, 113, 4032-4033.

[16] G. Xiang, W. Soussou, L. W. McLaughlin, "A New Pyrimidine Nucleoside (m5oxC) for the pH-Independent Recognition of G-C Base Pairs by Oligonucleotide-Directed Triplex Formation", *J. Am. Chem. Soc.* 1994, 116, 11155-11156.

[17] G. Xiang, R. Bogacki, L. W. McLaughlin, "Use of a pyrimidine nucleoside that functions as a bidentate hydrogen bond donor for the recognition of isolated or contiguous G-C base pairs by oligonucleotide-directed triplex formation.", Nucleic Acids Res. 1996, 24, 1963-1970.

[18] U. von Krosigk, S. A. Benner, "pH-Independent Triple Helix Formation by an Oligonucleotide Containing a Pyrazine Donor-Donor-Acceptor Base", *J. Am. Chem. Soc.* 1995, 117, 5361-5362.

[19] M. Egholm, L. Christensen, K. L. Dueholm, O. Buchardt, J. Coull, P. E. Nielsen, "Efficient pH-independent sequence-specific DNA binding by pseudoisocytosine-containing bis-PNA", *Nucleic Acids Res.* 1995, 23, 217-222.

[20] M. E. Hansen, T. Bentin, P. E. Nielsen, "High-affinity triplex targeting of double stranded DNA using chemically modified peptide nucleic acid oligomers", *Nucleic Acids Res.* 2009, 37, 4498-4507.

[21] F. Wojciechowski, R. H. E. Hudson, "A Fmoc/Boc pseudoisocytosine monomer for peptide nucleic acid synthesis", *Can. J. Chem.* 2008, 86, 1026-1029.

[22] A. L. Feig, "Studying RNA-RNA and RNA-Protein Interactions by Isothermal Titration calorimetry", *Methods Enzymol.* 2009, 468, 409-422.

[23] E. S. Priestley, P. B. Dervan, "Sequence Composition Effects on the Energetics of Triple Helix Formation by Oligonucleotides Containing a Designed Mimic of Protonated Cytosine", *J. Am. Chem. Soc.* 1995, 117, 4761-4765.

[24] B. Song, Y. Wang, M. A. Titmus, G. Botchkina, A. Formentini, M. Kornmann, J. Ju, "Molecular mechanism of chemoresistance by miR-215 in osteosarcoma and colon cancer cells", *Molecular Cancer* 2010, 9:96, pp. 1-10.

[25] Z. Jin, F. M. Selaru, Y. Cheng, T. Kan, R. Agarwal, Y. Mori, A. V. Olaru, J. Yang, S. David, J. P. Hamilton, J. M. Abraham, J. Harmon, M. Duncan, E. A. Montgomery, S. J. Meltzer, "MicroRNAs-192 and -215 are upregulated in human gastric cancer and suppress ALCAM expression in vitro", Oncogene 2011, 30, 1577-1585.

[26] S. Griffiths-Jones, H. K. Saini, S. van Dongen, A. J. Enright, "miRBase: tools for microRNA genomics", *Nucleic Acids Res.* 2008, 36, D154-D158.

[27] M. Krishnamurthy, K. Simon, A. M. Orendt, P. A. Beal, "Macrocyclic Helix-Threading Peptides for Targeting RNA", *Angew. Chem.* 2007, 119, 7174-7177; *Angew. Chem., Int. Ed.* 2007, 46, 7044-7047.

[28] B. D. Gooch, P. A. Beal, "Recognition of duplex RNA by helix-threading peptides", *J. Am. Chem. Soc.* 2004, 126, 10603-10610.

[29] Zengeya T, Gupta P, Rozners E., "Triple-helical recognition of RNA using 2-aminopyridine-modified PNA at physiologically relevant conditions", Angew Chem Int Ed Engl. 2012 Dec. 7; 51(50):12593-6. doi: 10.1002/anie.201207925. Epub 2012 Nov. 4.(1).

[30] Nielsen, P. E. (2010) "Sequence-selective targeting of duplex DNA by peptide nucleic acids", Curr. Opin. Mol. Ther. 12, 184-191.

[31] Hansen, M. E., Bentin, T., and Nielsen, P. E. (2009), "High-affinity triplex targeting of double stranded DNA using chemically modified peptide nucleic acid oligomers", Nucleic Acids Res. 37, 4498-4507.

[32] Wancewicz, E. V., Maier, M. A., Siwkowski, A. M., Albertshofer, K., Winger, T. M., Berdeja, A., Gaus, H., Vickers, T. A., Bennett, C. F., Monia, B. P., Griffey, R. H., Nulf, C. J., Hu, J., Corey, D. R., Swayze, E. E., and Kinberger, G. A. (2011), "Peptide nucleic acids conjugated to short basic peptides show improved pharmacokinetics and antisense activity in adipose tissue", J. Med. Chem. 53, 3919-3926.

[33] Hu, J., Matsui, M., Gagnon, K. T., Schwartz, J. C., Gabillet, S., Arar, K., Wu, J., Bezprozvanny, I., and Corey, D. R. (2009), "Allelespecific silencing of mutant huntingtin and ataxin-3 genes by targeting expanded CAG repeats in mRNAs", Nat. Biotechnol. 27, 478-484.

[34] Hu, J., and Corey, D. R. (2007), "Inhibiting gene expression with peptide nucleic acid (PNA)-peptide conjugates that target chromosomal DNA", Biochemistry 46, 7581-7589.

[35] Fabani, M. M., Abreu-Goodger, C., Williams, D., Lyons, P. A., Tones, A. G., Smith, K. G. C., Enright, A. J., Gait, M. J., and Vigorito, E. (2010), "Efficient inhibition of miR-155 function in vivo by peptide nucleic acids", Nucleic Acids Res. 38, 4466-4475.

[36] Fabani, M. M., and Gait, M. J. (2008), "miR-122 targeting with LNA/2'-O-methyl oligonucleotide mixmers, peptide nucleic acids (PNA), and PNA-peptide conjugates", RNA 14, 336-346.

[37] Murtola, M., Zaramella, S., Yeheskiely, E., and Strömberg, R. (2010), "Cationic peptides that increase the thermal stabilities of 2'-OMeRNA/RNA duplexes but do not affect DNA/DNA melting", ChemBioChem 11, 2606-2612.

[38] Chenoweth, D. M., Meier, J. L., and Dervan, P. B. (2013), "Pyrrole-imidazole polyamides distinguish between double-helical DNA and RNA", Angew. Chem., Int. Ed. 52, 415-418.

[39] Bryson, D. I., Zhang, W., McLendon, P. M., Reineke, T. M., and Santos, W. L. (2012), "Toward targeting RNA structure: Branched peptides as cell-permeable ligands to TAR RNA", ACS Chem. Biol. 7, 210-217.

[40] Nielsen, P. E. (2005), "Addressing the challenges of cellular delivery and bioavailability of peptide nucleic acids (PNA)", Q. Rev. Biophys. 38, 345-350.

[41] Calin, G. A., and Croce, C. M. (2006), "MicroRNA signatures in human cancers", Nat. Rev. Cancer 6, 857-866.

[42] www.rna.ccbb.utexas.edu/

[43] www.ncrna.org/frnadb/

[44] Shields, George C., Charles A. Laughton, and Modesto Orozco. "Molecular Dynamics Simulation of a PNA⊙DNA⊙PNA Triple Helix in Aqueous Solution." *Journal of the American Chemical Society* 120.24 (1998): 5895-5904.

[45] Shields, George C., Charles A. Laughton, and Modesto Orozco. "Molecular Dynamics Simulations of the d (T⊙A⊙T) Triple Helix." *Journal of the American Chemical Society* 119.32 (1997): 7463-7469.

[46] Praseuth, D., A. L. Guieysse, and C. Helene. "Triple helix formation and the antigene strategy for sequence-specific control of gene expression." *Biochimica et Biophysica Acta (BBA)-Gene Structure and Expression* 1489.1 (1999): 181-206.

[47] Sun, Jian-sheng, Therese Carestier, and Claude Hélène. "Oligonucleotide directed triple helix formation." *Current opinion in structural biology* 6.3 (1996): 327-333.

[48] Nielsen, Peter E., Michael Egholm, and Ole Buchardt. "Evidence for (PNA) 2/DNA triplex structure upon binding of PNA to dsDNA by strand displacement." *Journal of Molecular*

[49] Nielsen, Peter E., Michael Egholm, and Ole Buchardt. "Peptide nucleic acid (PNA). A DNA mimic with a peptide backbone." *Bioconjugate chemistry* 5.1 (1994): 3-7. *Recognition* 7.3 (2004): 165-170.

[50] Nielsen, Peter E., et al. "Sequence specific inhibition of DNA restriction enzyme cleavage by PNA." *Nucleic acids research* 21.2 (1993): 197-200.

[51] Diviacco, Silvia, et al. "Site-directed inhibition of DNA replication by triple helix formation." *The FASEB Journal* 15.14 (2001): 2660-2668.

[52] Casey, Brian P., and Peter M. Glazer. "Gene targeting via triple-helix formation." *Progress in nucleic acid research and molecular biology* 67 (2001): 163-192.

[53] Faruqi, A. Fawad, et al. "Triple-helix formation induces recombination in mammalian cells via a nucleotide excision repair-dependent pathway." *Molecular and cellular biology* 20.3 (2000): 990-1000.

[54] Kim, Seog K., et al. "Right-handed triplex formed between peptide nucleic acid PNA-T8 and poly (dA) shown by linear and circular dichroism spectroscopy." *Journal of the American Chemical Society* 115.15 (1993): 6477-6481.

[55] Almarsson, Orn, and Thomas C. Bruice. "Peptide nucleic acid (PNA) conformation and polymorphism in PNA-DNA and PNA-RNA hybrids." *Proceedings of the National Academy of Sciences* 90.20 (1993): 9542-9546.

[56] Gowers, Darren M., and Keith R. Fox. "Towards mixed sequence recognition by triple helix formation." *Nucleic acids research* 27.7 (1999): 1569-1577.

[57] Uhlmann, Eugen, et al. "PNA: synthetic polyamide nucleic acids with unusual binding properties." *Angewandte Chemie International Edition* 37.20 (1998): 2796-2823.

[58] Rusling, David A., Tom Brown, and Keith R. Fox. "DNA Recognition by Triple Helix Formation." *Sequence-specific DNA Binding Agents* (2006): 1-27.

[59] Leumann, Christian J. "Design and evaluation of oligonucleotide analogues." *CHIMIA International Journal for Chemistry* 55.4 (2001): 295-301.

[60] Froehler, Brian, et al. "Enhanced triple-helix and double-helix formation with oligomers containing modified pyrimidines." U.S. Pat. No. 6,875,593. 5 Apr. 2005.

[61] Asseline, Ulysse. "Chemical Modifications of Triple Helix Forming Oligonucleotides." *Triple Helix Forming Oligonucleotides* (1999): 63-73.

[62] Szostak, Jack W. "Non-Enzymatic RNA Replication and the Origin of Life." *Biol* 74 (2009): 47-54.

[63] Fox, KeithR, and Tom Brown. "Formation of stable DNA triplexes." *Biochemical Society Transactions* 39.2 (2011): 629.

[64] Sucheck, S. J., and Wong, C. H. (2000), "RNA as a target for small molecules", Curr. Opin. Chem. Biol. 4, 678-686.

[65] Chow, C. S., and Bogdan, F. M. (1997), "A Structural Basis for RNA-Ligand Interactions", Chem. Rev. 97, 1489-1513.

[66] Fox, K. R., and Brown, T. (2005), "An extra dimension in nucleic acid sequence recognition", Q. Rev. Biophys. 38, 311-320.

[67] Roberts, R. W., and Crothers, D. M. (1992), "Stability and properties of double and triple helices: Dramatic effects of RNA or DNA backbone composition", Science 258, 1463-1466.

[68] Han, H., and Dervan, P. B. (1993), "Sequence-specific recognition of double helical RNA and RNA-DNA by triple helix formation", Proc. Natl. Acad. Sci. U.S.A. 90, 3806-3810.

[69] Escude, C., Francois, J. C., Sun, J. S., Ott, G., Sprinzl, M., Garestier, T., and Helene, C. (1993), "Stability of triple helixes containing RNA and DNA strands: Experimental and molecular modeling studies", Nucleic Acids Res. 21, 5547-5553.

[70] Semerad, C. L., and Maher, L. J. III (1994), "Exclusion of RNA strands from a purine motif triple helix", Nucleic Acids Res. 22, 5321-5325.

[71] Nielsen, P. E., Egholm, M., Berg, R. H., and Buchardt, O. (1991), "Sequence-selective recognition of DNA by strand displacement with a thymine-substituted polyamide", Science 254, 1497-1500.

[72] Zengeya, T., Li, M., and Rozners, E. (2011), "PNA containing isocytidine nucleobase: Synthesis and recognition of double helical RNA", Bioorg. Med. Chem. Lett. 21, 2121-2124.

[73] Shiraishi, T., and Nielsen, P. E. (2006), "Enhanced delivery of cell-penetrating peptide-peptide nucleic acid conjugates by endosomal disruption", Nat. Protoc. 1, 633-636.

[74] Zhou, P., Dragulescu-Andrasi, A., Bhattacharya, B., O'Keefe, H., Vatta, P., Hyldig-Nielsen, J. J., and Ly, D. H. (2006), "Synthesis of cellpermeable peptide nucleic acids and characterization of their hybridization and uptake properties", Bioorg. Med. Chem. Lett. 16, 4931-4935.

[75] Dragulescu-Andrasi, A., Zhou, P., He, G., and Ly, D. H. (2005), "Cell-permeable GPNA with appropriate backbone stereochemistry and spacing binds sequence-specifically to RNA", Chem. Commun., 244-246.

[76] Zhou, P., Wang, M., Du, L., Fisher, G. W., Waggoner, A., and Ly, D. H. (2003), "Novel Binding and Efficient Cellular Uptake of Guanidine-Based Peptide Nucleic Acids (GPNA)", J. Am. Chem. Soc. 125, 6878-6879.

[77] Bradrick, T. D., and Marino, J. P. (2004), "Ligand-induced changes in 2-aminopurine fluorescence as a probe for small molecule binding to HIV-1 TAR RNA", RNA 10, 1459-1468.

[78] Wojciechowski, F., and Hudson, R. H. E. (2008), "A Convenient Route to N-[2-(Fmoc)aminoethyl]glycine Esters and PNA Oligomerization Using a Bis-N-Boc Nucleobase Protecting Group Strategy", J. Org. Chem. 73, 3807-3816.

[79] Kleiner, R. E., Brudno, Y., Birnbaum, M. E., and Liu, D. R. (2008), "DNA-Templated Polymerization of Side-Chain-Functionalized Peptide Nucleic Acid Aldehydes", J. Am. Chem. Soc. 130, 4646-4659.

[80] Wittung, P., Nielsen, P., and Norden, B. (1996), "Direct Observation of Strand Invasion by Peptide Nucleic Acid (PNA] into Double-Stranded DNA", J. Am. Chem. Soc. 118, 7049-7054.

[81] Wittung, P., Nielsen, P., and Norden, B. (1997), "Extended DNA-recognition repertoire of peptide nucleic acid (PNA): PNA-dsDNA triplex formed with cytosine-rich homopyrimidine PNA", Biochemistry 36, 7973-7979.

[82] Kaushik, N., Basu, A., Palumbo, P., Myers, R. L., and Pandey, V. N. (2002), "Anti-TAR polyamide nucleotide analog conjugated with a membrane-permeating peptide inhibits human immunodeficiency virus type 1 production", J. Virol. 76, 3881-3891.

[83] Tripathi, S., Chaubey, B., Ganguly, S., Harris, D., Casale, R. A., and Pandey, V. N. (2005), "Anti-HIV-1 activity of anti-TAR polyamide nucleic acid conjugated with various membrane transducing peptides", Nucleic Acids Res. 33, 4345-4356.

[84] Mayhood, T., Kaushik, N., Pandey, P. K., Kashanchi, F., Deng, L., and Pandey, V. N. (2000), "Inhibition of Tat-Mediated Transactivation of HIV-1 LTR Transcription by Polyamide Nucleic Acid Targeted to TAR Hairpin Element", Biochemistry 39, 11532-11539.

[85] Belousoff, M. J., Gasser, G., Graham, B., Tor, Y., and Spiccia, L. (2009), "Binding of HIV-1 TAR mRNA to a peptide nucleic acid oligomer and its conjugates with metal-ion-binding multidentate ligands", J. Biol. Inorg. Chem. 14, 287-300.

[86] Lacourciere, K. A., Stivers, J. T., and Marino, J. P. (2000), "Mechanism of Neomycin and Rev Peptide Binding to the Rev Responsive Element of HIV-1 As Determined by Fluorescence and NMR Spectroscopy", Biochemistry 39, 5630-5641.

[87] Kaul, M., Barbieri, C. M., and Pilch, D. S. (2004), "Fluorescence-Based Approach for Detecting and Characterizing Antibiotic-Induced Conformational Changes in Ribosomal RNA: Comparing Aminoglycoside Binding to Prokaryotic and Eukaryotic Ribosomal RNA Sequences", J. Am. Chem. Soc. 126, 3447-3453.

[88] Blount, K. F., Zhao, F., Hermann, T., and Tor, Y. (2005), "Conformational Constraint as a Means for Understanding RNA Aminoglycoside Specificity", J. Am. Chem. Soc. 127, 9818-9829.

[89] Dragulescu-Andrasi, A., Rapireddy, S., He, G., Bhattacharya, B., Hyldig-Nielsen, J. J., Zon, G., and Ly, D. H. (2006), "Cell-Permeable Peptide Nucleic Acid Designed to Bind to the 5'-Untranslated Region of E-cadherin Transcript Induces Potent and Sequence-Specific Antisense Effects", J. Am. Chem. Soc. 128, 16104-16112.

[90] Englund, E. A., and Appella, D. H. (2007), "γ-substituted peptide nucleic acids constructed from L-lysine are a versatile scaffold for multifunctional display", Angew. Chem., Int. Ed. 46, 1414-1418.

[91] Sahu, B., Chenna, V., Lathrop, K. L., Thomas, S. M., Zon, G., Livak, K. J., and Ly, D. H. (2009), "Synthesis of Conformationally Preorganized and Cell-Permeable Guanidine-Based γ-Peptide Nucleic Acids (γ-GPNAs)", J. Org. Chem. 74, 1509-1516.

[92] Ishizuka, T., Tedeschi, T., Corradini, R., Komiyama, M., Sforza, S., and Marchelli, R. (2009), "SSB-Assisted Duplex Invasion of Preorganized PNA into Double-Stranded DNA", ChemBioChem 10, 2607-2612.

[93] He, G., Rapireddy, S., Bahal, R., Sahu, B., and Ly, D. H. (2009), "Strand Invasion of Extended, Mixed-Sequence B-DNA by γ-PNAs", J. Am. Chem. Soc. 131, 12088-12090.

[94] Kaihatsu, K., Braasch, D. A., Cansizoglu, A., and Corey, D. R. (2002), "Enhanced strand invasion by peptide nucleic acid-peptide conjugates", Biochemistry 41, 11118-11125.

[95] Rusling, D. A., Broughton-Head, V. J., Brown, T., and Fox, K. R. (2008), "Towards the targeted modulation of gene expression by modified triplex-forming oligonucleotides", Curr. Chem. Biol. 2, 1-10.

[96] Rusling, D. A., Powers, V. E. C., Ranasinghe, R. T., Wang, Y., Osborne, S. D., Brown, T., and Fox, K. R. (2005), "Four base recognition by triplex-forming oligonucleotides at physiological pH", Nucleic Acids Res. 33, 3025-3032.

[97] Buchini, S., and Leumann, C. J. (2003), "Recent improvements in antigene technology", Curr. Opin. Chem. Biol. 7, 717-726.

[98] Muse, O., Zengeya, T., Mwaura, J., Hnedzko, D., McGee, D., Grewer, C., and Rozners, E. (2013), "Sequence selective recognition of double-stranded ma at physiologically relevant conditions using pna-peptide conjugates", ACS Chemical Biology, 8(8), 1683-1686.

[99] Weeks, K. M., and Crothers, D. M. (1991), "RNA recognition by Tat-derived peptides: Interactions in the major groove?", Cell 66, 577-588.

[100] Burns, C. J.; Goswami, R.; Jackson, R. W.; Lessen, T.; Li, W.; Pevear, D.; Tirunahari, P. K.; Xu, H. (2010), "Beta-lactamase inhibitors", W2010/130708 PCT/EP2010/056408: patent, 2010; pp 197.

[101] Puglisi, J. D.; Tinoco, I., Jr., (1989), "Absorbance melting curves of RNA" Methods Enzymol. 1989, 180, 304-325.

U.S. Pat. Nos. 5,539,082; 5,547,835; 5,645,985; 5,691,141; 5,714,331; 5,719,262; 5,736,336; 5,766,855; 5,786,461; 5,830,653; 5,871,918; 6,132,971; 6,190,866; 6,194,144; 6,225,450; 6,238,871; 6,248,878; 6,265,380; 6,300,318; 6,357,163; 6,361,951; 6,369,227; 6,380,368; 6,395,474; 6,403,583; 6,414,112; 6,441,130; 6,451,968; 6,500,855; 6,613,873; 6,617,309; 6,653,295; 6,664,373; 6,686,442; 6,710,058; 6,710,163; 6,710,164; 6,713,602; 6,734,161; 6,875,593; 6,878,805; 6,936,418; 6,946,292; 6,951,872; 6,962,783; 7,038,037; 7,049,068; 7,057,027; 7,098,192; 7,157,470; 7,199,107; 7,223,833; 7,235,653; 7,253,180; 7,276,599; 7,297,494; 7,307,069; 7,312,214; 7,339,051; 7,348,418; 7,368,560; 7,378,485; 7,381,732; 7,388,017; 7,390,882; 7,393,683; 7,410,772; 7,425,446; 7,429,604; 7,432,044; 7,507,859; 7,517,659; 7,524,863; 7,541,344; 7,547,768; 7,585,953; 7,615,529; 7,618,632; 7,622,265; 7,662,929; 7,678,895; 7,683,036; 7,691,568; 7,691,810; 7,696,345; 7,704,503; 7,713,944; 7,718,628; 7,737,325; 7,741,442; 7,749,504; 7,754,441; 7,754,450; 7,759,318; 7,759,319; 7,767,403; 7,786,292; 7,790,691; 7,803,915; 7,807,372; 7,812,149; 7,829,584; 7,846,725; 7,858,330; 7,884,086; 7,888,478; 7,897,582; 7,902,163; 7,919,612; 7,923,538; 7,939,268; 7,951,546; 7,960,355; 7,981,868; 7,985,844; 7,989,595; 7,994,290; 8,008,004; 8,012,947; 8,039,595; 8,067,175; 8,067,232; 8,084,200; 8,084,459; 8,101,185; 8,106,025; 8,110,195; 8,110,558; 8,124,745; 8,129,515; 8,133,876; 8,158,760; 8,178,506; 8,183,363; 8,193,246; 8,206,901; 8,252,756; 8,278,042, expressly incorporated by reference herein in their entirety.

US Pat. Pub. Nos. 20020032175; 20020106683; 20020146718; 20020160383; 20020183324; 20030004344; 20030064962; 20030087268; 20030105286; 20030108544; 20030115614; 20030148408; 20030152953; 20030180734; 20030228305; 20030228319; 20030236389; 20040006062; 20040006203; 20040009541; 20040009602; 20040009938; 20040014051; 20040023917; 20040033977; 20040033978; 20040034191; 20040049021; 20040059087; 20040063115; 20040063179; 20040093621; 20040101853; 20040109865; 20040110704; 20040132718; 20040142346; 20040146902; 20040147022; 20040147023; 20040147470; 20040161777; 20040161844; 20040171028; 20040171029; 20040171031; 20040171032; 20040171033; 20040171564; 20040171566;

| | | | | | |
|---|---|---|---|---|---|
| 20040171570; | 20040180847; | 20040185479; | 20080199960; | 20080207541; | 20080213266; |
| 20040198969; | 20040203024; | 20040229277; | 20080227106; | 20080227196; | 20080241130; |
| 20040235164; | 20040241703; | 20040242860; | 20080241884; | 20080261301; | 20080261904; |
| 20040254158; | 20040254358; | 20040258696; | 20080274993; | 20080306016; | 20080306153; |
| 20040259150; | 20040266706; | 20040266731; | 20080311669; | 20080318239; | 20090004186; |
| 20050009041; | 20050014224; | 20050019915; | 20090017473; | 20090028877; | 20090041749; |
| 20050026160; | 20050026857; | 20050031613; | 20090048435; | 20090053226; | 20090054631; |
| 20050032067; | 20050032068; | 20050032069; | 20090068178; | 20090068251; | 20090075278; |
| 20050037370; | 20050042216; | 20050042647; | 20090075279; | 20090075302; | 20090075317; |
| 20050053965; | 20050053976; | 20050053981; | 20090081660; | 20090117566; | 20090136928; |
| 20050059016; | 20050059066; | 20050064492; | 20090142259; | 20090142806; | 20090143312; |
| 20050074801; | 20050074879; | 20050075307; | 20090186363; | 20090186409; | 20090191199; |
| 20050080032; | 20050080246; | 20050100885; | 20090191592; | 20090203132; | 20090203896; |
| 20050106598; | 20050106644; | 20050107324; | 20090209629; | 20090221095; | 20090221685; |
| 20050107595; | 20050112129; | 20050112770; | 20090228994; | 20090238811; | 20090246129; |
| 20050118605; | 20050119470; | 20050123925; | 20090258931; | 20090286969; | 20090291906; |
| 20050142581; | 20050153336; | 20050164250; | 20090291907; | 20090297531; | 20090298174; |
| 20050170368; | 20050202459; | 20050208523; | 20090298910; | 20090311259; | 20090317907; |
| 20050226867; | 20050226868; | 20050226869; | 20090324490; | 20090324592; | 20100028337; |
| 20050233358; | 20050238650; | 20050245474; | 20100028559; | 20100061996; | 20100076183; |
| 20050260634; | 20050260755; | 20050261218; | 20100080809; | 20100092997; | 20100113350; |
| 20050262593; | 20050272120; | 20050287138; | 20100113523; | 20100113608; | 20100129808; |
| 20050287548; | 20060002943; | 20060009455; | 20100136682; | 20100143388; | 20100158896; |
| 20060024793; | 20060046255; | 20060057148; | 20100158914; | 20100162418; | 20100172882; |
| 20060063254; | 20060064781; | 20060073505; | 20100173285; | 20100184844; | 20100209956; |
| 20060078990; | 20060078991; | 20060084120; | 20100210745; | 20100216982; | 20100233146; |
| 20060089496; | 20060099592; | 20060140961; | 20100233270; | 20100234579; | 20100240738; |
| 20060142193; | 20060142232; | 20060147373; | 20100247430; | 20100249215; | 20100256038; |
| 20060147374; | 20060160731; | 20060160997; | 20100267813; | 20100303834; | 20100311050; |
| 20060210570; | 20060216232; | 20060217339; | 20100322897; | 20110009600; | 20110027271; |
| 20060241071; | 20060241072; | 20060247243; | 20110033451; | 20110038849; | 20110042260; |
| 20060251662; | 20060252722; | 20060257930; | 20110045005; | 20110052610; | 20110054003; |
| 20060270594; | 20060281680; | 20060293269; | 20110059115; | 20110070243; | 20110124591; |
| 20070010009; | 20070015722; | 20070041983; | 20110129457; | 20110137016; | 20110171176; |
| 20070048218; | 20070048326; | 20070048825; | 20110171287; | 20110177103; | 20110178157; |
| 20070049547; | 20070053835; | 20070054361; | 20110206658; | 20110206702; | 20110224277; |
| 20070054869; | 20070065861; | 20070065862; | 20110236374; | 20110237522; | 20110240064; |
| 20070087006; | 20070098634; | 20070117124; | 20110250626; | 20110250643; | 20110251258; |
| 20070135364; | 20070148165; | 20070161547; | 20110262406; | 20110263514; | 20110268657; |
| 20070207142; | 20070212735; | 20070219122; | 20110268810; | 20110274690; | 20110293585; |
| 20070219350; | 20070224201; | 20070225282; | 20120009193; | 20120010387; | 20120022238; |
| 20070231323; | 20070243193; | 20070259830; | 20120029049; | 20120035248; | 20120039893; |
| 20070265436; | 20070269446; | 20070276139; | 20120052110; | 20120059046; | 20120077201; |
| 20070286856; | 20080009456; | 20080027019; | 20120097194; | 20120114673; | 20120115136; |
| 20080039618; | 20080051359; | 20080095765; | 20120115228; | 20120122216; | 20120142754; |
| 20080096215; | 20080102468; | 20080119470; | 20120156138; | 20120157514; | 20120171279; |
| 20080124331; | 20080124732; | 20080124739; | 20120184724; | 20120202874; | 20120244230; |
| 20080131920; | 20080146495; | 20080146788; | 20120269730, expressly incorporated by reference herein in their entirety. | | |
| 20080166294; | 20080193446; | 20080194503; | | | |

The invention claimed is:

1. A method of forming a pH 7.4-stable peptide nucleic acid-double stranded ribonucleic acid triple helix, comprising:

providing a peptide nucleic acid sequence having at least one basic amino acid covalently linked to a nucleic acid sequence portion configured to selectively bind to a complementary nucleic acid sequence portion, wherein the nucleic acid sequence portion comprises at least one 2-aminopyridine nucleobase; and contacting a peptide nucleic acid having the peptide nucleic acid sequence with double stranded ribonucleic acid having the complementary nucleic acid sequence portion, to form a peptide nucleic acid double-stranded ribonucleic acid triple helix, in a nucleic acid sequence portion selective manner.

2. The method according to claim 1, wherein the peptide nucleic acid sequence portion has a higher affinity for the double stranded ribonucleic acid having the complementary nucleic acid sequence portion than for a double stranded deoxyribonucleic acid having a corresponding complementary nucleic acid sequence portion.

3. The method according to claim 1, wherein the peptide nucleic acid comprises at least six nucleobases including at least three 2-aminopyridine nucleobases.

4. The method according to claim 1, wherein the at least one amino acid comprises lysine.

5. A method of forming a peptide nucleic acid-double stranded nucleic acid triple helix, comprising:

providing a peptide nucleic acid, comprising a nucleic acid sequence-selective binding portion, the nucleic acid sequence-selective binding portion comprising a plurality of nucleobases and at least one 2-aminopyridine nucleobase, conjugated to at least one basic amino acid; and interacting the peptide nucleic acid with a double stranded nucleic acid having a nucleic acid sequence corresponding to the nucleic acid sequence-selective binding portion, to form the peptide nucleic acid-double stranded nucleic acid triple helix selectively in dependence on the nucleic acid sequence-selective binding portion.

6. The method according to claim 5, wherein the nucleic acid sequence-selective binding portion comprises at least six nucleobases.

7. The method according to claim 5, wherein the nucleic acid sequence-selective binding portion comprises at least three 2-aminopyridine nucleobases.

8. The method according to claim 5, wherein the nucleic acid sequence-selective binding portion comprises at least six nucleobases including at least three 2-aminopyridine nucleobases.

9. The method according to claim 5, wherein the nucleic acid sequence-selective binding portion comprises a copolymer comprising 2-aminopyridine and thymidine.

10. The method according to claim 5, wherein the peptide nucleic acid-double stranded nucleic acid triple helix is stable at pH 7.4 at temperatures less than about 35° C. in a phosphate buffer solution containing 2 mM magnesium chloride, 90 mM potassium chloride, 10 mM sodium chloride, and 50 mM potassium phosphate.

11. The method according to claim 5, wherein the peptide nucleic acid has a higher affinity for a double stranded ribonucleic acid containing the nucleic acid sequence corresponding to the nucleic acid sequence-selective binding portion than for a double stranded deoxyribonucleic acid containing a deoxyribonucleic acid sequence corresponding to the nucleic acid sequence-selective binding portion.

12. The method according to claim 5, wherein the at least one 2-aminopyridine selectively binds to guanosine nucleobases of the nucleic acid sequence.

13. The method according to claim 5, wherein the at least one basic amino acid comprises lysine.

* * * * *

SEQUENCE LISTING

<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: PNA1, 3' Lys-NH-, 5' -CONH2

<400> SEQUENCE: 1
tcttcttctt tc                                                      12

<210> SEQ ID NO 2
<211> LENGTH: 10

```
<212> TYPE: RNA
<213> ORGANISM: Artificial Sequence
<220> FEATURE:
<223> OTHER INFORMATION: Triplex recognition site

<400> SEQUENCE: 2
gugauagggg                                                          10

<210> SEQ ID NO 3
<211> LENGTH: 28
<212> TYPE: RNA
<213> ORGANISM: Artificial Sequence
<220> FEATURE:
<223> OTHER INFORMATION: HRPA

<400> SEQUENCE: 3
gaaagaagaa gauuuucuu cuucuuuc                                       28

<210> SEQ ID NO 4
<211> LENGTH: 28
<212> TYPE: DNA
<213> ORGANISM: Artificial Sequence
<220> FEATURE:
<223> OTHER INFORMATION: DNAA

<400> SEQUENCE: 4
gaaagaagaa gattttctt cttctttc                                       28

<210> SEQ ID NO 5
<211> LENGTH: 28
<212> TYPE: RNA
<213> ORGANISM: Artificial Sequence
<220> FEATURE:
<223> OTHER INFORMATION: HRP1

<400> SEQUENCE: 5
ggagaggagg gauuuuccc uccucucc                                       28

<210> SEQ ID NO 6
<211> LENGTH: 28
<212> TYPE: RNA
<213> ORGANISM: Artificial Sequence
<220> FEATURE:
<223> OTHER INFORMATION: HRP2

<400> SEQUENCE: 6
ggagagaagg gauuuuccc uucucucc                                       28

<210> SEQ ID NO 7
<211> LENGTH: 28
<212> TYPE: RNA
<213> ORGANISM: Artificial Sequence
<220> FEATURE:
<223> OTHER INFORMATION: HRP3

<400> SEQUENCE: 7
ggagagcagg gauuuuccc ugcucucc                                       28

<210> SEQ ID NO 8
<211> LENGTH: 28
<212> TYPE: RNA
<213> ORGANISM: Artificial Sequence
<220> FEATURE:
<223> OTHER INFORMATION: HRP4

<400> SEQUENCE: 8
```

```
ggagaguagg gauuuuccc uacucucc                                    28

<210> SEQ ID NO 9
<211> LENGTH: 28
<212> TYPE: DNA
<213> ORGANISM: Artificial Sequence
<220> FEATURE:
<223> OTHER INFORMATION: HRP5

<400> SEQUENCE: 9
ggagaggagg gattttccc tcctctcc                                    28

<210> SEQ ID NO 10
<211> LENGTH: 32
<212> TYPE: RNA
<213> ORGANISM: Artificial Sequence
<220> FEATURE:
<223> OTHER INFORMATION: HRP6

<400> SEQUENCE: 10
cacaggaaaa ugacuucggc caauauucug ug                              32

<210> SEQ ID NO 11
<211> LENGTH: 28
<212> TYPE: DNA
<213> ORGANISM: Artificial Sequence
<220> FEATURE:
<223> OTHER INFORMATION: DNA analog of HRP2

<400> SEQUENCE: 11
ggagagaagg gattttccc ttctctcc                                    28

<210> SEQ ID NO 12
<211> LENGTH: 31
<212> TYPE: RNA
<213> ORGANISM: Artificial Sequence
<220> FEATURE:
<223> OTHER INFORMATION: HRP6

<400> SEQUENCE: 12
ggugauaggg guucuucgga acuccuacac c                               31

<210> SEQ ID NO 13
<211> LENGTH: 35
<212> TYPE: RNA
<213> ORGANISM: Artificial Sequence
<220> FEATURE:
<223> OTHER INFORMATION: HRP5

<400> SEQUENCE: 13
cgucgcuacu accacuucgg uggaaguaaa agucg                           35

<210> SEQ ID NO 14
<211> LENGTH: 33
<212> TYPE: RNA
<213> ORGANISM: Artificial Sequence
<220> FEATURE:
<223> OTHER INFORMATION: HRP6

<400> SEQUENCE: 14
cgucacguca ugacuucggu ugggacgaag ucg                             33
```